(12) United States Patent
Lynn et al.

(10) Patent No.: US 9,788,973 B2
(45) Date of Patent: *Oct. 17, 2017

(54) SPINAL IMPLANT

(71) Applicant: Pinnacle Spine Group, LLC, Dallas, TX (US)

(72) Inventors: Jim R. Lynn, San Clemente, CA (US); Russell W. Nelson, Westlake Village, CA (US)

(73) Assignee: Pinnacle Spine Group, LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/725,933

(22) Filed: Dec. 21, 2012

(65) Prior Publication Data

US 2013/0184827 A1 Jul. 18, 2013

Related U.S. Application Data

(63) Continuation of application No. 13/049,693, filed on Mar. 16, 2011, now Pat. No. 8,343,224.

(Continued)

(51) Int. Cl.
*A61F 2/44* (2006.01)
*A61F 2/46* (2006.01)
(Continued)

(52) U.S. Cl.
CPC ............ *A61F 2/4611* (2013.01); *A61F 2/442* (2013.01); *A61F 2/447* (2013.01); *A61F 2/4455* (2013.01);
(Continued)

(58) Field of Classification Search
CPC ..................................................... A61F 2/447
(Continued)

(56) References Cited

U.S. PATENT DOCUMENTS 5,123,926 A 6/1992 Pisharodi
5,375,823 A 12/1994 Navas
(Continued)

FOREIGN PATENT DOCUMENTS

EP 425542 B1 3/1995
EP 793463 A1 9/1997
(Continued)

OTHER PUBLICATIONS

International Search Report for International Application No. PCT/US2011/028731 (a PCT counterpart of the present application) dated May 18, 2011.

(Continued)

*Primary Examiner* — Ellen C Hammond
(74) *Attorney, Agent, or Firm* — Knobbe, Martens, Olson & Bear, LLP

(57) ABSTRACT

According to some embodiments, a method for promoting spinal fusion using a spinal implant comprises providing a spinal implant, wherein the spinal implant comprises an anterior wall, a posterior wall and two lateral walls configured to extend between the anterior wall and the posterior wall. In some embodiments, the spinal implant further comprises at least one internal chamber generally positioned between the anterior wall, the posterior wall and the two lateral walls, wherein the internal chamber being is adapted to receive at least one graft and/or other fill material. In some embodiments, at least a portion of the graft and/or other fill material delivered into the internal chamber is configured to exit through the one or more of the openings of the anterior wall.

20 Claims, 27 Drawing Sheets

Related U.S. Application Data

(60) Provisional application No. 61/314,509, filed on Mar. 16, 2010, provisional application No. 61/389,671, filed on Oct. 4, 2010.

(51) Int. Cl.
  *A61F 2/28* (2006.01)
  *A61F 2/30* (2006.01)

(52) U.S. Cl.
  CPC .......... *A61F 2/4465* (2013.01); *A61F 2/4601* (2013.01); *A61F 2/46* (2013.01); *A61F 2002/2817* (2013.01); *A61F 2002/2835* (2013.01); *A61F 2002/3008* (2013.01); *A61F 2002/30271* (2013.01); *A61F 2002/30281* (2013.01); *A61F 2002/30754* (2013.01); *A61F 2002/30904* (2013.01); *A61F 2002/4475* (2013.01); *A61F 2002/464* (2013.01); *A61F 2002/4628* (2013.01); *A61F 2002/4629* (2013.01); *A61F 2002/4631* (2013.01); *A61F 2310/00011* (2013.01)

(58) Field of Classification Search
  USPC ..................................................... 623/17.16
  See application file for complete search history.

(56) References Cited

U.S. PATENT DOCUMENTS

| | | |
|---|---|---|
| 5,489,307 A | 2/1996 | Kuslich et al. |
| 5,593,409 A | 1/1997 | Michelson |
| 5,609,635 A | 3/1997 | Michelson |
| 5,653,763 A | 8/1997 | Errico et al. |
| 5,665,122 A | 9/1997 | Kambin |
| 5,669,909 A | 9/1997 | Zdeblick et al. |
| 5,683,394 A | 11/1997 | Rinner |
| 5,702,455 A | 12/1997 | Saggar |
| 5,716,415 A | 2/1998 | Steffee |
| 5,749,916 A | 5/1998 | Richelsoph |
| 5,766,253 A | 6/1998 | Brosnahan, III |
| 5,772,661 A | 6/1998 | Michelson |
| 5,776,199 A | 7/1998 | Michelson |
| 5,782,919 A | 7/1998 | Zdeblick et al. |
| 5,860,973 A * | 1/1999 | Michelson .................... 606/247 |
| 5,865,845 A | 2/1999 | Thalgott |
| 5,865,848 A | 2/1999 | Baker |
| 5,885,287 A | 3/1999 | Bagby |
| 5,888,223 A | 3/1999 | Bray, Jr. |
| 5,888,224 A | 3/1999 | Beckers et al. |
| 5,888,227 A | 3/1999 | Cottle |
| 5,895,427 A | 4/1999 | Kuslich et al. |
| 5,906,616 A | 5/1999 | Pavlov et al. |
| 5,910,315 A | 6/1999 | Stevenson et al. |
| 5,928,284 A | 7/1999 | Mehdizadeh |
| 5,947,971 A | 9/1999 | Kuslich et al. |
| 5,968,098 A | 10/1999 | Winslow |
| 5,976,187 A | 11/1999 | Richelsoph |
| 5,984,967 A | 11/1999 | Zdeblick et al. |
| 5,989,291 A | 11/1999 | Ralph et al. |
| 6,010,502 A | 1/2000 | Bagby |
| 6,019,792 A | 2/2000 | Cauthen |
| 6,033,438 A | 3/2000 | Bianchi et al. |
| 6,045,579 A | 4/2000 | Hochshuler et al. |
| 6,056,749 A | 5/2000 | Kuslich |
| 6,059,790 A | 5/2000 | Sand et al. |
| 6,074,423 A | 6/2000 | Lawson |
| 6,080,193 A | 6/2000 | Hochshuler et al. |
| 6,090,143 A | 7/2000 | Meriwether et al. |
| 6,096,080 A | 8/2000 | Nicholson et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,123,705 A | 9/2000 | Michelson |
| 6,126,689 A | 10/2000 | Brett |
| 6,129,763 A | 10/2000 | Chauvin et al. |
| 6,143,031 A | 11/2000 | Knothe et al. |
| 6,146,420 A | 11/2000 | McKay |
| RE37,005 E | 12/2000 | Michelson et al. |
| 6,159,244 A | 12/2000 | Suddaby |
| 6,159,245 A | 12/2000 | Meriwether et al. |
| 6,174,334 B1 | 1/2001 | Suddaby |
| 6,176,882 B1 | 1/2001 | Biedermann et al. |
| 6,190,414 B1 | 2/2001 | Young et al. |
| 6,193,756 B1 | 2/2001 | Studer et al. |
| 6,206,922 B1 | 3/2001 | Zdeblick et al. |
| 6,224,631 B1 | 5/2001 | Kohrs |
| 6,235,028 B1 | 5/2001 | Brumfield et al. |
| 6,241,733 B1 | 6/2001 | Nicholson et al. |
| 6,241,769 B1 | 6/2001 | Nicholson et al. |
| 6,241,770 B1 | 6/2001 | Michelson |
| 6,245,072 B1 | 6/2001 | Zdeblick et al. |
| 6,245,108 B1 | 6/2001 | Biscup |
| 6,258,094 B1 | 7/2001 | Nicholson et al. |
| 6,258,125 B1 | 7/2001 | Paul et al. |
| 6,283,968 B1 | 9/2001 | Mehdizadeh |
| 6,296,664 B1 | 10/2001 | Middleton |
| 6,306,170 B2 | 10/2001 | Ray |
| 6,332,894 B1 | 12/2001 | Stalcup et al. |
| 6,332,895 B1 | 12/2001 | Suddaby |
| 6,368,351 B1 | 4/2002 | Glenn et al. |
| 6,371,986 B1 | 4/2002 | Bagby |
| 6,371,987 B1 | 4/2002 | Weiland et al. |
| 6,371,988 B1 | 4/2002 | Pafford et al. |
| 6,371,989 B1 | 4/2002 | Chauvin |
| 6,375,655 B1 | 4/2002 | Zdeblick et al. |
| 6,395,035 B2 | 5/2002 | Bresina et al. |
| 6,409,766 B1 | 6/2002 | Brett |
| 6,419,705 B1 | 7/2002 | Erickson |
| 6,423,063 B1 | 7/2002 | Bonutti |
| 6,425,920 B1 | 7/2002 | Hamada |
| 6,428,542 B1 | 8/2002 | Michelson |
| 6,428,575 B2 | 8/2002 | Koo et al. |
| 6,432,106 B1 | 8/2002 | Fraser |
| 6,432,107 B1 | 8/2002 | Ferree |
| 6,436,139 B1 | 8/2002 | Shapiro et al. |
| 6,436,140 B1 | 8/2002 | Liu et al. |
| 6,440,170 B1 | 8/2002 | Jackson |
| 6,443,989 B1 | 9/2002 | Jackson |
| 6,447,544 B1 | 9/2002 | Michelson |
| 6,447,547 B1 | 9/2002 | Michelson |
| 6,454,805 B1 | 9/2002 | Baccelli et al. |
| 6,454,806 B1 | 9/2002 | Cohen et al. |
| 6,454,807 B1 | 9/2002 | Jackson |
| 6,458,159 B1 | 10/2002 | Thalgott |
| 6,461,359 B1 | 10/2002 | Tribus |
| 6,471,724 B2 | 10/2002 | Zdeblick et al. |
| 6,478,823 B1 | 11/2002 | Michelson |
| 6,482,233 B1 | 11/2002 | Aebi et al. |
| 6,488,710 B2 | 12/2002 | Besselink |
| 6,491,724 B1 | 12/2002 | Ferree |
| 6,500,205 B1 | 12/2002 | Michelson |
| 6,517,580 B1 | 2/2003 | Ramadan et al. |
| 6,527,803 B1 | 3/2003 | Crozet et al. |
| 6,530,926 B1 | 3/2003 | Davison |
| 6,530,929 B1 | 3/2003 | Justis et al. |
| 6,558,424 B2 | 5/2003 | Thalgott |
| 6,562,041 B1 | 5/2003 | Yonemura et al. |
| 6,562,072 B1 | 5/2003 | Fuss et al. |
| 6,562,074 B2 | 5/2003 | Gerbec et al. |
| 6,576,016 B1 | 6/2003 | Hochshuler et al. |
| 6,582,431 B1 | 6/2003 | Ray |
| 6,582,437 B2 | 6/2003 | Dorchak et al. |
| 6,582,467 B1 | 6/2003 | Teitelbaum et al. |
| 6,592,586 B1 | 7/2003 | Michelson |
| 6,599,292 B1 | 7/2003 | Ray |
| 6,610,089 B1 | 8/2003 | Liu et al. |
| 6,613,091 B1 | 9/2003 | Zdeblick et al. |
| 6,616,695 B1 | 9/2003 | Crozet et al. |
| 6,641,614 B1 | 11/2003 | Wagner et al. |
| 6,645,206 B1 | 11/2003 | Zdeblick et al. |
| 6,648,915 B2 | 11/2003 | Sazy |
| 6,652,584 B2 | 11/2003 | Michelson |

(56) References Cited

U.S. PATENT DOCUMENTS

| | | |
|---|---|---|
| 6,660,038 B2 | 12/2003 | Boyer, II et al. |
| 6,666,888 B1 | 12/2003 | Jackson |
| 6,676,703 B2 | 1/2004 | Biscup |
| 6,685,742 B1 | 2/2004 | Jackson |
| 6,699,288 B2 | 3/2004 | Moret |
| 6,709,458 B2 | 3/2004 | Michelson |
| 6,716,247 B2 | 4/2004 | Michelson |
| 6,719,760 B2 | 4/2004 | Dorchak et al. |
| 6,719,794 B2 | 4/2004 | Gerber |
| 6,719,796 B2 | 4/2004 | Cohen et al. |
| 6,723,096 B1 | 4/2004 | Dorchak et al. |
| 6,723,126 B1 | 4/2004 | Berry |
| 6,726,722 B2 | 4/2004 | Walkenhorst et al. |
| 6,730,127 B2 | 5/2004 | Michelson |
| 6,740,093 B2 | 5/2004 | Hochschuler et al. |
| 6,743,255 B2 | 6/2004 | Ferree |
| 6,746,484 B1 | 6/2004 | Liu et al. |
| 6,767,366 B2 | 7/2004 | Lee et al. |
| 6,767,367 B1 | 7/2004 | Michelson |
| 6,770,096 B2 | 8/2004 | Bolger et al. |
| 6,773,460 B2 | 8/2004 | Jackson |
| 6,783,545 B2 | 8/2004 | Castro et al. |
| 6,793,679 B2 | 9/2004 | Michelson |
| RE38,614 E | 10/2004 | Paul et al. |
| 6,800,092 B1 | 10/2004 | Williams et al. |
| 6,800,093 B2 | 10/2004 | Nicholson et al. |
| 6,808,537 B2 | 10/2004 | Michelson |
| 6,814,756 B1 | 11/2004 | Michelson |
| 6,821,298 B1 | 11/2004 | Jackson |
| 6,824,564 B2 | 11/2004 | Crozet |
| 6,830,589 B2 | 12/2004 | Erickson |
| 6,835,206 B2 | 12/2004 | Jackson |
| 6,852,129 B2 | 2/2005 | Gerbec et al. |
| 6,855,166 B2 | 2/2005 | Kohrs |
| 6,855,168 B2 | 2/2005 | Crozet |
| 6,855,169 B2 | 2/2005 | Boyer, II et al. |
| 6,863,673 B2 | 3/2005 | Gerbec et al. |
| 6,890,355 B2 | 5/2005 | Michelson |
| 6,893,464 B2 | 5/2005 | Kiester |
| 6,893,465 B2 | 5/2005 | Huang |
| 6,899,716 B2 | 5/2005 | Cragg |
| 6,899,734 B2 | 5/2005 | Castro |
| 6,902,581 B2 | 6/2005 | Walkenhorst et al. |
| 6,916,320 B2 | 7/2005 | Michelson |
| 6,923,830 B2 | 8/2005 | Michelson |
| 6,926,737 B2 | 8/2005 | Jackson |
| 6,936,050 B2 | 8/2005 | Michelson |
| 6,936,051 B2 | 8/2005 | Michelson |
| 6,942,697 B2 | 9/2005 | Lange et al. |
| 6,942,698 B1 | 9/2005 | Jackson |
| 6,945,933 B2 | 9/2005 | Branch et al. |
| 6,953,477 B2 | 10/2005 | Berry |
| 6,955,691 B2 | 10/2005 | Chae et al. |
| 6,962,606 B2 | 11/2005 | Michelson |
| 6,969,390 B2 | 11/2005 | Michelson |
| 6,972,035 B2 | 12/2005 | Michelson |
| 6,974,480 B2 | 12/2005 | Messerli et al. |
| 7,008,422 B2 | 3/2006 | Foley et al. |
| 7,008,453 B1 | 3/2006 | Michelson |
| 7,014,659 B2 | 3/2006 | Boyer, II et al. |
| 7,018,414 B2 | 3/2006 | Brau et al. |
| 7,018,415 B1 | 3/2006 | McKay |
| 7,018,416 B2 | 3/2006 | Hanson et al. |
| 7,022,138 B2 | 4/2006 | Mashburn |
| 7,029,498 B2 | 4/2006 | Boehm et al. |
| 7,044,971 B2 | 5/2006 | Suddaby |
| 7,044,972 B2 | 5/2006 | Mathys, Jr. et al. |
| 7,056,321 B2 | 6/2006 | Pagliuca et al. |
| 7,060,073 B2 | 6/2006 | Frey et al. |
| 7,060,097 B2 | 6/2006 | Fraser et al. |
| 7,070,621 B2 | 7/2006 | Castro et al. |
| 7,087,058 B2 | 8/2006 | Cragg |
| 7,094,257 B2 | 8/2006 | Mujwid et al. |
| 7,105,023 B2 | 9/2006 | Eckman |
| 7,105,025 B2 | 9/2006 | Castro et al. |
| 7,112,206 B2 | 9/2006 | Michelson |
| 7,112,222 B2 | 9/2006 | Fraser et al. |
| 7,112,224 B2 | 9/2006 | Liu et al. |
| 7,118,598 B2 | 10/2006 | Michelson |
| 7,125,424 B2 | 10/2006 | Banick et al. |
| 7,128,760 B2 | 10/2006 | Michelson |
| 7,128,762 B2 | 10/2006 | Middleton |
| 7,137,997 B2 | 11/2006 | Paul |
| 7,156,874 B2 | 1/2007 | Paponneau et al. |
| 7,156,875 B2 | 1/2007 | Michelson |
| 7,166,129 B2 | 1/2007 | Michelson |
| 7,179,293 B2 | 2/2007 | McKay |
| 7,182,782 B2 | 2/2007 | Kirschman |
| 7,192,446 B2 | 3/2007 | Shapiro et al. |
| 7,192,447 B2 | 3/2007 | Rhoda |
| 7,195,643 B2 | 3/2007 | Jackson |
| 7,201,775 B2 | 4/2007 | Gorensek et al. |
| 7,207,949 B2 | 4/2007 | Miles et al. |
| 7,214,243 B2 | 5/2007 | Taylor |
| 7,217,293 B2 | 5/2007 | Branch, Jr. |
| 7,220,282 B2 | 5/2007 | Kuslich |
| 7,223,292 B2 | 5/2007 | Messerli et al. |
| 7,226,480 B2 | 6/2007 | Thalgott |
| 7,226,483 B2 | 6/2007 | Gerber et al. |
| 7,229,477 B2 | 6/2007 | Biscup |
| 7,232,463 B2 | 6/2007 | Falahee |
| 7,235,105 B2 | 6/2007 | Jackson |
| 7,238,186 B2 | 7/2007 | Zdeblick et al. |
| 7,238,203 B2 | 7/2007 | Bagga et al. |
| 7,238,206 B2 | 7/2007 | Lange et al. |
| 7,285,134 B2 | 10/2007 | Berry et al. |
| 7,285,135 B2 | 10/2007 | McKay et al. |
| 7,303,583 B1 | 12/2007 | Schär et al. |
| 7,303,584 B2 | 12/2007 | Castro et al. |
| 7,316,686 B2 | 1/2008 | Dorchak et al. |
| 7,316,714 B2 | 1/2008 | Gordon et al. |
| 7,326,248 B2 | 2/2008 | Michelson |
| D564,095 S | 3/2008 | Blain |
| 7,361,193 B2 | 4/2008 | Frey et al. |
| 7,384,431 B2 | 6/2008 | Berry |
| 7,396,365 B2 | 7/2008 | Michelson |
| 7,402,176 B2 | 7/2008 | Malek |
| 7,410,501 B2 | 8/2008 | Michelson |
| 7,431,735 B2 | 10/2008 | Liu et al. |
| 7,435,261 B1 | 10/2008 | Castro |
| 7,445,636 B2 | 11/2008 | Michelson |
| 7,455,672 B2 | 11/2008 | Michelson |
| 7,455,692 B2 | 11/2008 | Michelson |
| 7,462,196 B2 | 12/2008 | Fraser |
| 7,465,305 B2 | 12/2008 | Liu et al. |
| 7,470,236 B1 | 12/2008 | Kelleher et al. |
| 7,470,273 B2 | 12/2008 | Dougherty-Shah |
| 7,473,276 B2 | 1/2009 | Aebi et al. |
| 7,473,277 B2 | 1/2009 | Boyer, II et al. |
| 7,476,251 B2 | 1/2009 | Zucherman et al. |
| 7,481,766 B2 | 1/2009 | Lee et al. |
| 7,485,120 B2 | 2/2009 | Ray |
| 7,500,991 B2 | 3/2009 | Bartish, Jr. et al. |
| 7,503,933 B2 | 3/2009 | Michelson |
| 7,509,183 B2 | 3/2009 | Lin et al. |
| 7,534,254 B1 | 5/2009 | Michelson |
| 7,540,882 B2 | 6/2009 | Michelson |
| 7,544,208 B1 | 6/2009 | Mueller et al. |
| 7,569,074 B2 | 8/2009 | Eisermann et al. |
| 7,575,601 B2 | 8/2009 | Dickson |
| 7,582,058 B1 | 9/2009 | Miles et al. |
| 7,588,599 B2 | 9/2009 | Sweeney |
| 7,591,852 B2 | 9/2009 | Prosser |
| 7,594,931 B2 | 9/2009 | Louis et al. |
| 7,608,105 B2 | 10/2009 | Pavlov et al. |
| 7,608,107 B2 | 10/2009 | Michelson |
| 7,618,454 B2 | 11/2009 | Bentley et al. |
| 7,621,938 B2 | 11/2009 | Molz |
| 7,621,950 B1 | 11/2009 | Globerman et al. |
| 7,621,960 B2 | 11/2009 | Boyd et al. |
| 7,637,953 B2 | 12/2009 | Branch et al. |
| 7,641,690 B2 | 1/2010 | Abdou |
| 7,655,010 B2 | 2/2010 | Serhan et al. |
| 7,655,027 B2 | 2/2010 | Michelson |

(56) References Cited

U.S. PATENT DOCUMENTS

| | | | |
|---|---|---|---|
| 7,655,043 B2 | 2/2010 | Peterman et al. |
| 7,655,046 B2 | 2/2010 | Dryer et al. |
| 7,662,186 B2 | 2/2010 | Bagga et al. |
| 7,670,359 B2 | 3/2010 | Yundt |
| 7,674,296 B2 | 3/2010 | Rhoda et al. |
| 7,674,297 B2 | 3/2010 | Falahee |
| 7,678,148 B2 | 3/2010 | Peterman |
| 7,682,394 B2 | 3/2010 | Recoules-Arche et al. |
| 7,695,515 B2 | 4/2010 | Sweeney |
| 7,708,778 B2 | 5/2010 | Gordon et al. |
| 7,713,302 B2 | 5/2010 | Ralph et al. |
| 7,722,674 B1 | 5/2010 | Grotz |
| 7,723,395 B2 | 5/2010 | Ringelsen et al. |
| 7,727,280 B2 | 6/2010 | McLuen |
| 7,731,751 B2 | 6/2010 | Butler et al. |
| 7,749,270 B2 | 7/2010 | Peterman |
| 7,753,958 B2 | 7/2010 | Gordon et al. |
| 7,758,644 B2 | 7/2010 | Trieu |
| 7,763,079 B2 | 7/2010 | McKay |
| 7,771,473 B2 | 8/2010 | Thramann |
| 7,776,093 B2 | 8/2010 | Wolek et al. |
| 7,776,095 B2 | 8/2010 | Peterman et al. |
| 7,780,732 B2 | 8/2010 | Abernathie |
| 7,799,081 B2 | 9/2010 | McKinley |
| 7,803,191 B2 | 9/2010 | Biedermann et al. |
| 7,811,327 B2 | 10/2010 | Hansell et al. |
| 7,819,921 B2 | 10/2010 | Grotz |
| 7,824,427 B2 | 11/2010 | Perez-Cruet et al. |
| 7,824,445 B2 | 11/2010 | Biro et al. |
| 7,828,848 B2 | 11/2010 | Chuvin et al. |
| 7,837,732 B2 | 11/2010 | Zucherman et al. |
| 7,837,735 B2 | 11/2010 | Malone |
| 7,846,210 B2 | 12/2010 | Perez-Cruet |
| 7,850,733 B2 | 12/2010 | Baynham et al. |
| 7,850,734 B2 | 12/2010 | Oh et al. |
| 7,850,736 B2 | 12/2010 | Heinz |
| 7,875,075 B2 | 1/2011 | Schwab |
| 7,875,078 B2 | 1/2011 | Wysocki et al. |
| 7,879,098 B1 | 2/2011 | Simmons, Jr. |
| 7,887,596 B2 | 2/2011 | Douget et al. |
| 7,892,286 B2 | 2/2011 | Michelson |
| 7,914,581 B2 | 3/2011 | Dickson et al. |
| 7,918,891 B1 | 4/2011 | Curran et al. |
| 7,922,729 B2 | 4/2011 | Michelson |
| 7,951,180 B2 | 5/2011 | Moskowitz et al. |
| 7,951,199 B2 | 5/2011 | Miller |
| 7,967,863 B2 | 6/2011 | Frey et al. |
| 7,967,867 B2 | 6/2011 | Barreiro et al. |
| 7,981,156 B2 | 7/2011 | Pafford et al. |
| 7,985,256 B2 | 7/2011 | Grotz et al. |
| 7,985,258 B2 | 7/2011 | Zdeblick et al. |
| 8,002,832 B2 | 8/2011 | Castro |
| 8,002,833 B2 | 8/2011 | Fabris Monterumici et al. |
| 8,007,534 B2 | 8/2011 | Michelson |
| 8,016,887 B1 | 9/2011 | Castro |
| 8,034,110 B2 | 10/2011 | Garner et al. |
| 8,034,111 B2 | 10/2011 | Hsu et al. |
| 8,043,376 B2 | 10/2011 | Falahee |
| 8,043,377 B2 | 10/2011 | Guyer et al. |
| 8,057,548 B2 | 11/2011 | Abernathie et al. |
| 8,062,366 B2 | 11/2011 | Melkent |
| 8,062,368 B2 | 11/2011 | Heinz et al. |
| 8,062,375 B2 | 11/2011 | Glerum et al. |
| 8,070,812 B2 | 12/2011 | Keller |
| 8,070,813 B2 | 12/2011 | Grotz |
| 8,070,816 B2 | 12/2011 | Taylor |
| 8,075,621 B2 | 12/2011 | Michelson |
| 8,083,744 B2 | 12/2011 | Dorchak et al. |
| 8,083,799 B2 | 12/2011 | Baynham et al. |
| 8,088,163 B1 | 1/2012 | Kleiner |
| 8,097,034 B2 | 1/2012 | Michelson |
| 8,100,972 B1 | 1/2012 | Bruffey et al. |
| 8,105,382 B2 | 1/2012 | Olmos et al. |
| 8,110,004 B2 | 2/2012 | Valdevit et al. |
| 8,118,813 B2 | 2/2012 | Perez-Cruet |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,128,700 B2 | 3/2012 | Delurio et al. |
| 8,137,401 B2 | 3/2012 | Stad et al. |
| 8,142,503 B2 | 3/2012 | Malone |
| 8,142,508 B1 | 3/2012 | Bruffey et al. |
| RE43,317 E | 4/2012 | Fraser et al. |
| 8,147,550 B2 | 4/2012 | Gordon et al. |
| 8,147,556 B2 | 4/2012 | Louis et al. |
| 8,152,851 B2 | 4/2012 | Mueller et al. |
| 8,152,852 B2 | 4/2012 | Biyani |
| 8,157,865 B2 | 4/2012 | Hochschuler et al. |
| 8,167,946 B2 | 5/2012 | Michelson |
| 8,172,903 B2 | 5/2012 | Gordon et al. |
| 8,172,905 B2 | 5/2012 | Baynham et al. |
| 8,177,844 B2 | 5/2012 | Tsuang et al. |
| 8,177,848 B2 | 5/2012 | McKay |
| 8,182,535 B2 | 5/2012 | Kraus |
| 8,182,538 B2 | 5/2012 | O'Neil et al. |
| 8,187,304 B2 | 5/2012 | Malek |
| 8,187,331 B2 | 5/2012 | Strohkirch, Jr. et al. |
| 8,187,332 B2 | 5/2012 | McLuen |
| 8,192,357 B2 | 6/2012 | Miles et al. |
| 8,192,495 B2 | 6/2012 | Simpson et al. |
| 8,197,546 B2 | 6/2012 | Doubler et al. |
| 8,221,501 B2 | 7/2012 | Eisermann et al. |
| 8,221,502 B2 | 7/2012 | Branch, Jr. |
| 8,226,718 B2 | 7/2012 | Castro |
| 8,241,294 B2 | 8/2012 | Sommerich et al. |
| 8,241,358 B2 | 8/2012 | Butler et al. |
| 8,241,359 B2 | 8/2012 | Davis et al. |
| 8,241,363 B2 | 8/2012 | Sommerich et al. |
| 8,246,683 B2 | 8/2012 | Castro |
| 8,252,059 B2 | 8/2012 | Overes et al. |
| 8,257,436 B2 | 9/2012 | Jackson |
| 8,257,440 B2 | 9/2012 | Gordon et al. |
| 8,257,442 B2 | 9/2012 | Edie et al. |
| 8,262,737 B2 | 9/2012 | Bagga et al. |
| 8,273,124 B2 | 9/2012 | Renganath et al. |
| 8,273,128 B2 | 9/2012 | Oh et al. |
| 8,277,510 B2 | 10/2012 | Kleiner |
| 8,282,683 B2 | 10/2012 | McLaughlin et al. |
| 8,287,599 B2 | 10/2012 | McGuckin, Jr. |
| 8,292,928 B2 | 10/2012 | Cragg et al. |
| 8,292,958 B1 | 10/2012 | Bruffey et al. |
| 8,292,960 B2 | 10/2012 | Kleiner |
| 8,292,963 B2 | 10/2012 | Miller et al. |
| 8,303,658 B2 | 11/2012 | Peterman |
| 8,303,662 B2 | 11/2012 | Landry et al. |
| 8,303,663 B2 | 11/2012 | Jimenez et al. |
| 8,303,879 B2 | 11/2012 | Bertele et al. |
| 8,308,802 B2 | 11/2012 | Rhoda et al. |
| 8,308,805 B2 | 11/2012 | Lynn et al. |
| 8,323,341 B2 | 12/2012 | Lambrecht et al. |
| 8,323,345 B2 | 12/2012 | Sledge |
| 8,333,804 B1 | 12/2012 | Wensel |
| 8,337,558 B2 | 12/2012 | Lindner |
| 8,337,559 B2 | 12/2012 | Hansell et al. |
| 8,343,224 B2 | 1/2013 | Lynn et al. |
| 8,353,961 B2 | 1/2013 | McClintock et al. |
| 8,361,149 B2 | 1/2013 | Castro |
| 8,361,153 B2 | 1/2013 | Ralph et al. |
| 8,366,774 B1 | 2/2013 | Bruffey et al. |
| 8,372,151 B2 | 2/2013 | Hsu et al. |
| 8,377,132 B2 | 2/2013 | Wing et al. |
| 8,377,139 B2 | 2/2013 | Laubert et al. |
| 8,382,841 B2 | 2/2013 | Yundt |
| 8,382,842 B2 | 2/2013 | Greenhalgh et al. |
| 8,388,667 B2 | 3/2013 | Reiley et al. |
| 8,394,143 B2 | 3/2013 | Grotz et al. |
| 8,398,713 B2 | 3/2013 | Weiman |
| 8,403,990 B2 | 3/2013 | Dryer et al. |
| 8,403,991 B2 | 3/2013 | Ullrich, Jr. et al. |
| 8,409,285 B2 | 4/2013 | Keller |
| 8,409,286 B2 | 4/2013 | McKay |
| 8,409,287 B2 | 4/2013 | Braddock, Jr. et al. |
| 8,409,288 B2 | 4/2013 | Davis et al. |
| 8,414,651 B2 | 4/2013 | Tyber et al. |

(56) References Cited

U.S. PATENT DOCUMENTS

| | | |
|---|---|---|
| 8,419,795 B2 | 4/2013 | Sweeney |
| 8,419,797 B2 | 4/2013 | Biedermann et al. |
| 8,425,612 B2 | 4/2013 | Perez-Cruet et al. |
| 8,430,930 B2 | 4/2013 | Hunt |
| 8,435,296 B2 | 5/2013 | Kadaba et al. |
| 8,435,298 B2 | 5/2013 | Weiman |
| 8,435,299 B2 | 5/2013 | Chauvin et al. |
| 8,435,300 B2 | 5/2013 | Messerli et al. |
| 8,435,302 B2 | 5/2013 | Ulrich, Jr. et al. |
| 8,444,692 B2 | 5/2013 | Michelson |
| 8,449,613 B2 | 5/2013 | Crozet |
| 8,454,695 B2 | 6/2013 | Grotz et al. |
| 8,460,385 B1 | 6/2013 | Wensel |
| 8,475,533 B1 | 7/2013 | Castro |
| 8,480,741 B2 | 7/2013 | Grotz et al. |
| 8,480,745 B2 | 7/2013 | Liu et al. |
| 8,480,748 B2 | 7/2013 | Poulos |
| 8,480,749 B2 | 7/2013 | Ullrich, Jr. et al. |
| 8,486,148 B2 | 7/2013 | Butler et al. |
| 8,486,149 B2 | 7/2013 | Saidha et al. |
| 8,491,653 B2 | 7/2013 | Zucherman et al. |
| 8,491,657 B2 | 7/2013 | Attia et al. |
| 8,491,659 B2 | 7/2013 | Weiman |
| 8,496,706 B2 | 7/2013 | Ragab et al. |
| 8,496,710 B2 | 7/2013 | Bagga et al. |
| RE44,417 E | 8/2013 | Bartish, Jr. et al. |
| 8,506,629 B2 | 8/2013 | Weiland |
| 8,512,407 B2 | 8/2013 | Butler et al. |
| 8,518,120 B2 | 8/2013 | Glerum et al. |
| 8,523,908 B2 | 9/2013 | Malone |
| 8,523,909 B2 | 9/2013 | Hess |
| 8,523,944 B2 | 9/2013 | Jimenez et al. |
| 8,535,380 B2 | 9/2013 | Greenhalgh et al. |
| 8,540,770 B2 | 9/2013 | Woodburn, Sr. |
| 8,545,568 B2 | 10/2013 | Ulrich, Jr. et al. |
| 8,551,176 B2 | 10/2013 | Ullrich, Jr. et al. |
| 8,556,979 B2 | 10/2013 | Glerum et al. |
| 8,562,683 B2 | 10/2013 | McKinley |
| 8,562,684 B2 | 10/2013 | Ullrich, Jr. et al. |
| 8,562,685 B2 | 10/2013 | Ullrich, Jr. et al. |
| 8,568,481 B2 | 10/2013 | Olmos et al. |
| 8,568,482 B2 | 10/2013 | Kraus et al. |
| 8,574,297 B2 | 11/2013 | Stad et al. |
| 8,574,299 B2 | 11/2013 | Barreiro et al. |
| 8,574,300 B2 | 11/2013 | McManus et al. |
| 8,579,976 B2 | 11/2013 | Attia |
| 8,579,979 B2 | 11/2013 | Edie et al. |
| 8,579,983 B2 | 11/2013 | Garner et al. |
| 8,585,761 B2 | 11/2013 | Theofilos |
| 8,585,765 B2 | 11/2013 | Ullrich, Jr. et al. |
| 8,585,766 B2 | 11/2013 | Ullrich, Jr. et al. |
| 8,585,767 B2 | 11/2013 | Ullrich, Jr. et al. |
| 8,591,585 B2 | 11/2013 | McLaughlin et al. |
| 8,591,588 B2 | 11/2013 | Fraser et al. |
| 8,591,590 B2 | 11/2013 | Ullrich, Jr. et al. |
| 8,597,360 B2 | 12/2013 | McLuen et al. |
| 8,603,170 B2 | 12/2013 | Cipoletti et al. |
| 8,603,174 B2 | 12/2013 | Haines |
| 8,617,246 B2 | 12/2013 | Malone |
| 8,617,248 B2 | 12/2013 | Ullrich, Jr. et al. |
| 8,628,575 B2 | 1/2014 | Muhanna et al. |
| 8,628,576 B2 | 1/2014 | Triplett et al. |
| 8,632,595 B2 | 1/2014 | Weiman |
| 8,641,763 B2 | 2/2014 | Yue |
| 8,641,765 B2 | 2/2014 | Muhanna |
| 8,641,769 B2 | 2/2014 | Malandain |
| 8,647,386 B2 | 2/2014 | Gordon et al. |
| 8,663,329 B2 | 3/2014 | Ernst |
| 8,663,330 B2 | 3/2014 | McClintock et al. |
| 8,663,331 B2 | 3/2014 | McClellan, III et al. |
| 8,668,740 B2 | 3/2014 | Rhoda et al. |
| 8,668,741 B2 | 3/2014 | Michelson |
| 8,673,004 B2 | 3/2014 | Michelson |
| 8,673,006 B2 | 3/2014 | Castro |
| 8,673,011 B2 | 3/2014 | Theofilos et al. |
| 8,673,012 B2 | 3/2014 | Smith et al. |
| 8,679,183 B2 | 3/2014 | Glerum |
| 8,679,184 B2 | 3/2014 | Kube, II |
| 8,685,031 B2 | 4/2014 | Kleiner et al. |
| 8,685,095 B2 | 4/2014 | Miller et al. |
| 8,685,098 B2 | 4/2014 | Glerum et al. |
| 8,685,102 B2 | 4/2014 | McKay |
| 8,685,104 B2 | 4/2014 | Lee et al. |
| 8,690,949 B2 | 4/2014 | Messerli et al. |
| 8,696,751 B2 | 4/2014 | Ashley et al. |
| 8,696,752 B2 | 4/2014 | Shih et al. |
| 8,709,042 B2 | 4/2014 | Greenhalgh et al. |
| 8,709,083 B2 | 4/2014 | Duffield et al. |
| 8,709,086 B2 | 4/2014 | Glerum |
| 8,715,351 B1 | 5/2014 | Pinto |
| 8,715,353 B2 | 5/2014 | Bagga et al. |
| 8,715,355 B2 | 5/2014 | Kleiner |
| 8,721,723 B2 | 5/2014 | Hansell et al. |
| 8,728,160 B2 | 5/2014 | Globerman et al. |
| 8,734,447 B1 | 5/2014 | Michaelson |
| 8,734,519 B2 | 5/2014 | de Villiers |
| 8,734,521 B2 | 5/2014 | Freeman et al. |
| 8,734,822 B2 | 5/2014 | Koblish et al. |
| 8,753,398 B2 | 6/2014 | Gordon et al. |
| 8,753,399 B2 | 6/2014 | Sharifi-Mehr |
| 8,771,358 B2 | 7/2014 | Michelson |
| 8,771,360 B2 | 7/2014 | Jimenez et al. |
| 8,771,368 B2 | 7/2014 | McKay |
| 8,778,025 B2 | 7/2014 | Ragab et al. |
| 8,778,027 B2 | 7/2014 | Medina |
| 8,808,305 B2 | 8/2014 | Kleiner |
| 8,808,385 B1 | 8/2014 | Smith et al. |
| 8,834,571 B2 | 9/2014 | Bagga et al. |
| 8,840,620 B2 | 9/2014 | Recoules-Arche et al. |
| 8,840,666 B2 | 9/2014 | Crozet |
| 8,840,669 B2 | 9/2014 | Farris et al. |
| 8,845,733 B2 | 9/2014 | O'Neil et al. |
| 8,852,278 B2 | 10/2014 | Bellasw |
| 9,216,096 B2 | 12/2015 | Lynn et al. |
| 9,380,932 B1 | 7/2016 | Lynn et al. |
| 2001/0001129 A1 | 5/2001 | McKay et al. |
| 2001/0010020 A1 | 7/2001 | Michelson |
| 2001/0047208 A1 | 11/2001 | Michelson |
| 2001/0051829 A1 | 12/2001 | Middleton |
| 2002/0040243 A1 | 4/2002 | Attali et al. |
| 2002/0045945 A1 | 4/2002 | Liu et al. |
| 2002/0049394 A1 | 4/2002 | Roy et al. |
| 2002/0082697 A1 | 6/2002 | Damien |
| 2002/0103540 A1 | 8/2002 | Cooper et al. |
| 2002/0111684 A1 | 8/2002 | Ralph et al. |
| 2002/0111687 A1 | 8/2002 | Ralph et al. |
| 2002/0123750 A1 | 9/2002 | Eisermann et al. |
| 2002/0128652 A1 | 9/2002 | Ferree |
| 2002/0128712 A1 | 9/2002 | Michelson |
| 2002/0138146 A1 | 9/2002 | Jackson |
| 2002/0138147 A1 | 9/2002 | Cohen |
| 2002/0143401 A1 | 10/2002 | Michelson |
| 2002/0161444 A1 | 10/2002 | Choi |
| 2002/0169507 A1 | 11/2002 | Malone |
| 2002/0193880 A1 | 12/2002 | Fraser |
| 2002/0198598 A1 | 12/2002 | Pepper |
| 2003/0069640 A1 | 4/2003 | Ferreira et al. |
| 2003/0083746 A1 | 5/2003 | Kuslich |
| 2003/0083748 A1 | 5/2003 | Lee et al. |
| 2003/0105527 A1 | 6/2003 | Bresina |
| 2003/0114854 A1 | 6/2003 | Pavlov et al. |
| 2003/0114930 A1 | 6/2003 | Lim et al. |
| 2003/0171812 A1 | 9/2003 | Grunberg et al. |
| 2003/0171813 A1 | 9/2003 | Kiester |
| 2003/0181979 A1 | 9/2003 | Ferree |
| 2003/0195520 A1 | 10/2003 | Boyd et al. |
| 2003/0208275 A1 | 11/2003 | Michelson |
| 2004/0034421 A1 | 2/2004 | Errico et al. |
| 2004/0034430 A1 | 2/2004 | Falahee |
| 2004/0059420 A1 | 3/2004 | Michelson |
| 2004/0073314 A1 | 4/2004 | White et al. |
| 2004/0082953 A1 | 4/2004 | Petit |
| 2004/0122424 A1 | 6/2004 | Ferree |
| 2004/0127990 A1 | 7/2004 | Bartish, Jr. et al. |

(56) References Cited

U.S. PATENT DOCUMENTS

| | | |
|---|---|---|
| 2004/0127993 A1 | 7/2004 | Kast et al. |
| 2004/0143330 A1 | 7/2004 | Sazy |
| 2004/0153160 A1 | 8/2004 | Carrasco |
| 2004/0167617 A1 | 8/2004 | Voellmicke |
| 2004/0186483 A1 | 9/2004 | Bagby |
| 2004/0220670 A1 | 11/2004 | Eisermann et al. |
| 2004/0220671 A1 | 11/2004 | Ralph et al. |
| 2004/0249461 A1 | 12/2004 | Ferree |
| 2004/0254643 A1 | 12/2004 | Jackson |
| 2004/0254644 A1 | 12/2004 | Taylor |
| 2005/0027362 A1 | 2/2005 | Williams et al. |
| 2005/0033431 A1 | 2/2005 | Gordon et al. |
| 2005/0033432 A1 | 2/2005 | Gordon et al. |
| 2005/0033439 A1 | 2/2005 | Gordon et al. |
| 2005/0043802 A1 | 2/2005 | Eisermann et al. |
| 2005/0049587 A1 | 3/2005 | Jackson |
| 2005/0049590 A1 | 3/2005 | Alleyne et al. |
| 2005/0065605 A1 | 3/2005 | Jackson |
| 2005/0065611 A1 | 3/2005 | Huppert et al. |
| 2005/0070900 A1 | 3/2005 | Serhan et al. |
| 2005/0080320 A1 | 4/2005 | Lee et al. |
| 2005/0119751 A1 | 6/2005 | Lawson |
| 2005/0119753 A1 | 6/2005 | McGahan et al. |
| 2005/0131548 A1 | 6/2005 | Boyer et al. |
| 2005/0149192 A1 | 7/2005 | Zuckerman et al. |
| 2005/0159816 A1 | 7/2005 | Walkenhorst et al. |
| 2005/0177173 A1 | 8/2005 | Aebi et al. |
| 2005/0177237 A1 | 8/2005 | Shappley et al. |
| 2005/0192669 A1 | 9/2005 | Zdeblick et al. |
| 2005/0209697 A1 | 9/2005 | Paponneau et al. |
| 2005/0216082 A1 | 9/2005 | Wilson et al. |
| 2005/0216089 A1 | 9/2005 | Michelson |
| 2005/0222681 A1 | 10/2005 | Richley et al. |
| 2005/0278027 A1 | 12/2005 | Hyde |
| 2005/0283245 A1 | 12/2005 | Gordon et al. |
| 2005/0283248 A1 | 12/2005 | Gordon et al. |
| 2006/0041314 A1 | 2/2006 | Millard |
| 2006/0047341 A1 | 3/2006 | Trieu |
| 2006/0064170 A1 | 3/2006 | Smith et al. |
| 2006/0084985 A1 | 4/2006 | Kim |
| 2006/0095136 A1 | 5/2006 | McLuen |
| 2006/0116767 A1 | 6/2006 | Magerl et al. |
| 2006/0122701 A1 | 6/2006 | Kiester |
| 2006/0122703 A1 | 6/2006 | Aebi et al. |
| 2006/0129244 A1 | 6/2006 | Ensign |
| 2006/0173543 A1 | 8/2006 | Brau et al. |
| 2006/0190081 A1 | 8/2006 | Kraus et al. |
| 2006/0195192 A1 | 8/2006 | Gordon et al. |
| 2006/0224241 A1 | 10/2006 | Butler et al. |
| 2006/0229729 A1 | 10/2006 | Gordon et al. |
| 2006/0241774 A1 | 10/2006 | Attali et al. |
| 2007/0050029 A1 | 3/2007 | Carrasco |
| 2007/0050030 A1 | 3/2007 | Kim |
| 2007/0055252 A1 | 3/2007 | Blain et al. |
| 2007/0067035 A1 | 3/2007 | Falahee |
| 2007/0073291 A1 | 3/2007 | Cordaro et al. |
| 2007/0073400 A1 | 3/2007 | Paul |
| 2007/0073406 A1 | 3/2007 | Gordon et al. |
| 2007/0118222 A1 | 5/2007 | Lang |
| 2007/0168038 A1 | 7/2007 | Trieu |
| 2007/0168039 A1 | 7/2007 | Trieu |
| 2007/0185580 A1 | 8/2007 | Posel |
| 2007/0191951 A1 | 8/2007 | Branch |
| 2007/0225810 A1 | 9/2007 | Colleran et al. |
| 2007/0233254 A1 | 10/2007 | Grotz et al. |
| 2007/0233263 A1 | 10/2007 | Melkent |
| 2007/0244485 A1 | 10/2007 | Greenhalgh et al. |
| 2007/0260314 A1 | 11/2007 | Biyani |
| 2007/0276377 A1 | 11/2007 | Yundt |
| 2007/0282171 A1 | 12/2007 | Karpowicz et al. |
| 2007/0282443 A1 | 12/2007 | Globerman et al. |
| 2007/0293948 A1 | 12/2007 | Bagga et al. |
| 2007/0293949 A1 | 12/2007 | Salerni et al. |
| 2008/0009792 A1 | 1/2008 | Henniges et al. |
| 2008/0009880 A1 | 1/2008 | Warnick et al. |
| 2008/0015701 A1 | 1/2008 | Garcia et al. |
| 2008/0021462 A1 | 1/2008 | Trieu |
| 2008/0021556 A1 | 1/2008 | Edie |
| 2008/0021559 A1 | 1/2008 | Thramann |
| 2008/0039948 A1 | 2/2008 | Biedermann et al. |
| 2008/0051902 A1 | 2/2008 | Dwyer |
| 2008/0051903 A1 | 2/2008 | Dwyer |
| 2008/0058931 A1 | 3/2008 | White et al. |
| 2008/0065217 A1 | 3/2008 | Hurlbert et al. |
| 2008/0065219 A1 | 3/2008 | Dye et al. |
| 2008/0071284 A1 | 3/2008 | Lechmann et al. |
| 2008/0077247 A1 | 3/2008 | Murillo et al. |
| 2008/0091211 A1 | 4/2008 | Gately |
| 2008/0091270 A1 | 4/2008 | Miller et al. |
| 2008/0097610 A1 | 4/2008 | Guyer et al. |
| 2008/0114454 A1 | 5/2008 | Peterman et al. |
| 2008/0125856 A1 | 5/2008 | Perez-Cruet et al. |
| 2008/0133015 A1 | 6/2008 | Lechmann et al. |
| 2008/0147194 A1 | 6/2008 | Grotz et al. |
| 2008/0154374 A1 | 6/2008 | Labrom |
| 2008/0154377 A1 | 6/2008 | Voellmicke |
| 2008/0161927 A1 | 7/2008 | Savage et al. |
| 2008/0161933 A1 | 7/2008 | Grotz et al. |
| 2008/0172127 A1 | 7/2008 | Perez-Cruet et al. |
| 2008/0172128 A1 | 7/2008 | Perez-Cruet et al. |
| 2008/0177387 A1 | 7/2008 | Parimore et al. |
| 2008/0195209 A1 | 8/2008 | Garcia et al. |
| 2008/0208345 A1 | 8/2008 | Hurlbert et al. |
| 2008/0215093 A1 | 9/2008 | Lin et al. |
| 2008/0221694 A1 | 9/2008 | Warnick et al. |
| 2008/0221695 A1 | 9/2008 | Jacofsky et al. |
| 2008/0243252 A1 | 10/2008 | Hansen et al. |
| 2008/0249622 A1 | 10/2008 | Gray |
| 2008/0249627 A1 | 10/2008 | Moehlenbruck et al. |
| 2008/0262623 A1 | 10/2008 | Bagga et al. |
| 2008/0269901 A1 | 10/2008 | Baynham et al. |
| 2008/0269902 A1 | 10/2008 | Baynham et al. |
| 2008/0281424 A1 | 11/2008 | Parry et al. |
| 2008/0288071 A1 | 11/2008 | Biyani et al. |
| 2008/0288076 A1 | 11/2008 | Soo et al. |
| 2008/0312742 A1 | 12/2008 | Abernathie |
| 2009/0005870 A1 | 1/2009 | Hawkins et al. |
| 2009/0012620 A1 | 1/2009 | Youssef et al. |
| 2009/0024218 A1 | 1/2009 | Frigg et al. |
| 2009/0030519 A1 | 1/2009 | Falahee |
| 2009/0036985 A1 | 2/2009 | Whiting |
| 2009/0043394 A1 | 2/2009 | Zdeblick et al. |
| 2009/0054983 A1 | 2/2009 | Wuisman et al. |
| 2009/0054987 A1 | 2/2009 | Chin et al. |
| 2009/0054991 A1 | 2/2009 | Biyani et al. |
| 2009/0062917 A1 | 3/2009 | Foley et al. |
| 2009/0080997 A1 | 3/2009 | Johnson |
| 2009/0082775 A1 | 3/2009 | Altarac et al. |
| 2009/0088765 A1 | 4/2009 | Butler et al. |
| 2009/0088849 A1 | 4/2009 | Armstrong et al. |
| 2009/0099659 A1 | 4/2009 | Oh et al. |
| 2009/0105830 A1 | 4/2009 | Jones et al. |
| 2009/0105832 A1 | 4/2009 | Allain et al. |
| 2009/0125066 A1 | 5/2009 | Kraus et al. |
| 2009/0132053 A1 | 5/2009 | Sears et al. |
| 2009/0138083 A1 | 5/2009 | Biyani |
| 2009/0138091 A1 | 5/2009 | Ray |
| 2009/0143860 A1 | 6/2009 | Burd et al. |
| 2009/0149957 A1 | 6/2009 | Burd et al. |
| 2009/0157187 A1 | 6/2009 | Richelsoph |
| 2009/0164015 A1 | 6/2009 | Liu et al. |
| 2009/0164017 A1 | 6/2009 | Sommerich et al. |
| 2009/0164018 A1 | 6/2009 | Sommerich et al. |
| 2009/0164019 A1 | 6/2009 | Hsu et al. |
| 2009/0182428 A1 | 7/2009 | McClellan, III et al. |
| 2009/0182430 A1 | 7/2009 | Tyber et al. |
| 2009/0182431 A1 | 7/2009 | Butler et al. |
| 2009/0192613 A1 | 7/2009 | Wing et al. |
| 2009/0198338 A1 | 8/2009 | Phan |
| 2009/0198339 A1* | 8/2009 | Kleiner et al. ............ 623/17.16 |
| 2009/0203969 A1 | 8/2009 | Cohen |
| 2009/0210061 A1 | 8/2009 | Sledge |
| 2009/0210062 A1 | 8/2009 | Thalgott et al. |
| 2009/0216331 A1 | 8/2009 | Grotz et al. |

(56) References Cited

U.S. PATENT DOCUMENTS

| | | |
|---|---|---|
| 2009/0234277 A1 | 9/2009 | Wei et al. |
| 2009/0248163 A1* | 10/2009 | King et al. ................ 623/17.16 |
| 2009/0265007 A1 | 10/2009 | Colleran |
| 2009/0276049 A1 | 11/2009 | Weiland |
| 2009/0299478 A1 | 12/2009 | Carls et al. |
| 2009/0299479 A1 | 12/2009 | Jones et al. |
| 2009/0326657 A1 | 12/2009 | Grinberg et al. |
| 2010/0004747 A1 | 1/2010 | Lin |
| 2010/0010633 A1 | 1/2010 | Kohm |
| 2010/0042219 A1 | 2/2010 | Antonacci et al. |
| 2010/0049325 A1 | 2/2010 | Biedermann et al. |
| 2010/0057207 A1 | 3/2010 | Ray et al. |
| 2010/0063510 A1 | 3/2010 | Arlet et al. |
| 2010/0070036 A1 | 3/2010 | Implicito |
| 2010/0070037 A1 | 3/2010 | Parry et al. |
| 2010/0070041 A1 | 3/2010 | Peterman et al. |
| 2010/0076559 A1 | 3/2010 | Bagga et al. |
| 2010/0087924 A1 | 4/2010 | Arlet |
| 2010/0106250 A1 | 4/2010 | Abdou |
| 2010/0114105 A1 | 5/2010 | Butters et al. |
| 2010/0145455 A1 | 6/2010 | Simpson et al. |
| 2010/0161057 A1 | 6/2010 | Berry et al. |
| 2010/0168798 A1 | 7/2010 | Clineff et al. |
| 2010/0174146 A1 | 7/2010 | Miles et al. |
| 2010/0179594 A1 | 7/2010 | Theofilos et al. |
| 2010/0179658 A1 | 7/2010 | Freeman et al. |
| 2010/0185289 A1 | 7/2010 | Kirwan et al. |
| 2010/0191336 A1 | 7/2010 | Greenhalgh |
| 2010/0204795 A1 | 8/2010 | Greenhalgh |
| 2010/0222884 A1 | 9/2010 | Greenhalgh |
| 2010/0234952 A1 | 9/2010 | Peterman |
| 2010/0241231 A1 | 9/2010 | Marino et al. |
| 2010/0249935 A1 | 9/2010 | Slivka et al. |
| 2010/0268345 A1 | 10/2010 | Ralph et al. |
| 2010/0274358 A1 | 10/2010 | Mueller et al. |
| 2010/0280616 A1 | 11/2010 | Frasier |
| 2010/0286777 A1 | 11/2010 | Errico et al. |
| 2010/0286780 A1 | 11/2010 | Dryer et al. |
| 2010/0298942 A1 | 11/2010 | Ransell et al. |
| 2010/0305707 A1 | 12/2010 | Biedermann et al. |
| 2010/0324684 A1 | 12/2010 | Eisermann et al. |
| 2011/0015742 A1 | 1/2011 | Hong |
| 2011/0015747 A1 | 1/2011 | McManus et al. |
| 2011/0046740 A1 | 2/2011 | Chen et al. |
| 2011/0046743 A1 | 2/2011 | Perez-Cruet et al. |
| 2011/0077741 A1 | 3/2011 | Heinz |
| 2011/0087294 A1 | 4/2011 | Reiley |
| 2011/0093074 A1 | 4/2011 | Glerum et al. |
| 2011/0137420 A1 | 6/2011 | Michelson |
| 2011/0144753 A1 | 6/2011 | Marchek et al. |
| 2011/0153020 A1 | 6/2011 | Abdelgany et al. |
| 2011/0172716 A1 | 7/2011 | Glerum |
| 2011/0172775 A1 | 7/2011 | Flickinger et al. |
| 2011/0184518 A1 | 7/2011 | Trieu |
| 2011/0196495 A1 | 8/2011 | Hunt |
| 2011/0202135 A1 | 8/2011 | Baek et al. |
| 2011/0202137 A1 | 8/2011 | Keith et al. |
| 2011/0208312 A1 | 8/2011 | Moskowitz et al. |
| 2011/0208313 A1 | 8/2011 | Michelson |
| 2011/0218633 A1 | 9/2011 | Frey et al. |
| 2011/0230965 A1 | 9/2011 | Schell et al. |
| 2011/0230968 A1 | 9/2011 | Perisic |
| 2011/0230970 A1* | 9/2011 | Lynn et al. ................ 623/17.16 |
| 2011/0251692 A1 | 10/2011 | McLaughlin et al. |
| 2011/0264219 A1 | 10/2011 | Rouben |
| 2011/0282392 A1 | 11/2011 | Murphy et al. |
| 2011/0282453 A1 | 11/2011 | Greenhalgh et al. |
| 2011/0282454 A1 | 11/2011 | Ullrich et al. |
| 2011/0282457 A1 | 11/2011 | Danièle et al. |
| 2011/0295371 A1 | 12/2011 | Moskowitz et al. |
| 2011/0301709 A1 | 12/2011 | Kraus et al. |
| 2011/0301710 A1 | 12/2011 | Mather et al. |
| 2011/0319995 A1 | 12/2011 | Voellmicke et al. |
| 2011/0319999 A1 | 12/2011 | O'Neil et al. |
| 2011/0320000 A1 | 12/2011 | O'Neil et al. |
| 2012/0004730 A1 | 1/2012 | Castro |
| 2012/0035729 A1 | 2/2012 | Glerum et al. |
| 2012/0059470 A1 | 3/2012 | Weiman |
| 2012/0071981 A1 | 3/2012 | Farley et al. |
| 2012/0071983 A1 | 3/2012 | Ray, III et al. |
| 2012/0078373 A1 | 3/2012 | Gamache et al. |
| 2012/0095559 A1 | 4/2012 | Woods et al. |
| 2012/0109305 A1 | 5/2012 | Park |
| 2012/0109319 A1 | 5/2012 | Perisic |
| 2012/0123546 A1 | 5/2012 | Medina |
| 2012/0123548 A1 | 5/2012 | Lynn et al. |
| 2012/0130496 A1 | 5/2012 | Duffield et al. |
| 2012/0136442 A1 | 5/2012 | Kleiner |
| 2012/0150304 A1 | 6/2012 | Glerum et al. |
| 2012/0150305 A1 | 6/2012 | Glerum et al. |
| 2012/0158143 A1 | 6/2012 | Shapiro |
| 2012/0158144 A1 | 6/2012 | Ullrich, Jr. et al. |
| 2012/0158145 A1 | 6/2012 | Ralph et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0179260 A1 | 7/2012 | Nottingham |
| 2012/0185047 A1 | 7/2012 | Wooley |
| 2012/0191196 A1 | 7/2012 | Louis et al. |
| 2012/0197401 A1 | 8/2012 | Duncan et al. |
| 2012/0215315 A1 | 8/2012 | Hochschuler et al. |
| 2012/0226356 A1 | 9/2012 | Hirschl |
| 2012/0232660 A1 | 9/2012 | Davenport |
| 2012/0245695 A1 | 9/2012 | Simpson et al. |
| 2012/0265307 A1 | 10/2012 | Guyer et al. |
| 2012/0265311 A1 | 10/2012 | Mather et al. |
| 2012/0271424 A1 | 10/2012 | Crawford |
| 2012/0277866 A1 | 11/2012 | Kalluri et al. |
| 2012/0277868 A1 | 11/2012 | Walters |
| 2012/0277869 A1 | 11/2012 | Siccardi et al. |
| 2012/0277878 A1 | 11/2012 | Sommerich et al. |
| 2012/0290090 A1 | 11/2012 | Glerum |
| 2012/0296433 A1 | 11/2012 | Farin |
| 2012/0310349 A1 | 12/2012 | Gordon et al. |
| 2012/0310356 A1 | 12/2012 | Davis et al. |
| 2012/0323327 A1 | 12/2012 | McAfee |
| 2012/0330419 A1 | 12/2012 | Moskowitz et al. |
| 2012/0330421 A1 | 12/2012 | Weiman |
| 2012/0330426 A1 | 12/2012 | McLaughlin et al. |
| 2013/0006360 A1 | 1/2013 | Aferzon et al. |
| 2013/0006361 A1 | 1/2013 | Glerum et al. |
| 2013/0006365 A1 | 1/2013 | Pepper et al. |
| 2013/0018465 A1 | 1/2013 | Yue |
| 2013/0018468 A1 | 1/2013 | Moskowitz et al. |
| 2013/0018469 A1 | 1/2013 | Moskowitz et al. |
| 2013/0018470 A1 | 1/2013 | Moskowitz et al. |
| 2013/0018471 A1 | 1/2013 | Davenport et al. |
| 2013/0023991 A1 | 1/2013 | Moskowitz et al. |
| 2013/0023992 A1 | 1/2013 | Moskowitz et al. |
| 2013/0053893 A1 | 2/2013 | Gamache et al. |
| 2013/0053894 A1 | 2/2013 | Gamache et al. |
| 2013/0053962 A1 | 2/2013 | Moskowitz et al. |
| 2013/0060339 A1 | 3/2013 | Duffield et al. |
| 2013/0073044 A1 | 3/2013 | Gamache |
| 2013/0085572 A1 | 4/2013 | Glerum et al. |
| 2013/0116791 A1 | 5/2013 | Theofilos |
| 2013/0123923 A1 | 5/2013 | Pavlov et al. |
| 2013/0123924 A1 | 5/2013 | Butler et al. |
| 2013/0123935 A1 | 5/2013 | Hunt et al. |
| 2013/0131812 A1 | 5/2013 | Ganey |
| 2013/0138214 A1 | 5/2013 | Greenhalgh et al. |
| 2013/0150967 A1 | 6/2013 | Shih et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0178904 A1 | 7/2013 | Arcenio et al. |
| 2013/0178940 A1 | 7/2013 | Farley |
| 2013/0184822 A1 | 7/2013 | Kleiner |
| 2013/0184826 A1 | 7/2013 | Thaiyananthan |
| 2013/0190880 A1 | 7/2013 | Schaller |
| 2013/0197642 A1 | 8/2013 | Ernst |
| 2013/0197647 A1 | 8/2013 | Wolters et al. |

(56) References Cited

U.S. PATENT DOCUMENTS

| | | |
|---|---|---|
| 2013/0204371 A1 | 8/2013 | McLuen et al. |
| 2013/0204373 A1 | 8/2013 | Lambrecht et al. |
| 2013/0204374 A1 | 8/2013 | Milella |
| 2013/0211525 A1 | 8/2013 | McLuen et al. |
| 2013/0218275 A1 | 8/2013 | Caballes |
| 2013/0245763 A1 | 9/2013 | Mauldin |
| 2013/0245765 A1 | 9/2013 | Lowry et al. |
| 2013/0247357 A1 | 9/2013 | Bertele et al. |
| 2013/0253650 A1 | 9/2013 | Ashley et al. |
| 2013/0261748 A1 | 10/2013 | Ashley et al. |
| 2013/0268079 A1 | 10/2013 | Castro |
| 2013/0274883 A1 | 10/2013 | McLuen et al. |
| 2013/0274890 A1 | 10/2013 | McKay |
| 2013/0282126 A1 | 10/2013 | Saidha et al. |
| 2013/0304213 A1 | 11/2013 | Aflatoon et al. |
| 2013/0310940 A1 | 11/2013 | Chauvin et al. |
| 2013/0317615 A1 | 11/2013 | Jimenez et al. |
| 2013/0345813 A1 | 12/2013 | Frank et al. |
| 2013/0345814 A1 | 12/2013 | Walkenhorst et al. |
| 2014/0012383 A1 | 1/2014 | Triplett et al. |
| 2014/0018921 A1 | 1/2014 | Stad et al. |
| 2014/0018922 A1 | 1/2014 | Marino et al. |
| 2014/0018924 A1 | 1/2014 | McManus et al. |
| 2014/0031936 A1 | 1/2014 | Weiman |
| 2014/0031942 A1 | 1/2014 | Ullrich et al. |
| 2014/0039622 A1 | 2/2014 | Glerum et al. |
| 2014/0039627 A1 | 2/2014 | Weiland |
| 2014/0046373 A1 | 2/2014 | Brennan |
| 2014/0046445 A1 | 2/2014 | Brennan |
| 2014/0052252 A1 | 2/2014 | Weiman |
| 2014/0052253 A1 | 2/2014 | Perlott et al. |
| 2014/0052254 A1 | 2/2014 | Glerum et al. |
| 2014/0052258 A1 | 2/2014 | Ball et al. |
| 2014/0052259 A1 | 2/2014 | Garner et al. |
| 2014/0052260 A1 | 2/2014 | McKenny et al. |
| 2014/0058446 A1 | 2/2014 | Bernstein |
| 2014/0058512 A1 | 2/2014 | Petersheim |
| 2014/0058513 A1 | 2/2014 | Gahman et al. |
| 2014/0058514 A1 | 2/2014 | Berry et al. |
| 2014/0058515 A1 | 2/2014 | Hawkins et al. |
| 2014/0058516 A1 | 2/2014 | Glerum et al. |
| 2014/0058518 A1 | 2/2014 | Niemiec et al. |
| 2014/0058519 A1 | 2/2014 | Glerum et al. |
| 2014/0058520 A1 | 2/2014 | Crozet |
| 2014/0058521 A1 | 2/2014 | McLuen et al. |
| 2014/0058522 A1 | 2/2014 | Rhoda |
| 2014/0067071 A1 | 3/2014 | Weiman et al. |
| 2014/0074241 A1 | 3/2014 | McConnell |
| 2014/0088708 A1 | 3/2014 | Mclaughlin et al. |
| 2014/0088710 A1 | 3/2014 | Etminan |
| 2014/0088711 A1 | 3/2014 | Chin et al. |
| 2014/0088715 A1 | 3/2014 | Ciupik |
| 2014/0094916 A1 | 4/2014 | Glerum |
| 2014/0094917 A1 | 4/2014 | Salerni |
| 2014/0094918 A1* | 4/2014 | Vishnubholta et al. ... 623/17.16 |
| 2014/0094922 A1 | 4/2014 | Abdou |
| 2014/0100657 A1 | 4/2014 | McCormack et al. |
| 2014/0107785 A1 | 4/2014 | Geisler et al. |
| 2014/0107786 A1 | 4/2014 | Geiser et al. |
| 2014/0114134 A1 | 4/2014 | Theofilos et al. |
| 2014/0114417 A1 | 4/2014 | Theofilos et al. |
| 2014/0114420 A1 | 4/2014 | Robinson |
| 2014/0114421 A1 | 4/2014 | Ullrich et al. |
| 2014/0114422 A1 | 4/2014 | Malandain |
| 2014/0121773 A1 | 5/2014 | Patel et al. |
| 2014/0121774 A1 | 5/2014 | Glerum et al. |
| 2014/0121777 A1 | 5/2014 | Rosen et al. |
| 2014/0128977 A1 | 5/2014 | Glerum et al. |
| 2014/0135930 A1 | 5/2014 | Georges |
| 2014/0135932 A1 | 5/2014 | Davis et al. |
| 2014/0135933 A1 | 5/2014 | McClintock et al. |
| 2014/0142701 A1 | 5/2014 | Weiman |
| 2014/0142704 A1 | 5/2014 | Ralph et al. |
| 2014/0142709 A1 | 5/2014 | Kube, II |
| 2014/0148904 A1 | 5/2014 | Robinson |
| 2014/0156007 A1 | 6/2014 | Pabst et al. |
| 2014/0156008 A1 | 6/2014 | Flickinger et al. |
| 2014/0163686 A1 | 6/2014 | Frasier et al. |
| 2014/0172103 A1 | 6/2014 | O'Neil et al. |
| 2014/0172106 A1 | 6/2014 | To et al. |
| 2014/0180419 A1 | 6/2014 | Dmuschewsky |
| 2014/0188225 A1 | 7/2014 | Dmuschewsky |
| 2014/0188228 A1 | 7/2014 | Thibodeau |
| 2014/0194991 A1 | 7/2014 | Jimenez |
| 2014/0194992 A1 | 7/2014 | Medina |
| 2014/0200669 A1 | 7/2014 | Berger et al. |
| 2014/0207235 A1 | 7/2014 | Drapeau |
| 2014/0207238 A1 | 7/2014 | Theofilis et al. |
| 2014/0222151 A1 | 8/2014 | Refai et al. |
| 2014/0228955 A1 | 8/2014 | Weiman |
| 2014/0236296 A1 | 8/2014 | Wagner et al. |
| 2014/0236297 A1 | 8/2014 | Iott et al. |
| 2014/0236298 A1 | 8/2014 | Pinto |
| 2014/0243983 A1 | 8/2014 | Galea et al. |
| 2014/0249589 A1 | 9/2014 | Reiley et al. |
| 2014/0249628 A1 | 9/2014 | Weiman |
| 2014/0249629 A1 | 9/2014 | Moskowitz et al. |
| 2014/0257484 A1 | 9/2014 | Flower et al. |
| 2014/0257485 A1 | 9/2014 | Matthis et al. |
| 2014/0257486 A1 | 9/2014 | Alheidt |
| 2014/0277139 A1 | 9/2014 | Vrionis et al. |
| 2014/0277464 A1 | 9/2014 | Richter et al. |
| 2014/0277471 A1 | 9/2014 | Gray et al. |
| 2014/0277472 A1 | 9/2014 | Gray et al. |
| 2014/0277473 A1 | 9/2014 | Perrow |
| 2014/0277474 A1 | 9/2014 | Robinson et al. |
| 2014/0277475 A1 | 9/2014 | De Villiers et al. |
| 2014/0277484 A1 | 9/2014 | Prevost et al. |
| 2014/0277497 A1 | 9/2014 | Bennett et al. |
| 2014/0277498 A1 | 9/2014 | Ainsworth et al. |
| 2014/0277499 A1 | 9/2014 | Ainsworth et al. |
| 2014/0277508 A1 | 9/2014 | Baynham |
| 2014/0288652 A1 | 9/2014 | Boehm et al. |
| 2014/0296982 A1 | 10/2014 | Cheng |
| 2014/0296983 A1 | 10/2014 | Fauth et al. |
| 2014/0296984 A1 | 10/2014 | Etminan |
| 2014/0303731 A1 | 10/2014 | Glerum |
| 2015/0045892 A1 | 2/2015 | Lynn et al. |
| 2015/0148908 A1 | 5/2015 | Marino et al. |
| 2015/0265420 A1 | 9/2015 | Lynn et al. |
| 2016/0030188 A1 | 2/2016 | Lynn et al. |

FOREIGN PATENT DOCUMENTS

| | | |
|---|---|---|
| EP | 646366 B1 | 12/1997 |
| EP | 834295 A1 | 4/1998 |
| EP | 369603 B1 | 5/1998 |
| EP | 498816 B1 | 11/1998 |
| EP | 966929 A2 | 12/1999 |
| EP | 760639 B1 | 4/2000 |
| EP | 1043002 A2 | 10/2000 |
| EP | 1082950 A1 | 3/2001 |
| EP | 857041 B1 | 4/2001 |
| EP | 1099429 A1 | 5/2001 |
| EP | 844856 B1 | 10/2001 |
| EP | 1138285 A1 | 10/2001 |
| EP | 871419 B1 | 11/2001 |
| EP | 720455 B1 | 1/2002 |
| EP | 734703 B1 | 2/2002 |
| EP | 781113 B1 | 3/2002 |
| EP | 716840 B1 | 5/2002 |
| EP | 784967 B1 | 11/2002 |
| EP | 1175878 B1 | 3/2003 |
| EP | 1147751 B1 | 5/2003 |
| EP | 1328217 A2 | 7/2003 |
| EP | 855887 B1 | 8/2003 |
| EP | 1006955 B1 | 8/2003 |
| EP | 977526 B1 | 9/2003 |
| EP | 831759 B1 | 3/2004 |
| EP | 1014899 B1 | 8/2004 |
| EP | 1033941 B1 | 8/2004 |
| EP | 1132061 B1 | 8/2004 |
| EP | 1063949 B1 | 9/2004 |
| EP | 1011481 B1 | 10/2004 |

(56) References Cited

FOREIGN PATENT DOCUMENTS

| | | | |
|---|---|---|---|
| EP | 1051133 | B1 | 10/2004 |
| EP | 1107711 | B1 | 10/2004 |
| EP | 1272130 | B1 | 11/2004 |
| EP | 888099 | B1 | 1/2005 |
| EP | 1278486 | B1 | 3/2005 |
| EP | 836454 | B1 | 4/2005 |
| EP | 1255516 | B1 | 4/2005 |
| EP | 1364617 | B1 | 8/2005 |
| EP | 1124511 | B1 | 9/2005 |
| EP | 1139930 | B1 | 9/2005 |
| EP | 1350489 | B1 | 10/2005 |
| EP | 853932 | B1 | 11/2005 |
| EP | 1076536 | B1 | 11/2005 |
| EP | 891169 | B1 | 12/2005 |
| EP | 1164979 | B1 | 12/2005 |
| EP | 1233732 | B1 | 5/2006 |
| EP | 1280481 | B1 | 7/2006 |
| EP | 1189557 | B1 | 8/2006 |
| EP | 1211985 | B1 | 9/2006 |
| EP | 1009338 | B1 | 10/2006 |
| EP | 1481654 | B1 | 10/2006 |
| EP | 1351610 | B1 | 12/2006 |
| EP | 1374806 | B1 | 12/2006 |
| EP | 1138267 | B1 | 3/2007 |
| EP | 1504732 | B1 | 5/2007 |
| EP | 1009337 | B1 | 6/2007 |
| EP | 1023010 | B1 | 6/2007 |
| EP | 1284689 | B1 | 6/2007 |
| EP | 1532949 | B1 | 7/2007 |
| EP | 1464307 | B1 | 8/2007 |
| EP | 1585466 | B1 | 8/2007 |
| EP | 1698305 | B1 | 8/2007 |
| EP | 1148849 | B1 | 12/2007 |
| EP | 1523963 | B1 | 12/2007 |
| EP | 1554995 | B1 | 12/2007 |
| EP | 1504735 | B1 | 1/2008 |
| EP | 1123069 | B1 | 2/2008 |
| EP | 1330188 | B1 | 2/2008 |
| EP | 1290985 | B1 | 4/2008 |
| EP | 1391189 | B1 | 6/2008 |
| EP | 1567096 | B1 | 7/2008 |
| EP | 1194087 | B1 | 8/2008 |
| EP | 1437105 | B1 | 10/2008 |
| EP | 1139936 | B1 | 12/2008 |
| EP | 1389978 | B1 | 1/2009 |
| EP | 1011503 | B1 | 4/2009 |
| EP | 1341491 | B1 | 4/2009 |
| EP | 1469800 | B1 | 4/2009 |
| EP | 1925271 | B1 | 8/2009 |
| EP | 1506753 | B1 | 9/2009 |
| EP | 1554994 | B1 | 9/2009 |
| EP | 1645248 | B1 | 9/2009 |
| EP | 1829503 | B1 | 9/2009 |
| EP | 1011545 | B1 | 12/2009 |
| EP | 1841385 | B1 | 3/2010 |
| EP | 1843723 | B1 | 3/2010 |
| EP | 1408889 | B1 | 6/2010 |
| EP | 1774926 | B1 | 6/2010 |
| EP | 2111823 | B1 | 8/2010 |
| EP | 1706075 | B1 | 1/2011 |
| EP | 1762202 | B1 | 1/2011 |
| EP | 1301149 | B1 | 2/2011 |
| EP | 1903994 | B1 | 2/2011 |
| EP | 1372541 | B1 | 3/2011 |
| EP | 1321115 | B1 | 7/2011 |
| EP | 1400221 | B1 | 9/2011 |
| EP | 2108340 | B1 | 9/2011 |
| EP | 2368528 | A1 | 9/2011 |
| EP | 1385457 | B1 | 10/2011 |
| EP | 1732480 | B1 | 2/2012 |
| EP | 2157938 | B1 | 2/2012 |
| EP | 2327377 | B1 | 3/2012 |
| EP | 1478309 | B1 | 4/2012 |
| EP | 1699389 | B1 | 4/2012 |
| EP | 2018827 | B1 | 5/2012 |
| EP | 2234564 | B1 | 5/2012 |
| EP | 2237748 | B1 | 9/2012 |
| EP | 2194929 | B1 | 10/2012 |
| EP | 1430858 | B1 | 11/2012 |
| EP | 1463465 | B1 | 11/2012 |
| EP | 2340776 | B1 | 1/2013 |
| EP | 1838248 | B1 | 3/2013 |
| EP | 2055267 | B1 | 4/2013 |
| EP | 2361572 | B1 | 4/2013 |
| EP | 1198208 | B1 | 7/2013 |
| EP | 2632391 | A1 | 9/2013 |
| EP | 2249747 | B1 | 12/2013 |
| EP | 2083760 | B1 | 1/2014 |
| EP | 2677971 | A2 | 1/2014 |
| EP | 2065016 | B1 | 4/2014 |
| EP | 2376026 | B1 | 4/2014 |
| EP | 2729091 | A1 | 5/2014 |
| EP | 2142147 | B1 | 7/2014 |
| EP | 2207504 | B1 | 7/2014 |
| EP | 2376030 | B1 | 8/2014 |
| EP | 2760376 | A1 | 8/2014 |
| EP | 2764851 | A1 | 8/2014 |
| EP | 2777633 | A2 | 9/2014 |
| EP | 2779953 | A2 | 9/2014 |
| FR | 2 841 124 | | 12/2003 |
| WO | WO9614809 | A1 | 5/1996 |
| WO | WO9622747 | A1 | 8/1996 |
| WO | WO9723174 | A1 | 7/1997 |
| WO | WO 97/32547 | | 9/1997 |
| WO | WO 97/37619 | | 10/1997 |
| WO | WO9842269 | A1 | 10/1998 |
| WO | WO0209597 | A2 | 2/2002 |
| WO | WO2004000176 | A1 | 12/2003 |
| WO | WO2006134262 | A1 | 12/2006 |
| WO | WO2008044057 | A1 | 4/2008 |
| WO | WO2008112607 | A2 | 9/2008 |
| WO | WO2008152499 | A2 | 12/2008 |
| WO | WO2009040840 | A1 | 4/2009 |
| WO | WO2009064787 | A2 | 5/2009 |
| WO | WO2009091775 | A2 | 7/2009 |
| WO | WO2010148112 | A1 | 12/2010 |
| WO | WO2011056172 | A1 | 5/2011 |
| WO | WO2011116136 | | 9/2011 |
| WO | WO2011142761 | A1 | 11/2011 |
| WO | WO2012056119 | A1 | 5/2012 |
| WO | WO2012117312 | A2 | 9/2012 |
| WO | WO2013007888 | A1 | 1/2013 |
| WO | WO2013008111 | A1 | 1/2013 |
| WO | WO2013048000 | A2 | 4/2013 |
| WO | WO2013142480 | A1 | 9/2013 |
| WO | WO2013158294 | A1 | 10/2013 |
| WO | WO2013175147 | A1 | 11/2013 |
| WO | WO2013184946 | A1 | 12/2013 |
| WO | WO2014035835 | A1 | 3/2014 |
| WO | WO2014063255 | A1 | 5/2014 |
| WO | WO2014118291 | A1 | 8/2014 |
| WO | WO2014144696 | A1 | 9/2014 |
| WO | WO2014158619 | A1 | 10/2014 |
| WO | WO2014159739 | A1 | 10/2014 |
| WO | WO2014159762 | A1 | 10/2014 |

OTHER PUBLICATIONS

Butterman et al., *Interbody device endplate engagement effects on motion segment biomechanics*, The Spine Journal, 9(7):pp. 564-573, Jul. 2009.

Product information in 1 page for an implant named *Cross-Fuse® Lateral Option System* by Pioneer Surgical Technology, Inc. (dated 2011 and retrieved on or about Aug. 2012 from www.pioneersurgical.com/international/index.php?option=com_content&view=article&id=72&Itemid=72).

Product information in 1 page for an implant named *TransContinental® Spacer System* by Globus Medical, Inc. (retrieved on or about Aug. 2012 from www.globusmedical.com/intervertebral-fusion/220-transcontinental).

Product information in 1 page for an implant named *CoRoent® Interbody/VBR Implant* by NuVasive, Inc. (retrieved on or about

(56) References Cited

OTHER PUBLICATIONS

Aug. 2012 as a partial image (screenshot) capture from www.nuvasive.com/health-providers/innovative-solutions/).

Wright, N.M., MD, *Biomechanical Testing of XLIF Constructs—Stand-Alone Interbody Versus Interbody Supplemented with Lateral or Posterior Instrumentation*, Digital Poster presented at the Congress of Neurological Surgeons (CNS) Annual Conference 2005 in Boston, Massachusetts (Oct. 8, 2005-Oct. 13, 2005), which illustrates and discusses, inter alia, an implant named *CoRoent* by NuVasive, Inc.

DeWald, R.L., "Spinal Deformities: The Comprehensive Text," (partial excerpt from book), published Mar. 15, 2003.

* cited by examiner

SPINAL IMPLANT

PRIORITY DATA

This application is a continuation application of U.S. application Ser. No. 13/049,693, filed Mar. 16, 2011, which claims the priority benefit under 35 U.S.C. §119(e) of U.S. Provisional Application No. 61/314,509, filed Mar. 16, 2010, and U.S. Provisional Application No. 61/389,671, filed Oct. 4, 2010. The entire contents of all of the foregoing applications are hereby incorporated by reference herein.

BACKGROUND

Field

This application generally relates to spinal fusion, and more specifically, to spinal implants and related systems, tools and methods.

Description of the Related Art

Intervertebral discs can degenerate or otherwise become damaged over time. In some instances, an intervertebral implant can be positioned within a space previously occupied by a disc. Such implants can help maintain a desired spacing between adjacent vertebrae and/or promote fusion between adjacent vertebrae. The use of bone graft and/or other materials within spinal implants can facilitate the fusion of adjacent vertebral bodies. Accordingly, a need exists for an improved intervertebral implant, as well as related instrumentation, tools, systems and methods.

SUMMARY

According to some embodiments, a spinal implant configured for placement within an intervertebral space of a patient comprises an anterior wall, a posterior wall, a first lateral wall and a second lateral wall, such that the first and second lateral walls generally extend between the anterior wall and the posterior wall. The spinal implant additionally comprises at least one internal chamber defined, at least in part, by the anterior wall, the posterior wall and the first and second lateral walls. In some embodiments, the implant comprises a top surface having a plurality of teeth configured to at least partially engage a lower surface of a first vertebral body and/or a bottom surface comprising a plurality of teeth configured to at least partially engage an upper surface of a second vertebral body, the second vertebral body being adjacent to said first vertebral body. In some embodiments, the at least one internal chamber extends at least partially from the top surface to the bottom surface of the implant. The implant further comprises at least one opening extending through the anterior wall, wherein such an opening is in fluid communication with the internal chamber. In some embodiments, the spinal implant additionally comprises at least one access port located in the anterior wall, the first lateral wall and/or the second lateral wall. In some embodiments, the implant is configured to releasably secure to an insertion tool using the access port. In some embodiments, the implant is configured to span across an entire width or substantially an entire width of the adjacent vertebral bodies. In one embodiment, the access port is configured to receive at least one graft material delivered into the at least one internal chamber. In some embodiments, the posterior wall does not comprise any openings.

According to some embodiments, excess graft material delivered into the at least one internal chamber through the access port is configured to exit the implant through one or more openings of the anterior wall. In one embodiment, the access port is threaded, so that a delivery tool comprising a corresponding thread pattern can be selectively attached and detached to the spinal implant. In some embodiments, the implant comprises one or more recesses and/or other features configured to mate with corresponding flanges or other protruding members of an implant delivery tool. In one embodiment, each of the first and second lateral walls is configured to generally align with peripheral bearing areas of the adjacent vertebral members. In other embodiments, the teeth along the top and/or bottom surfaces of the implant are configured to slant toward a lateral center of the implant. In some embodiments, the slanted teeth help retain the implant within the target intervertebral space after implantation and/or help reduce the likelihood the migration of grafting materials out of the at least one internal chamber of the implant along the top and bottom surfaces of the implant.

According to some embodiments, the first lateral wall and/or the second lateral wall comprises a tapered portion to facilitate insertion of the implant into the intervertebral space. In one embodiment, the spinal implant further comprises a plurality of prongs that extend into the internal chamber for retaining a graft or other member positioned therein. In some embodiments, such prongs are configured to retain at least one of a sponge, a porous foam and cured grafting materials within the at least one internal chamber of the implant. In some embodiments, the implant is configured for placement within a lumbar or thoracic portion of a patient's spine. In some embodiments, the implant is configured for lateral or anterior insertion into the intervertebral space. In several embodiments, the implant comprises polyether etherketone (PEEK) and/or any other material.

According to some embodiments, the length of each of the first and second lateral walls is approximately 10% to 20% of an overall length of the implant. In other embodiments, the length of each of the first and second lateral walls is less than about 10% or greater than about 20% of an overall length of the implant. In one embodiment, the teeth along at least one of the top and/or bottom surfaces of the implant are oriented, at least in part, in a concentric manner. In one embodiment, a radius of curvature of the teeth along at least one of the top and bottom surfaces of the implant increases with increasing distance from a center of the implant. In some arrangements, the top and/or bottom surfaces of the implant are generally planar. In other embodiments, the top and/or bottom surfaces of the implant are generally curved, fluted, rounded and/or non-planar.

According to some embodiments, the implant comprises a lordotic implant, such that a height of the first lateral wall is greater than a height of the second lateral wall. In some embodiments, the internal chamber does not comprise any interior walls or baffles. In alternative embodiments, the internal chamber comprises at least two internal sub-chambers divided by at least one interior wall or baffle. In one embodiment, the implant comprises at least one radio-opaque marker. In several embodiments, the access port is generally circular. In other embodiments, the access port is non-circular (e.g., square, other rectangular or polygonal, oval, elliptical, irregular, etc.).

According to some embodiments, the access port comprises a minimum diameter of approximately 6 mm. In other embodiments, the diameter or other cross-sectional dimension of the access port is greater or less than about 6 mm (e.g., 4 mm, 5 mm, 7 mm, 8 mm, etc.). In some embodiments, the access port is adapted to receive a fill tube, catheter or other conduit therethrough, wherein such fill tube, catheter or other conduit is configured to selectively deliver a grafting or fill material into the internal chamber of the implant. In some embodiments, a ratio of a diameter of the at least one access port to a height of the first or second lateral wall through which the at least one access port is located is between approximately 0.4 and 0.8 (e.g., about 0.4, 0.45, 0.5, 0.55, 0.6, 0.65, 0.7, 0.75, 0.8, 0.85, 0.9, etc.). In one embodiment, a minimum ratio of a diameter of the at least one access port to a height of the first or second lateral wall through which the at least one access port is located is approximately 0.5, 0.6, 0.7 or 0.8.

According to some embodiments, the access port comprises a valve or other flow blocking device or feature to help retain grafting materials within the at least one internal chamber of the implant. In some embodiments, an exterior profile of the anterior wall is generally curved. In some arrangements, an exterior profile of the posterior wall is generally planar.

According to some embodiments, a method for promoting spinal fusion comprises providing a spinal implant (e.g., such as one of the implants disclosed herein or equivalents thereof) and positioning the spinal implant between two adjacent vertebral bodies or vertebrae of a patient. The method further comprises directing at least one graft material into the internal chamber of the spinal implant through a port of the implant. In some embodiments, at least a portion of the graft and/or other filler material (e.g., materials in excess of the capacity of the implant) delivered into the at least one internal chamber is configured to exit through one or more openings of the anterior wall when a sufficient amount of the at least one graft material has been delivered into the at least one internal chamber.

According to some embodiments, positioning the spinal implant between two adjacent vertebrae comprises removably securing the spinal implant to the distal end of an insertion tool assembly, wherein the insertion tool assembly is secured to, at least in part, to the access port of the spinal implant. In some embodiments, the access port is used to both secure the implant to an implant delivery tool and to deliver grafting and/or other materials to the inside of the implant. In some embodiments, directing graft and/or other materials into the internal chamber comprises passing such materials through a cannulated portion of the insertion tool assembly. In other embodiments, directing the material into the internal chamber comprises passing the materials through a separate conduit adapted to be removably positioned within the access port of the spinal implant. In one embodiment, directing the graft and/or other materials into the internal chamber comprises injecting such materials through tubing using a syringe.

According to some embodiments, the tubing is routed through an internal passage of a fill tube assembly, wherein fill tube assembly is configured to engage at least a portion of the spinal implant while the graft and/or other materials are directed into the internal chamber of the implant. In some embodiments, at least a portion of the graft material delivered into the internal chamber is configured to exit through an interface between the upper and/or lower surface of the implant and the adjacent endplate surfaces of the vertebral bodies. In some embodiments, at least a portion of the internal chamber comprises a graft material prior to positioning the spinal implant between the two adjacent vertebrae. In some embodiments, an additional volume of a graft material is delivered into the internal chamber of the implant after the spinal implant has been secured between the two adjacent vertebrae.

According to some embodiments, the method further includes preparing at least one adjacent vertebral body surface for the delivery of the spinal implant, wherein preparing an adjacent vertebral body surface comprises abrading said surface using a rasping and/or other abrading or roughening tool. In some embodiments, such tools comprise one or more roughened surfaces or features configured to abrade bone and/or other tissue. In some embodiments, the method additionally comprises placing a sizing tool within a target intervertebral space prior to positioning the spinal implant between two adjacent vertebrae of a patient in order to determine the appropriate size of said spinal implant. In some embodiments, the sizing tool is configured to distract the adjacent vertebrae by a desired distance.

According to some embodiments, a kit includes a spinal implant (e.g., such as any of those disclosed herein or equivalents thereof), an implant delivery tool configured to removably secure to the spinal implant and a graft material delivery system configured to selectively deliver at least one graft and/or other filler material into an interior (e.g., internal chamber) of the spinal implant. In some arrangements, the graft material delivery system comprises a syringe, a sizing tool and a conduit configured to pass through the at least one access port of the spinal implant.

According to some embodiments, a method for promoting spinal fusion using a spinal implant comprises providing a spinal implant, wherein the spinal implant comprises an anterior wall, a posterior wall and two lateral walls configured to extend between the anterior wall and the posterior wall. In some embodiments, the spinal implant further comprises at least one internal chamber generally positioned between the anterior wall, the posterior wall and the two lateral walls, wherein the internal chamber being is adapted to receive at least one graft and/or other fill material. In some arrangements, the anterior wall of the spinal implant comprises at least one opening or hole that places the internal chamber in fluid communication with an exterior area or portion of the spinal implant. In one embodiment, at least one of the two lateral walls comprises an access port. The method additionally includes positioning the spinal implant between two adjacent vertebrae of a patient and directing at least one graft and/or other fill material into the internal chamber of the spinal implant through the access port. In some embodiments, at least a portion of the graft and/or other fill material delivered into the internal chamber is configured to exit through the one or more of the openings of the anterior wall.

In some embodiments, positioning the spinal implant between two adjacent vertebrae comprises removably securing the spinal implant to the distal end of an insertion tool assembly, wherein the insertion tool assembly is secured to, at least in part, to the access port of the spinal implant. In one embodiment, directing the graft material into the internal chamber comprises passing the graft material through a cannulated portion of the insertion tool assembly. In some embodiments, directing the graft material into the internal chamber comprises injecting one or more graft materials through flexible tubing using a syringe. In some embodiments, the flexible tubing is routed through an internal passage of a fill tube assembly, wherein the fill tube assembly is configured to engage at least a portion of the spinal implant while the graft material is being directed into the internal chamber. In some arrangements, at least a portion of the graft and/or other fill material delivered into the internal chamber is configured to exit through an interface between the upper surface and/or lower surface of the spinal implant and an adjacent endplate surface of a vertebral body. In one embodiment, at least a portion of the internal chamber comprises a graft material prior to positioning the spinal implant between the two adjacent vertebrae. In some embodiments, such a pre-loaded graft material or item comprises a graft, an absorbent sponge or other member and or the like.

According to some embodiments, an implant configured for placement within an intervertebral space of a patient comprises an anterior wall, a posterior wall, a first lateral wall and a second lateral wall, wherein the first and second lateral walls are configured to extend between the anterior wall and the posterior wall. The implant further includes a top surface having a plurality of teeth adapted to at least partially engage a lower surface of a first vertebral body and a bottom surface having a plurality of teeth adapted to at least partially engage an upper surface of a second vertebral body, wherein the second vertebral body is adjacent to the first vertebral body. The implant further comprises one or more internal chambers positioned between the anterior wall, the posterior wall, the first lateral wall and the second lateral wall, wherein the internal chamber at least partially extends from the top surface to the bottom surface of the implant.

In some embodiments, the implant additionally includes at least one opening extending through the anterior wall, wherein the opening is in fluid communication with the internal chamber. In one embodiment, the implant further comprises at least one access port located in the anterior wall, the first lateral wall and/or the second lateral wall, wherein the implant is configured to releasably secure to an insertion tool using the access port. In some embodiments, the access port is configured to receive a graft material that is delivered into the internal chamber after the implant has been secured within the intervertebral space. In one embodiment, the posterior wall does not comprise any openings. In some arrangements, the graft material delivered into the internal chamber is configured to exit the implant through at least one opening of the anterior wall.

According to some embodiments, the implant comprises polyether etherketone (PEEK). In several arrangements, the length of each of the first and second lateral walls is approximately 10-20% of the overall length of the implant. In some embodiments, each of the first and second lateral walls is configured to generally align with the peripheral bearing areas of the adjacent vertebral members. In some embodiments, the plurality of teeth situated along the top and/or bottom surfaces of the implant are configured to slant to toward a lateral center of the implant. In one embodiment, the first lateral wall and/or the second lateral wall comprises a tapered portion to facilitate insertion of the implant into the intervertebral space. In some arrangements, the implant is configured for lateral, anterior or posterior insertion into the targeted intervertebral space. In some embodiments, the implant is configured for placement within a lumbar or thoracic portion of a patient's spine. In one embodiment, the implant additional comprises a plurality of prongs extending into the interior chamber for retaining a graft or other member positioned therein.

BRIEF DESCRIPTION OF THE DRAWINGS

These and other features, aspects and advantages of the present application are described with reference to drawings of certain embodiments, which are intended to illustrate, but not to limit, the present disclosure. It is to be understood that these drawings are for the purpose of illustrating concepts of the present disclosure and may not be to scale.

DETAILED DESCRIPTION

Figure 1A:
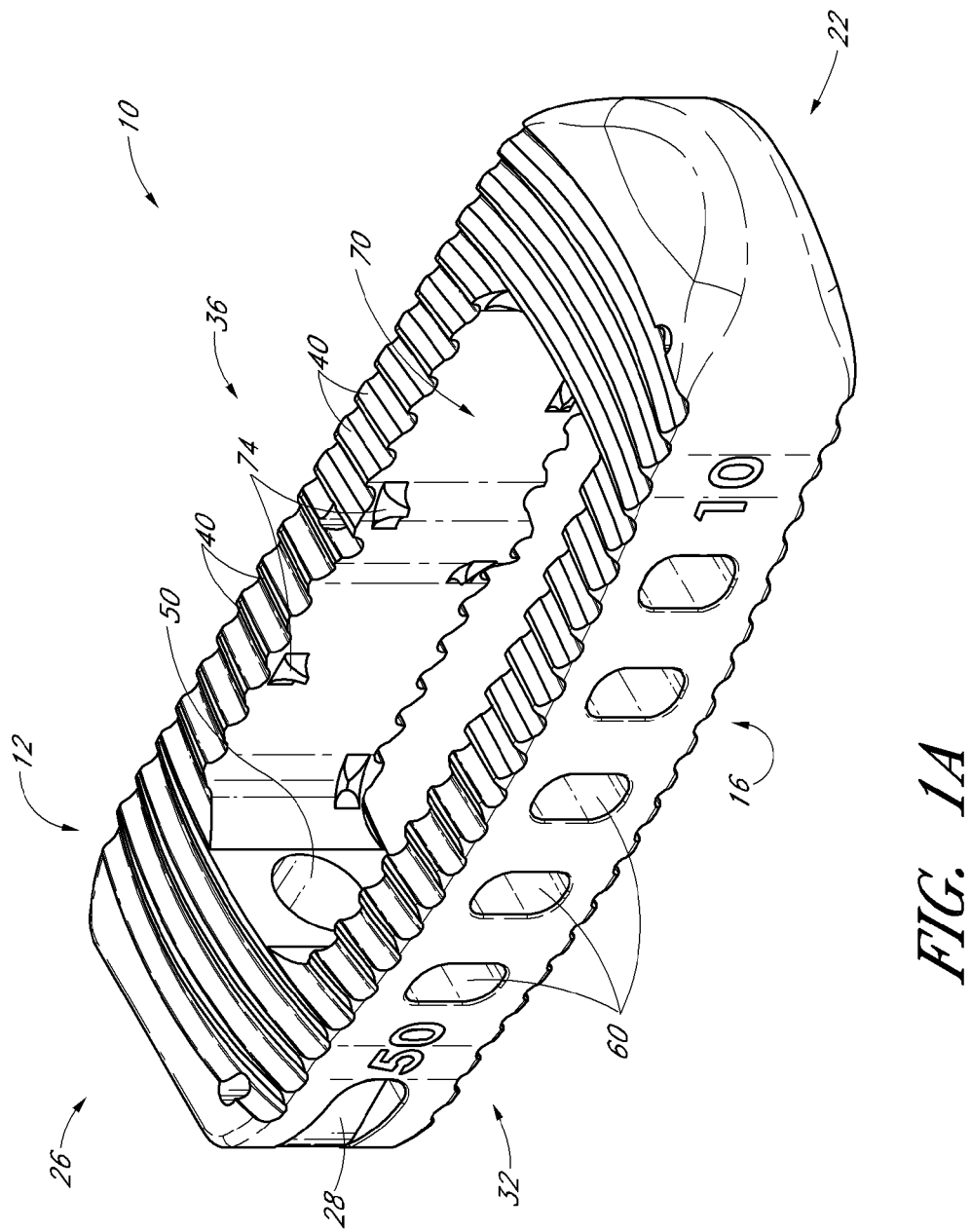
FIG. 1A illustrates a front perspective view of a spinal implant according to one embodiment.

A variety of embodiments and examples described herein illustrate various configurations that may be employed to achieve desired improvements. The particular embodiments and examples are only illustrative and not intended in any way to restrict the general nature of the inventions presented and the various aspects and features of and relating to these inventions.

Spinal Implant

FIG. 1 illustrates one embodiment of a spinal implant 10 configured for placement between adjacent vertebrae of a patient. According to certain arrangements, the implant 10 is sized, shaped and otherwise adapted for placement with an intervertebral space along the lumbar region of spine. Alternatively, however, the implants and/or the methods disclosed herein can be modified for placement in any other portion of the spine, such as, for example, the thoracic or cervical region. In any of the embodiments disclosed herein, the implant can be inserted into a target intervertebral space using a lateral delivery approach (e.g., XLIF or TLIF), an anterior approach (e.g., ALIF), a posterior approach (e.g., PLIF) and/or any other approach or technique.

With continued reference to FIG. 1, the implant 10 can include a generally rectangular shape. However, in alternative configurations, the implant 10 includes another shape, as desired or required by a particular application or use. For example, one or more of the implant's surfaces or sides can be more or less tapered and/or rounded (e.g., curved, convex, etc.). Further, the implant can comprise a completely different overall shape (e.g., as viewed from the top, bottom, one or more sides, etc.), such as, for example, round, oval, elliptical, other polygonal, irregular and/or the like.

According to some embodiments, the top surface 12 and/or the bottom surface 16 of the implant 10 comprise one or more teeth 40, protruding members and/or other features that are sized, shaped and otherwise configured to contact and engage adjacent surfaces of the vertebral endplates once the implant has been positioned within the intervertebral space. In one embodiment, only the top surface 12 comprises teeth or similar engagement features. In another embodiment, only the bottom surface 16 comprises teeth or similar engagement features. However, in some embodiments, both the top and the bottom surfaces 12, 16 comprise teeth or similar engagement features.

The teeth 40 or other engagement members or features can be distributed either completely or partially along the top surface 12 and/or bottom surface 16 of the implant 10. For example, the teeth or other engagement features 40 can cover the entire or substantially the entire top and/or bottom surfaces of the implant. In other arrangements, the teeth 40 are located along only selected portions of the top and/or bottom surfaces, as desired or required. As illustrated in FIGS. 1 and 2, the teeth 40 can extend, at least partially, from the anterior end 32 to the posterior end 36 of the implant. In some embodiments, at least some of the teeth 40 are generally parallel to each other. However, in other arrangements, at least some of the teeth or similar engagement features 40 of an implant intersect with one another or are otherwise non-parallel relative to each other.

With continued reference to FIGS. 1 and 2, the teeth or other engagement features 40 can be symmetrically disposed along the top surface 12 and/or bottom surface 16 of the implant 10. Alternatively, however, the tooth pattern along the top and/or bottom surfaces of the implant can be asymmetrical in one or more directions. In the illustrated embodiment, the teeth 40 are generally straight along the middle portion of the implant 10 and generally curved (e.g., circular, oval, etc.) along each of the lateral ends 22, 26 of the implant 10. Thus, the radius of curvature of the teeth 40 along the lateral ends 22, 26 of the implant is greater than the curvature of the teeth along the middle, center or interior portion of the implant. In some arrangements, the radius of curvature of the rows of teeth 40 or other engagement features can increase with increasing distance from the center of the implant 10.

The teeth or other engagement features 40 along the top surface 12 and/or the bottom surface 16 of the implant 10 can be bi-directional or unidirectional, as desired or required. Such teeth or other engagement features 40 can help ensure that the implant 10 does not migrate or otherwise undesirably move after implantation within a target intervertebral space. In addition, as discussed in greater detail herein, the teeth 40 can assist in maintaining graft and/or other fill materials within or near the implant 10 (e.g., within an internal chamber of the implant, between the endplates of adjacent vertebral members, etc.), thereby improving and/or facilitating spinal fusion. The type, quantity, shape (e.g., curvature along the top and/or bottom surfaces of the implant, the cross-sectional shape of the teeth, etc.), size (height, length, etc.), orientation, spacing and/or other details of the teeth or other engagement features 40 can vary, as desired or required.

With reference to the top view of FIG. 2, the implant 10 can include a left lateral side L and a right lateral side S. According to some embodiments, the teeth 40 along the top and/or bottom surfaces 12, 16 of the implant 10 are unidirectional. For example, the teeth 40 along the left side L of the implant are generally curved, sloped, slanted or otherwise pointed in a first direction, whereas the teeth 40 along the right side R of the implant are generally curved, sloped, slanted or otherwise pointed in a second direction, which in some arrangements, is generally opposite of the first direction.

Figure 3A:
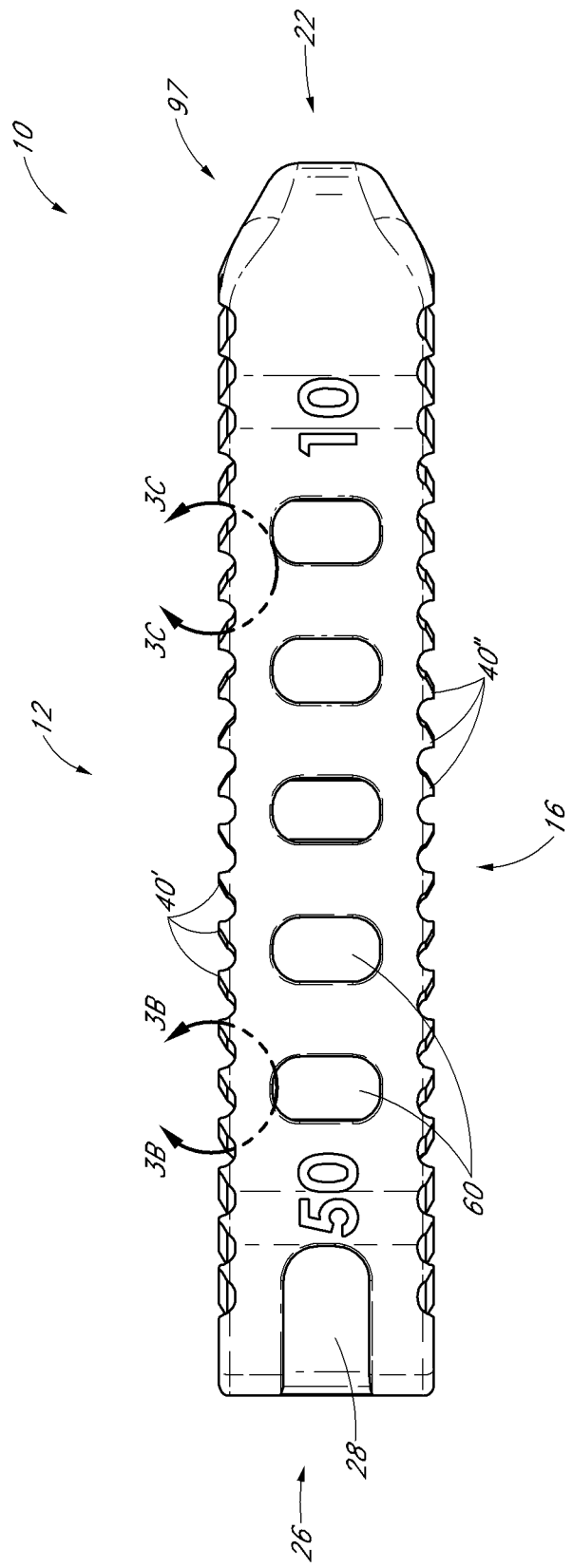
FIG. 3A illustrates a side view of the implant of FIG. 1A.
Figure 3B:
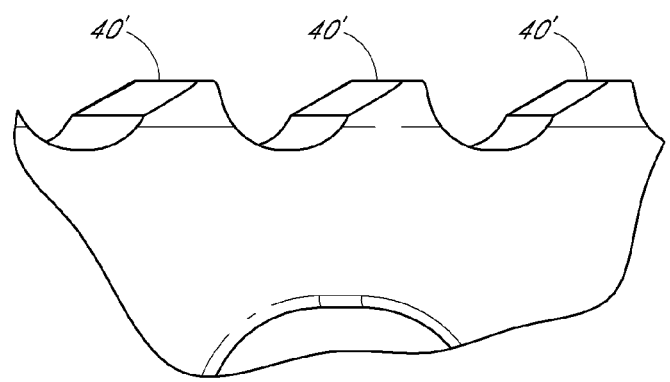
FIGS. 3B and 3C illustrate detailed side views of the implant of FIG. 1A.

Further, as illustrated in the side view of FIG. 3A, in some embodiments, the teeth 40', 40" along the upper and/or lower surfaces 12, 16 of the implant 10 are sloped or slanted toward the horizontal center of the implant. As noted above, such a configuration can help ensure that the implant 10 engages adjacent portions of a patient's spine (e.g., vertebral endplate surfaces) and does not inadvertently migrate or otherwise move after implantation. Further, such embodiments can help ensure that the likelihood that grafting agents and/or other fill materials delivered into the interior chambers of the implant 10 undesirably escape from within or near the implant (e.g., between the upper and/or lower surfaces 12, 16 and the adjacent endplate surfaces of the patient's vertebrae) is advantageously reduced or minimized. For example, with such a tooth orientation, the implant 10 needs to migrate or otherwise shift against the tooth grain (e.g., in one or more directions) in order to move laterally away from the target intervertebral space following implantation. In addition, according to some embodiments, the inwardly oriented shape of the teeth 40 makes it more difficult for grafting and/or other filler materials to flow or otherwise move at or near the implant-endplate interface.

As illustrated in FIG. 3A, the implant 10 can include generally planar top and/or bottom surfaces 12, 16, at least partially along its length and/or width. In other embodiments, however, the top surface 12 and/or the bottom surface 16 of the implant 10 comprises one or more portions that are non-planar. Such non-planar areas or portions can extend only partially along the length and/or width of the implant. In other embodiments, the entire top and/or bottom surface of the implant can be generally non-planar.

For example, the top and/or bottom surfaces can be generally concave, rounded or otherwise curved (e.g., in the vertical direction so that the thickness of the implant varies along one or more regions of the implant). Such configurations can provide for a tighter fit between the implant 10 and the adjacent endplates or other surfaces or portions of the vertebral members. In some arrangements, such configurations can help improve or enhance the spinal fusion process. In yet other arrangements, the implants can be generally planar but non-horizontal (e.g., from anterior to posterior ends). For instance, as discussed in greater detail herein, "lordotic" implant designs can include a generally higher anterior wall relative to the posterior wall.

In some embodiments, one or both lateral ends of an implant can be tapered. A tapered lateral end 22, as illustrated in FIG. 3A, can facilitate insertion of the device 10 within the target intervertebral space during an implantation procedure. In the depicted arrangement, the leading end 97 along the right lateral end 22 of the implant 10 includes both a vertical taper and a rounded profile when viewed from the top. In some embodiments, as discussed in greater detail below, at least a portion of such a "bullet" or tapered leading lateral end of the device can be configured to extend outside the intervertebral space into which the implant is implanted. According to some embodiments, one or both lateral ends of the implant comprise a rounded or curved contour. Such a rounded or curved contour or profile can be included in the vertical direction, in the horizontal direction or in both the vertical and horizontal directions, as desired or required.

In addition, as best illustrated in FIG. 2, the exterior surface of the implant's posterior side 36 can be generally flat or planar when viewed from the top. Such a design can help ensure that a proper clearance is provided between the posterior end of the implant 10 and sensitive portions of the patient's spine (e.g., nerve roots, spinal cord, etc.). Further, the exterior surface of the implant's anterior side 32 can include a rounded or other non-planar shape. In some embodiments, such a rounded or other non-planar shape is relatively gradual or slight. Likewise, as shown, the exterior of the implant's lateral sides 22, 26 can be either generally planar (e.g., flat) or rounded, as desired or required. In other embodiments, the exterior shape of the implant's sides can be different than illustrated and discussed herein.

In order to help perform an implantation procedure and to facilitate the delivery of an implant to a targeted location within a patient's spine, the implant 10 can include one or more insertion tool receiving ports 50, slots and/or other features. For example, in the embodiment illustrated in, inter alia, FIGS. 1A, 1B, 2 and 3B, a single port 50 is positioned along one of the lateral ends 26 of the implant 10. However, in other configurations, the port 50 can be positioned along any other portion of the device. The location of the port 50 can depend, at least in part, on the desired method by which the implant 10 will be inserted into the patient's spine (e.g., laterally, anteriorally, posterially, etc.). For example, in the illustrated arrangement, the port 50 is positioned along a lateral end 26, primarily because the implant 10 is designed to be inserted into the target intervertebral space laterally. Therefore, in other configurations, an insertion tool receiving port 50 can be included along the anterior side 32, posterior side 36 and/or any other portion of the implant.

Figure 6A:
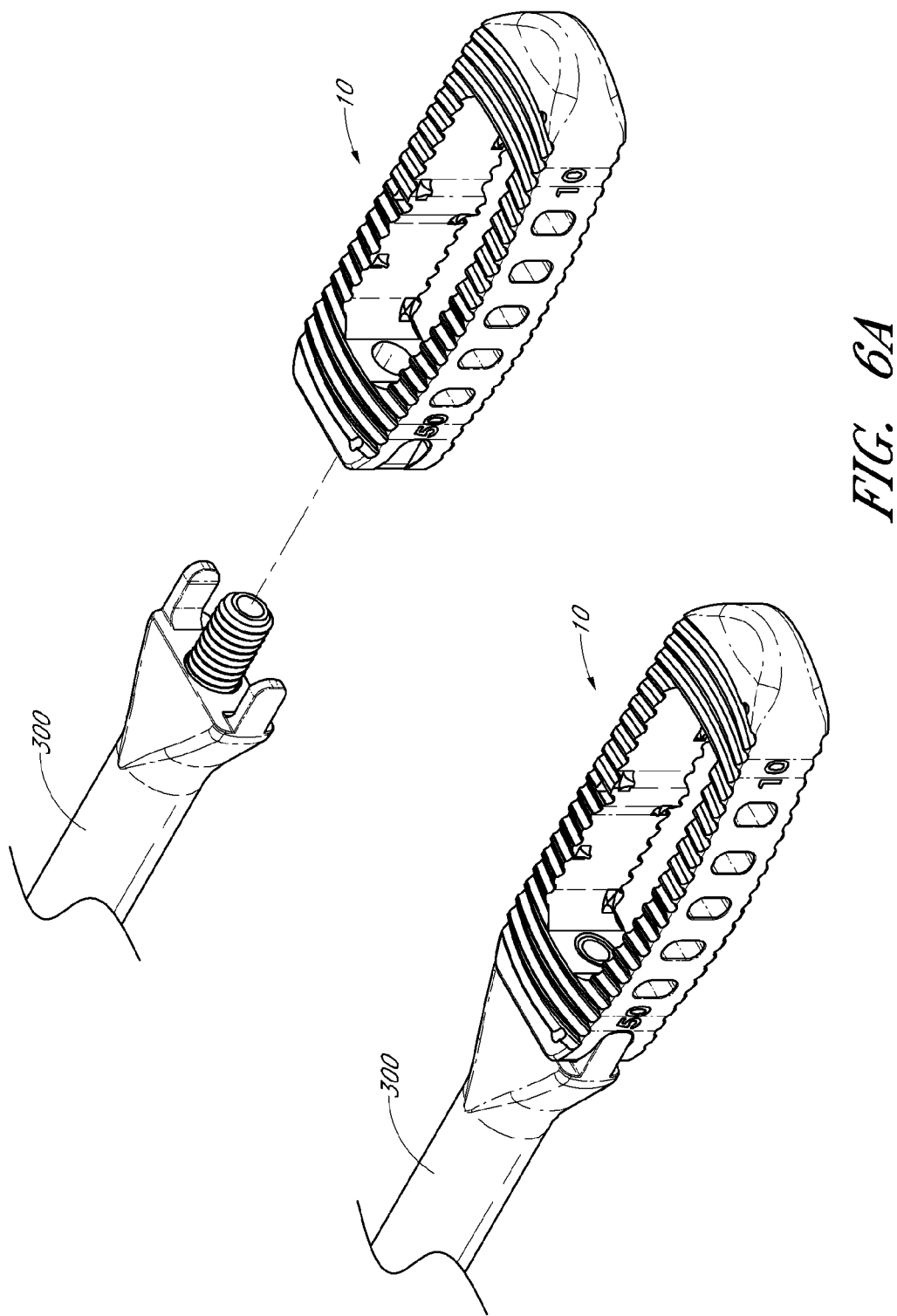
FIG. 6A illustrates perspective views of an implant and an insertion tool configured to engage the implant according to one embodiment.

According to some embodiments, the insertion tool receiving port 50 is configured to releasably engage a corresponding insertion tool using a threaded connection. For instance, the port 50 can include internal threads that are sized, shaped and otherwise adapted to match external threads of an insertion tool 300 (FIG. 6A). In other arrangements, however, other types of connection features or devices are used to releasably secure an insertion tool to the implant, such as for example, a press-fit or friction fit connection, a snap-fit connection, a tabbed connection, any other standard or non-standard coupling and/or the like. In some embodiments, as discussed in greater detail herein, the port 50 also serves as an inlet into the implant's interior chambers through which grafting and/or other fill materials can be selectively delivered within the implant. Thus, in such embodiments, a single port 50 is used both an implant delivery mechanism and a graft material passage. In some embodiments, the port 50 comprises one or more valves (e.g., check valve, other one-way valve, etc.), other flow-regulating devices or features and/or one or more other sealing members to help prevent or reduce the likelihood of the inadvertent loss of grafting and/or other fill materials from within the interior of an implant through such a port 50.

The port 50 can be threaded or non-threaded, as desired or required. In some embodiments, the port comprises one or more other engagement or other features, such as for example, alignment slots, tabs, teeth, other protruding members and/or the like. Such features can extend inwardly (e.g., in the direction of the port's opening) from the wall or other surface defining the port 50. According to some embodiments, the shape (e.g., cross-sectional shape) of the port is generally circular. However, the port can include one or more other shapes, such as, for example, oval, elliptical, square, rectangular, other polygonal, irregular and/or the like.

According to some embodiments, the threaded port 50 along a lateral end 26 of the implant is configured to pass at least partially through the implant's lateral wall 98. For example, in one embodiment, the port 50 passes through the entire lateral wall 98 and extends into one or more internal chambers 70, cavities or other openings of the implantable device 10. According to some embodiments, the port 50 is sized to permit a catheter, syringe, tubing, other tube, conduit and/or other delivery device to be passed therethrough. Such a catheter or other delivery tube or device can be sized and configured to allow grafting and/or other materials to be selectively injected or otherwise administered into one or more chambers of the implant. In one embodiment, the port is sized to permit a catheter or other tube of size French 12 or French 15 (e.g., per the standard French gauge scale) to be passed therethrough. Thus, in such arrangements, the port 50 can include a minimum inside diameter of about 4 mm or about 5 mm. In other embodiments, however, the port 50 can be sized, shaped and otherwise configured to permit the passage of larger catheters, tubes or other conduits therethrough. For instance, in some embodiments, an implant is configured to permit a catheter, tube or other conduit having an outer diameter as large as about 5 mm through 8 mm (e.g., approximately 5 mm, 5.5 mm, 6 mm, 6.5 mm, 7 mm, 7.5 mm, 8 mm, sizes between the foregoing, etc.) to pass through its port 50. In other embodiments, the port is sized and shaped to allow conduits having an outer diameter larger than 8 mm (e.g., approximately 8 mm, 8.5 mm, 9 mm, larger than about 9 mm, etc.) to pass therethrough.

In some embodiments, the threaded port 50 or access hole comprises an M6×1.0 configuration. However, as noted above, the port can comprise a nominal diameter that is greater than or less than about 6 mm, such as, for example, approximately 4 mm, 5 mm, 7 mm, 8 mm, 9 mm, 10 mm, greater than 10 mm, sizes between the foregoing values, etc.). Further, in embodiments that comprise a threaded port, the thread along the inside of the port can differ from that in an M6×1.0 configuration, as desired or required. For example, the thread type, pattern, height and/or other characteristics of the thread can vary.

According to some embodiments, the spinal implants disclosed herein or equivalents thereof comprise a generally closed structure along their sides. For example, in some arrangements, the only openings along the outer sidewalls (e.g., lateral, posterior, anterior) of an implant are one or more ports 50 (e.g., used to engage the implant with a delivery tool and/or used to pass a graft delivery tube to the interior of the implant) and/or one or more openings that permit excess grafting materials to exit an interior chamber or other cavity of the implant (e.g., openings 60 along the anterior side wall of the implant, as illustrated in FIG. 3A).

According to some embodiments, the port 50 or other openings through a wall of the implant is configured to be as large as possible for a given implant. This can permit a larger device (e.g., catheter, syringe, tubing, other conduit or device, etc.) to be positioned therein. For example, as discussed in greater detail herein, the port 50 can be advantageously adapted to receive a tube that is configured to transfer grafting and/or other fill materials from a syringe (or other supply source) to the interior of the implant. Therefore, in such embodiments, the inside diameter (or other cross-sectional clearance dimension) of the port 50 is slightly larger than the outer diameter (or other outer dimension) of the fill catheter or other conduit.

In some embodiments, the port comprises a diameter of approximately 6 mm to 8 mm (e.g., about 6 mm, 6.5 mm, 7 mm, 7.5 mm, 8 mm, diameters between the foregoing values, etc.). Alternatively, however, the diameter or other cross-sectional dimension of the port 50 can be smaller than about 6 mm (e.g., approximately 4 mm, 4.5 mm, 5 mm, 5.5 mm, 5.9 mm, diameters between the foregoing values, etc.) or larger than about 8 mm (e.g., approximately 8.1 mm, 8.5 mm, 9 mm, 9.5 mm, diameters between the foregoing values, larger than about 9.5 mm, etc.), as desired or required. In some embodiments, a target diameter or other cross-sectional dimension of the port 50 is generally maintained, irrespective of the size of the implant (e.g., 6 mm, 8 mm, 10 mm, 12 mm tall implants). This can help ensure that a surgeon or other clinician can insert a desired fill tube or other conduit within an interior of an implant (e.g., to delivery grafting and/or other fill materials during a post-fill procedure). Accordingly, as noted herein with reference to the embodiments illustrated in FIGS. 6B-6D, one or more implant walls through which the port 50 passes (e.g., lateral side walls) may need to be reinforced or otherwise strengthened to accommodate a desired port diameter (e.g., 6 mm, 8 mm, etc.) in light of the implant's thickness.

By maintaining a relatively large port diameter or other dimension, a larger fill tube or conduit can be advantageously positioned through such a port. Accordingly, the friction associated with passing grafting and/or other fill materials through the fill tube can be reduced. This allows for less strenuous delivery of grafting and/or other fill materials into the interior of an implant (e.g., during a post-fill procedure). Accordingly, the surgeon or other clinician performing a fill procedure can more easily deliver the necessary materials through the fill tube. Therefore, although it is somewhat counterintuitive to include a relatively large port or other openings along one or more walls of the implant (e.g., because of the likelihood of grafting and/or other filler materials leaking out of the implant), such an oversized port can provide one or more benefits and advantages during a fill procedure.

According to some embodiments, the ratio of the port diameter (or other port opening size) to the height of the implant wall through which the port is located (e.g., lateral wall) is between about 0.4 and about 0.9 (e.g., approximately 0.4, 0.45, 0.5, 0.55, 0.6, 0.65, 0.7, 0.75, 0.8, 0.85, 0.9, ratios between the foregoing values, etc.), depending on the size of the implant. For example, in some embodiments, the port diameter is approximately 6 mm and the height of the corresponding implant wall is 8 mm, 10 mm, 12 mm or the like. Thus, the ratio can be approximately 0.75, 0.6, 0.5 and/or the like. In some embodiments, the ratio of the port diameter (or other port opening size) to the height of the implant wall through which the port is located (e.g., lateral wall) is at least about 0.5, 0.55, 0.6, 0.65, 0.7, 0.75, 0.8, 0.85, 0.9, greater than about 0.9 and/or the like.

In some embodiments, the area of the port 50 is at least about 10%, 15%, 20%, 25% or 30% of the overall area of the wall (e.g., lateral implant wall) through which the port is positioned. However, the port area can be smaller than about 10% or greater than about 25% of the overall area of the wall through which the port is positioned, as desired or required.

As discussed in greater below, the implants disclosed herein can be provided in a variety of shapes, sizes and configurations in order to better accommodate the intervertebral spaces into which they will be inserted and secured. Thus, in some embodiments, the various types of implants that are supplied to a surgeon or other clinician comprise an identical port 50 (e.g., having an identical diameter, shape, thread pattern, etc.), regardless of the actual size, shape and other details of the devices. Accordingly, a surgeon or other clinician can use a single insertion tool and/or a single set of other instruments to engage and manipulate the various types of implants provided. Further, as noted above, in addition to serving as a securement site and/or other engagement means for a tool used during the delivery of the implant through a patient's anatomy, the port 50 can also be used as a passageway for a catheter, syringe, tube or other conduit. Such conduits can be passed through the port 50 to selectively deliver grafting agents, other filler materials and/or any other device or substance within an interior chamber, cavity or other portion of the implant. In some embodiments, the passage of catheters and/or other conduits through the port is performed after the implant has been securely positioned within a target intervertebral site and after one or more delivery tools have been detached from the implant. In other embodiments, as disclosed herein, the graft delivery catheter or other conduit can be passed through the port 50 to reach an interior portion of the implant while an implant delivery tool is secured to the port. For example, such a catheter or conduit can be passed through an interior lumen or other passage of a cannulated implant delivery tool.

Figure 6B:
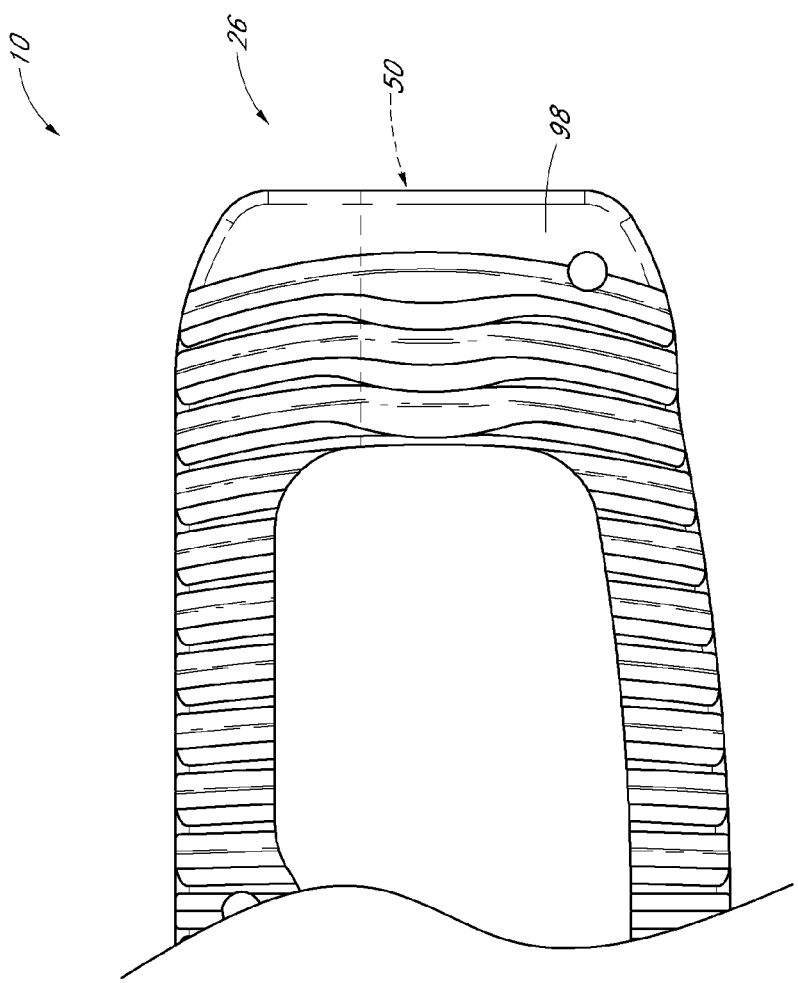
FIG. 6B illustrates a partial top view of a spinal implant according to one embodiment.
Figure 6C:
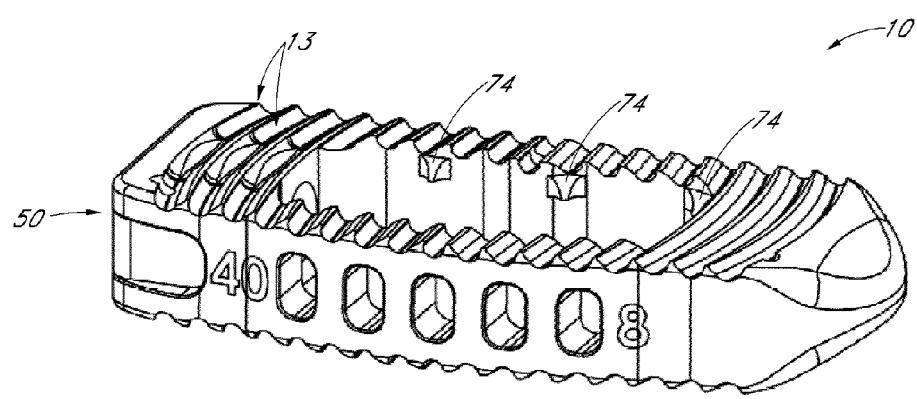
FIG. 6C illustrates a perspective view of a spinal implant according to one embodiment.
Figure 6D:
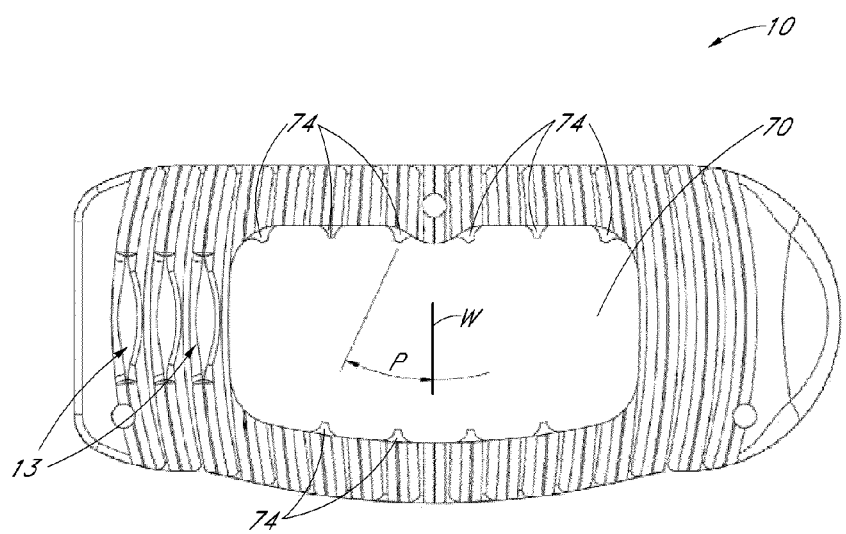
FIG. 6D illustrates a top view of a spinal implant according to one embodiment.

In order to maintain an identical threaded or other type of port 50, one or more portions of smaller implants (e.g., implants that have a smaller height, such as, for example, 6 mm, 8 mm or 10 mm devices) may be reinforced with additional material and/or other support along or near an area surrounding the port 50. For example, as depicted in the embodiment illustrated in FIGS. 6B-6D, additional implant material 13 (e.g., PEEK, other polymeric or other material, etc.) is included along the top and/or bottom surfaces of the implant 10 along or near the port 50. This can advantageously permit the manufacture of implants of various sizes that include a single type of port 50, while maintaining the requisite structural and functional integrity of the implant. For instance, the use of additional material or other reinforcement 13 along the top and/or bottom surface of the implant 10 can provide the requisite resistance to the forces and moments to which the implant may be subjected during delivery and/or use. As shown in FIGS. 6B-6D, in arrangements where additional reinforcing material 13 is provided along the top and/or bottom surfaces, such additional material can be positioned within at least of the grooves that help define the teeth 40 or other engagement features of the implant 10. Thus, the depth and general configuration of the teeth 40 along such reinforced areas may vary from adjacent areas of the implant.

Figure 3C:
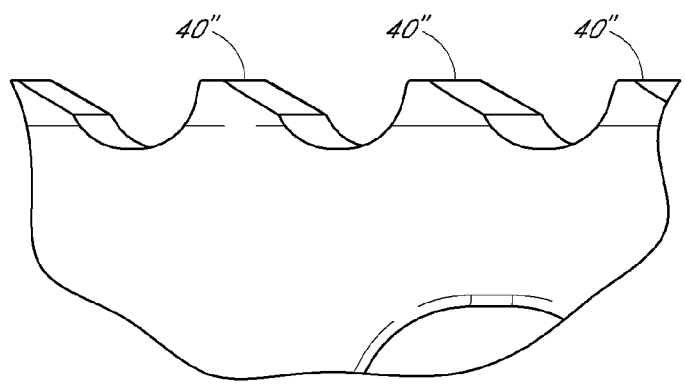
Figure 4:
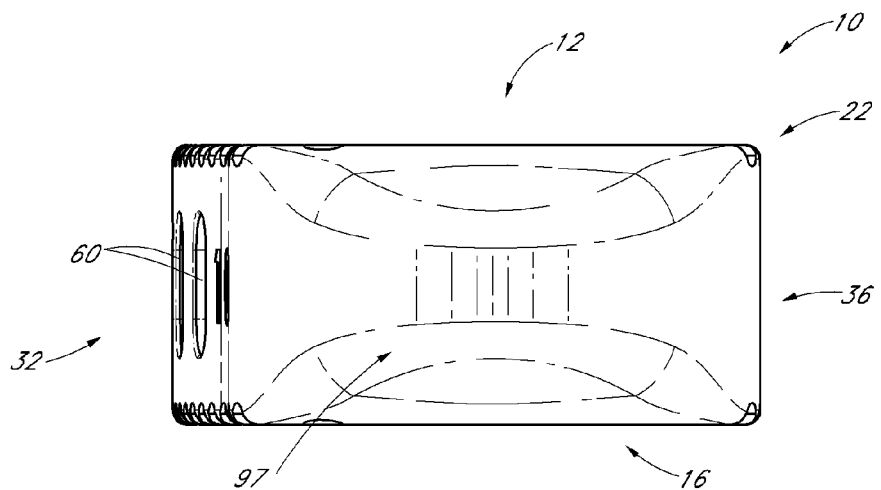
FIGS. 4 and 5 illustrate different side views of the implant of FIG. 1A.
Figure 5:
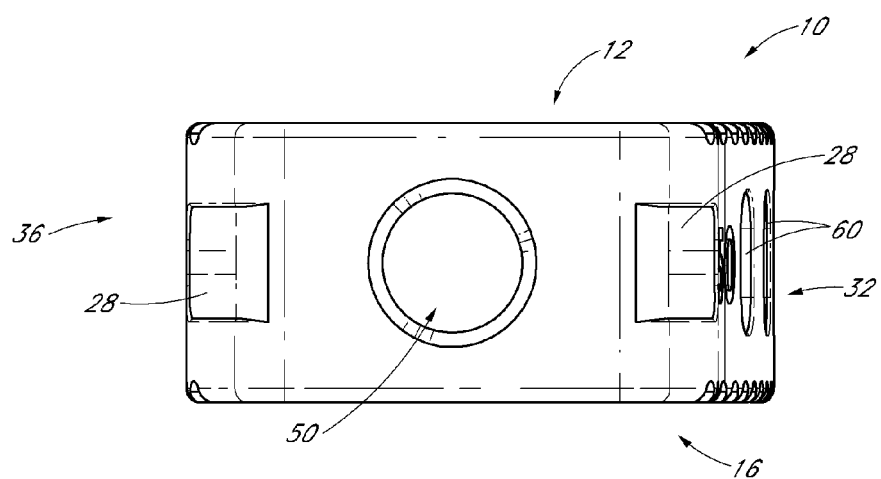

Further, the implant 10 can include one or more additional features that facilitate engagement with a corresponding insertion tool. According to some embodiments, as depicted, for example, in FIG. 3, the implant comprises two recesses or slots 28 along one of the lateral ends 26 (e.g., along the lateral end that includes the insertion tool receiving port 50). Such recesses or other features 28 can be sized, shaped, positioned, spaced, oriented and/or otherwise adapted to align and mate with corresponding wings, tabs or other portions of an insertion tool. The recesses, slots and/or other engagement features 28 can help a surgeon or other clinician to manipulate (e.g., rotate) the implant during surgery or other procedure involving moving or repositioning the implant. Further, such engagement features 28 can help ensure that the corresponding implant insertion tool (and/or graft fill tool, as discussed in greater detail herein) is properly positioned relative to the implant.

Figure 1B:
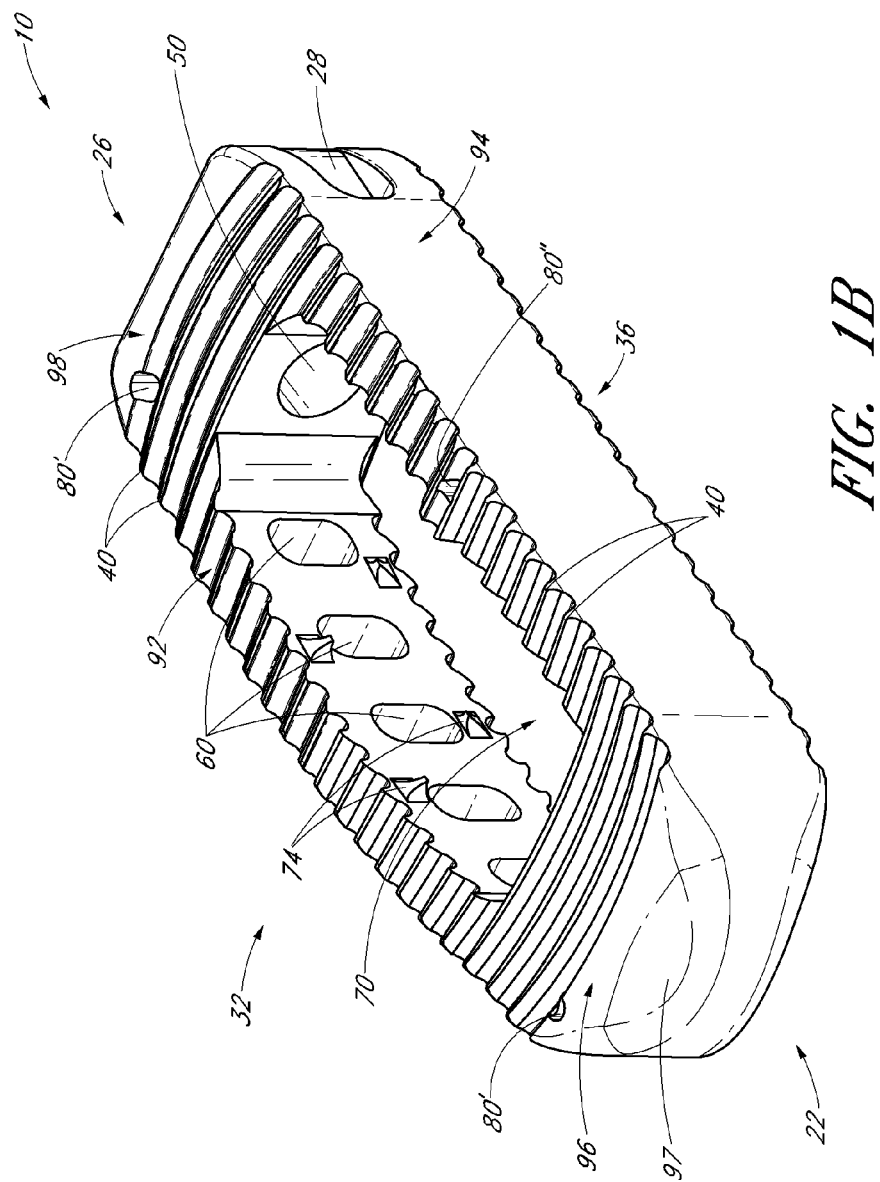
FIG. 1B illustrates a rear perspective view of the implant of FIG. 1A.
Figure 2:
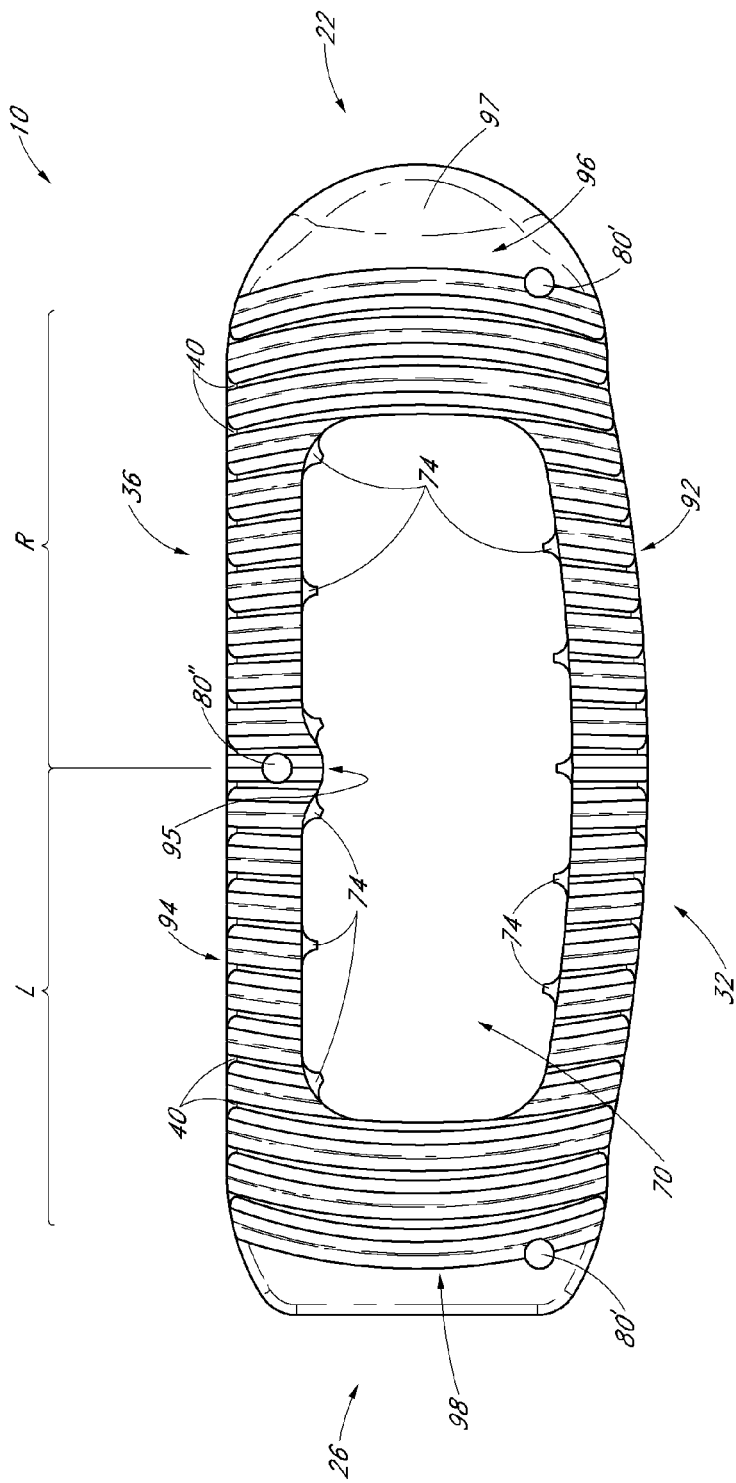
FIG. 2 illustrates a top view of the implant of FIG. 1A.

With continued reference to the embodiments depicted in, inter alia, FIGS. 1A, 1B and 2, the spinal implant 10 can include one or more internal chambers 70. In one embodiment, the implant comprises only a single chamber. However, in alternative embodiments, the implant comprises two or more chambers. As shown, such internal chambers 70 can extend across the entire implant depth (e.g., from the top surface 12 to the bottom surface 16) and across a majority of the implant's length and width. For example, in some arrangements, the chamber 70 spans approximately 60-70% of the implant length and width. However, in other embodiments, the chamber 70 can extend less than about 60% of the implant length and/or width (e.g., approximately 30%, 35%, 40%, 45%, 50%, 55%, 60%, less than 30%, percentages between the aforementioned values, etc.), or more than about 70% of the implant length and/or width (e.g., approximately 70%, 75%, 80%, 85%, more than about 90%, percentages between the aforementioned values, etc.), as desired or required by a particular application or use.

In some embodiments, an implant comprises two or more chambers. For example, the implants illustrated in FIGS. 1A-5 can include one or more dividing walls (not shown) that extend across the chamber 70 generally between the anterior and posterior walls 92, 94. Such dividing walls or other separators, which may be integrally formed with adjacent portions of the implant, can effectively create two or more sub-chambers or cavities in the implant. In implant arrangements having two or more chambers, sub-chambers, cavities and/or other openings, such chambers or sub-chambers can be of equal or different shape and/or size. Further, one or more openings can be included in the dividing wall or other separators to permit the chambers to be in fluid communication with one another. This may be particularly important when the filling the implant with grafting and/or other materials (e.g., to help ensure that such fill materials are delivered into all of the chambers).

As depicted in FIGS. 1A and 1B, a spinal implant 10 can include one or more openings 60 that extend through its anterior wall 92, but no openings along its posterior wall 94. The openings 60 can be in fluid communication with the implant's chamber(s) 70. Thus, as is discussed in greater detail below, excess grafting and/or other fill materials delivered into the chamber(s) 70 (e.g., through a fill port 50 and/or other opening in the implant) can exit through the openings 60 toward the anterior portion of the spine. By eliminating openings along the posterior wall, the passage of fill materials along the posterior side of the implant can be generally reduced or prevented. Thus, a majority (or almost all) of excess grafting agent and/or filler material delivered within such an implant can be configured to exit the interior of the implant through the anterior openings 60. For example, in some arrangements, more than approximately 70% (e.g., more than about 70%, 75%, 80%, 85%, 90%, 95%, etc.) of excess fill materials delivered into an implant exit through the openings 60. In some embodiments, this can advantageously help prevent or reduce the likelihood of migration of grafting and/or other fill materials toward nerve roots, spinal cord and other sensitive regions of the spine.

With continued reference to the side view of the embodiment illustrated in FIG. 3A, an implant 10 can include a total of five openings 60 that are generally equally sized and equally spaced apart from each other along the anterior wall. In the depicted configuration, the openings 60 comprise an oval shape or a generally rectangular shape with rounded corners. Alternatively, the openings 60 can include any other shape (e.g., circular, square, rectangular, other polygonal, irregular, etc.). Further, the quantity, spacing, relative size, orientation and/or other characteristics of the openings 60 can be different than illustrated and discussed herein. For example, depending on the implant's size, design bearing capacity and/or other properties, additional (e.g., six, seven, eight, nine, ten, more than ten, etc.) or fewer openings (e.g., four, three, two, one) can be provided.

In addition, as illustrated in, among other places, the top view of FIG. 2, the implant 10 can comprise one or more internal prongs or other protruding members 74 that extend into the chamber 70. As with other features of the implant, such prongs 74 can be formed as a unitary structure with adjacent portions of the implant. Alternatively, the internal prongs 74 can be separate members that are subsequently secured to the implant using one or more connection devices or methods, such as for example, screws, rivets, other fasteners, adhesives and/or the like. The prongs 74 can be positioned along various locations of the implant's interior surface. For example, in some embodiments, as illustrated in FIGS. 6A and 6C, the prongs are positioned along various lateral portions near the top and/or bottom of the implant. However, the internal prongs or other engagement member can be situated along any other portion or area of the chamber 70, either in addition to or in lieu of the top and/or bottom portions of the implant.

According to some embodiments, as depicted in FIG. 6D, the prongs 74 are directed toward the interior chamber or cavity 70 of the implant 10. The prongs 74 can be aligned generally perpendicularly relative to the interior vertical wall that defines the chamber 70 and from which the prongs extend inwardly. Thus, one or more of the prongs can be positioned along a line that is offset from the lengthwise or widthwise centerline of the implant 10. For example, as shown in FIG. 6D, one or more prongs 74 are offset by angle P relative to the widthwise centerline W of the implant 10. In some embodiments, such an angle P is approximately 20-25% (e.g., about 20%, 25%, 30%, etc.). Further, as illustrated in FIG. 6D, the prongs 74 can comprise a generally conical, wedge-like, truncated cone-like, triangular, pyramid-like and/or any other shape (e.g., when viewed from the top). However, the shape, size, spacing, orientation and/or other characteristics of the prongs 74 can be different than illustrated and discussed herein.

Regardless of their exact quantity, size, shape, spacing, orientation and/or other characteristics, such prongs or other features 74 can help ensure that grafting agents and/or other fill materials are properly retained within the internal chamber(s) 70 of the implant 10. For example, in some embodiments, a solid graft, a porous foam structure, a sponge and/or other solid or non-flowable member is positioned within the chamber 70 of the implant, either before or after implantation into a patient. Thus, the prongs 74 can help engage such items and maintain them within the implant. In some embodiments, the prongs 74 help secure grafting and/or other filler materials within a chamber 70 of the implant only after such materials have become adequately hardened or solidified.

As illustrated in FIGS. 1A-5, the thickness (e.g., vertical height) and width (e.g., anterior-posterior distance) of the implant 10 can be generally consistent throughout its entire length. Alternatively, one lateral end of the implant can comprise a larger thickness than the opposite lateral end. Such arrangements can be advantageously used when inserting an implant along to a lordotic portion of the spine. For example, the height difference between opposing ends in such lordotic implants can differ by about 2 mm. In other embodiments, the height difference is less or greater than about 2 mm (e.g., approximately 0.5 mm, 1 mm, 1.5 mm, 2.5 mm, 3 mm, 3.5 mm, 4 mm, greater than 4 mm, distances between the aforementioned values, etc.), as desired or required for a particular patient or fusion procedure.

Figure 7A:
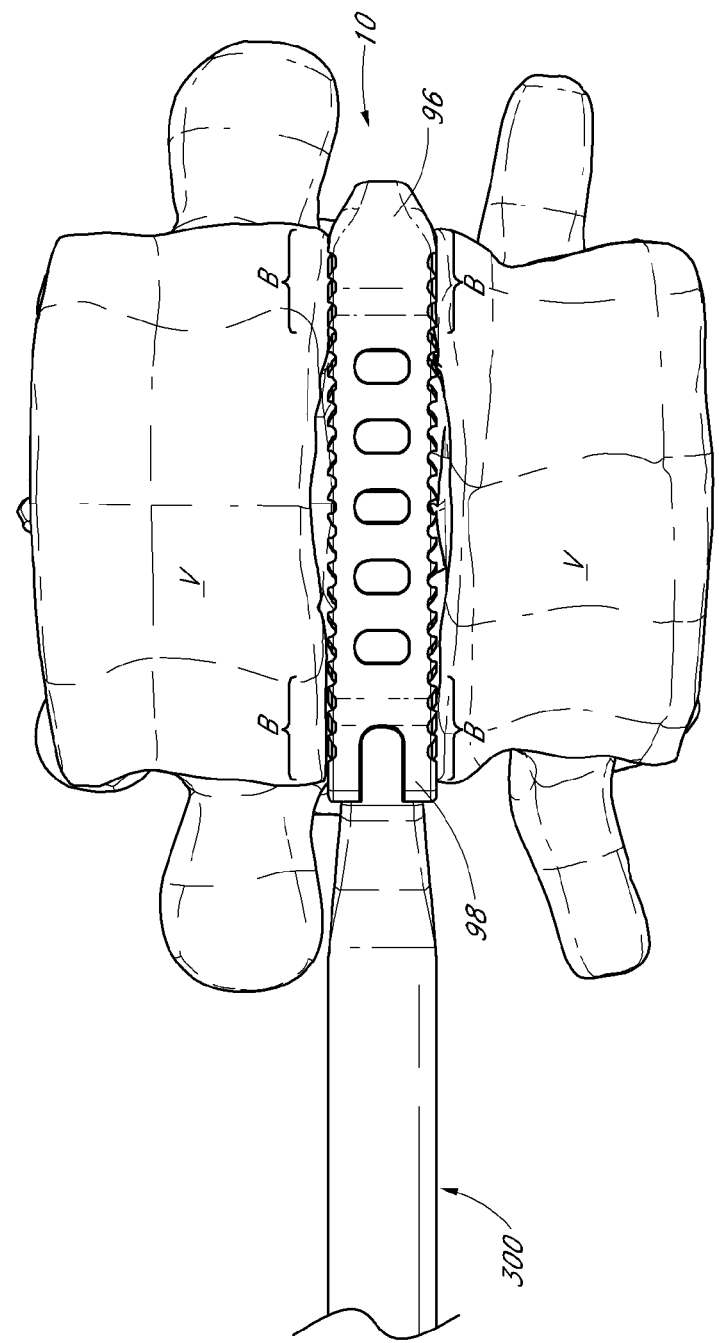
FIG. 7A illustrates an anterior side view of an implant within a targeted intervertebral space and secured to an insertion tool assembly, according to one embodiment.
Figure 7B:
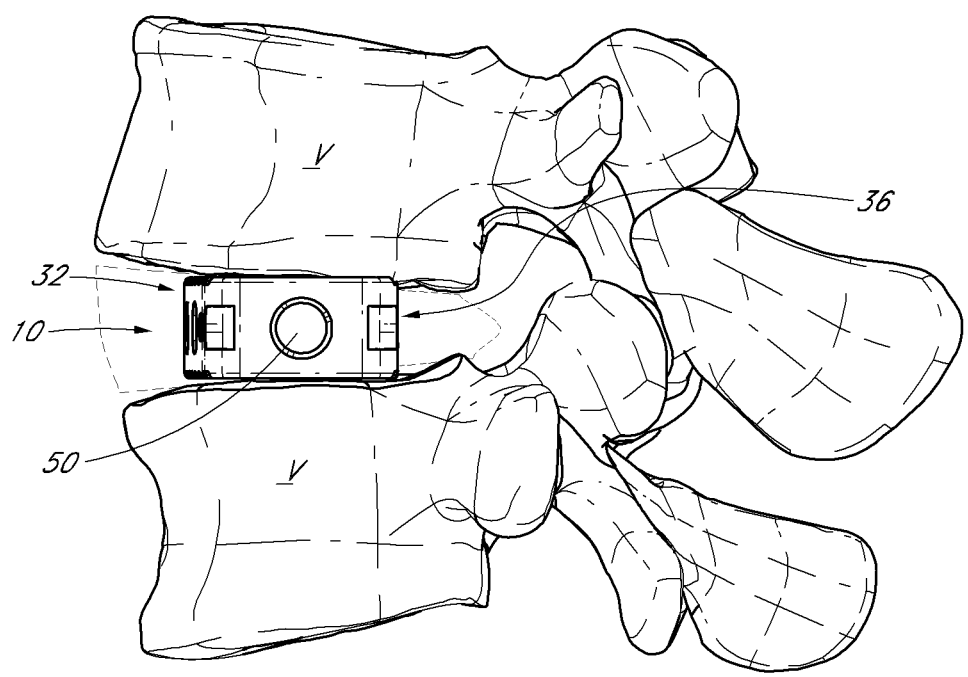
FIG. 7B illustrates lateral side view of the implant of FIG. 7A.

According to some embodiments, the horizontal width of the implant's lateral walls 96, 98 can be configured to enhance the implant's ability to withstand the bearing forces, moments and other loads to which it will be subjected once properly implanted into a patient's spine. For example, as illustrated in the anterior-posterior view of FIG. 7A, the lateral walls 96, 98 of the implant 10 can be configured to align with portions B of the adjacent vertebrae V through which the highest concentration of bearing forces are transferred to the implant 10. In general, such high bearing load areas or portions B are situated near the lateral or circumferential ends of the vertebrae V. Typically, as depicted in FIG. 7A, the endplates of the vertebrae V move further away from the adjacent intervertebral space near the center of the vertebral body. Thus, most of the bearing load created by the adjacent vertebrae V is expected to be concentrated toward the peripheral ends of the implant 10.

Accordingly, in order to improve its load bearing capacity, the implant 10 can include lateral walls 96, 98 that are generally reinforced and otherwise adapted to safely handle the bearing loads imposed upon the implant following implantation. For example, the lateral walls 96, 98 can be wider (e.g., horizontally) than the anterior and/or posterior walls 92, 94 of the implant. In some embodiments, the horizontal length (e.g., along the longer axis of the implant) of each of the lateral walls 96, 98 is at least about two times greater than the horizontal width of the anterior or posterior wall. For instance, in some embodiments, the horizontal length of one or both of the lateral walls 96, 98 is approximately at least two, three, four or more than four times the horizontal width of the anterior wall or the posterior wall of the implant. In some embodiments, the horizontal length of one or both of the lateral walls 96, 98 is approximately 10 to 20% (e.g., about 10%, 12%, 14%, 16%, 18%, 20%, percentages between the foregoing values, etc.) of the overall horizontal length of the implant (e.g., along the longer axis of the implant). Alternatively, however, the horizontal length of the one or both of the lateral walls 96, 98 can be greater than about 20% or less than about 10% of the overall horizontal length of the implant 10, as desired or required. Consequently, one or both of the implant's lateral ends 22, 26 can be configured to better withstand the bearing forces and moments to which the implant it will be subjected once inserted and secured within a targeted intervertebral space of the patient's spine.

According to some embodiments, a spinal implant is sized to generally span across the entire width of the adjacent vertebral members V. Thus, as discussed above, the lateral walls of the implant can be generally aligned with the load bearing portions of the inferior and superior vertebral members. In some embodiments, as discussed above with reference to FIG. 7A, the implant contacts the adjacent vertebral members primarily or only along the lateral ends of the implant. Thus, portions of the implant that are interior to the lateral ends of the implant are configured to encounter less or no forces from the adjacent vertebral members.

According to some embodiments, the implant 10 comprises one or more radio-opaque markers 80. Such markers 80 can facilitate a surgeon or other clinician to properly position the implant within the target intervertebral space, especially when minimally invasive surgery is utilized. By way of example, as illustrated in FIGS. 1A, 1B and 2, the implant 10 can include a total of three tantalum or other types of radiopaque markers 80', 80". In the depicted arrangement, two markers 80' are located at or near the lateral ends 22, 26, while a third marker 80" is located at or near the horizontal center of the implant 10. In one embodiment, the lateral or horizontal location of the middle marker 80" is exactly between the two lateral markers 80". The quantity, type, location, orientation, spacing and/or other details of the markers can be varied, in accordance with the specific requirements of an application or use.

As illustrated in the top view of FIG. 2, the posterior wall 94 of the implant 10 can include a bump or other reinforced region 95 in order to accommodate the center radio-opaque marker 80". In addition to providing additional material that can surround a marker, such bumps 95 or similar features can advantageously improve the implant's strength and/or other structural characteristics.

The various configurations of the implants disclosed herein can include one or more materials. For example, in some embodiments, the implants comprise polyether etherketone (PEEK), other radiolucent materials, other thermoplastics, metals, alloys and/or any other materials having the desired structural (e.g., rigidity), mechanical, chemical and thermal resistance and/or other properties.

As discussed in greater detail herein, the size of the implant can be selected based, at least in part, on the patient's weight, height, age, the amount of intervertebral distraction that the implant should provide and/or any other factor or consideration. For example, in some embodiments, the implant is precisely selected based on the size of the patient's intervertebral space into which the implant will be placed. For instance, the vertical height of the implant can vary between approximately 8 and 14 mm (e.g., 8 mm, 10 mm, 12 mm, 14 mm, values between such ranges, etc.). As noted herein, the vertical height of the implant can be consistent from the anterior end to the anterior end. Alternatively, the vertical height of the implant can vary in one or more horizontal directions (e.g., anterior-posterior direction, lateral direction, etc.).

In some embodiments, the implant includes a concave or other non-planar (e.g., domed, curvate, etc.) upper surface and/or lower surface. Such a configuration can help provide improved contact between the implant and the endplate surfaces of the adjacent vertebrae. Further, the height of the implant can vary along the anterior-posterior direction. For example, in some embodiments, the vertical height of the anterior wall of the implant is approximately 2 mm higher than the vertical height of the posterior wall. Such a configuration can be advantageously used when performing fusion to a lordotic portion of the spine. Therefore, as noted above, any of the fusion implants disclosed herein can have vertical dimensions that vary along their longitudinal direction. As a result, a variety of different lordotic implants can be provided, such as, for example, 8 mm by 10 mm (e.g., posterior height by anterior height), 10 mm by 12 mm, 12 mm by 14 mm implants and/or the like.

Moreover, the implant can be provided in a variety of horizontal dimensions in order to better accommodate the targeted intervertebral space into which the implant will be inserted and secured. For instance, the length of the implant (e.g., from one lateral end to the other) can vary between 40 mm and 60 mm. In some embodiments, the implant is provided in a variety of different lengths, such as, for example, 40 mm, 45 mm, 50 mm, 55 mm, 60 mm, lengths between the foregoing values, etc. Alternatively, the length of an implant can be greater than 60 mm or smaller than 40 mm, as desired or required. Likewise, the width (e.g., the distance between the anterior and posterior ends) of the implant can vary, both from implant to implant and within a specific implant design. For example, in some embodiments, the width of the implant is between about 19 mm and 21 mm. As discussed above with reference to FIG. 2, the width can vary along an implant's length. In some embodiments, such a variation in width results from rounded or curved anterior and/or posterior surfaces. Thus, in some embodiments, the implant comprises a width of approximately 21 mm at its longitudinal center (e.g., at or near the location of the middle marker 80" is located in the arrangement depicted in FIG. 2) and a width of approximately 19 mm at or near the lateral ends 22, 26. The implants can include any other shape, size or orientation, irrespectively of the specific examples provided herein.

Implantation into Targeted Intervertebral Space

The initial surgical steps in preparing a patient for a spinal fusion procedure can include, among other things, making an incision along the patient's skin and accessing a targeted region of the spine (e.g., lumbar region) using one or more dilators, retractors and/or other instruments or tools. Depending on the state of the diseased intervertebral disc or space, one or more preparatory steps may be necessary or recommended prior to delivery of the implant within the patient's anatomy. For example, at least some of the native disc material can be removed in order to provide the necessary space for the subsequent insertion of the implant. In some arrangements, a distraction tool is used to separate the vertebrae between which the implant will be positioned.

Further, the surgeon or other clinician performing the procedure may choose to size the target intervertebral space prior to implantation. For example, such a step can be performed in order to more accurately select a properly sized implant. In addition, a surgeon may choose to prepare one or more native surfaces of the vertebrae that will be adjacent to the implant. For instance, one or more coarsening or abrading tools can be used to selectively roughen one or more portions of the vertebral endplates adjacent to the implant. Under certain circumstances, such a roughening step can promote healing and can accelerate the fusion process following delivery of the implant within the spine.

Figure 8:
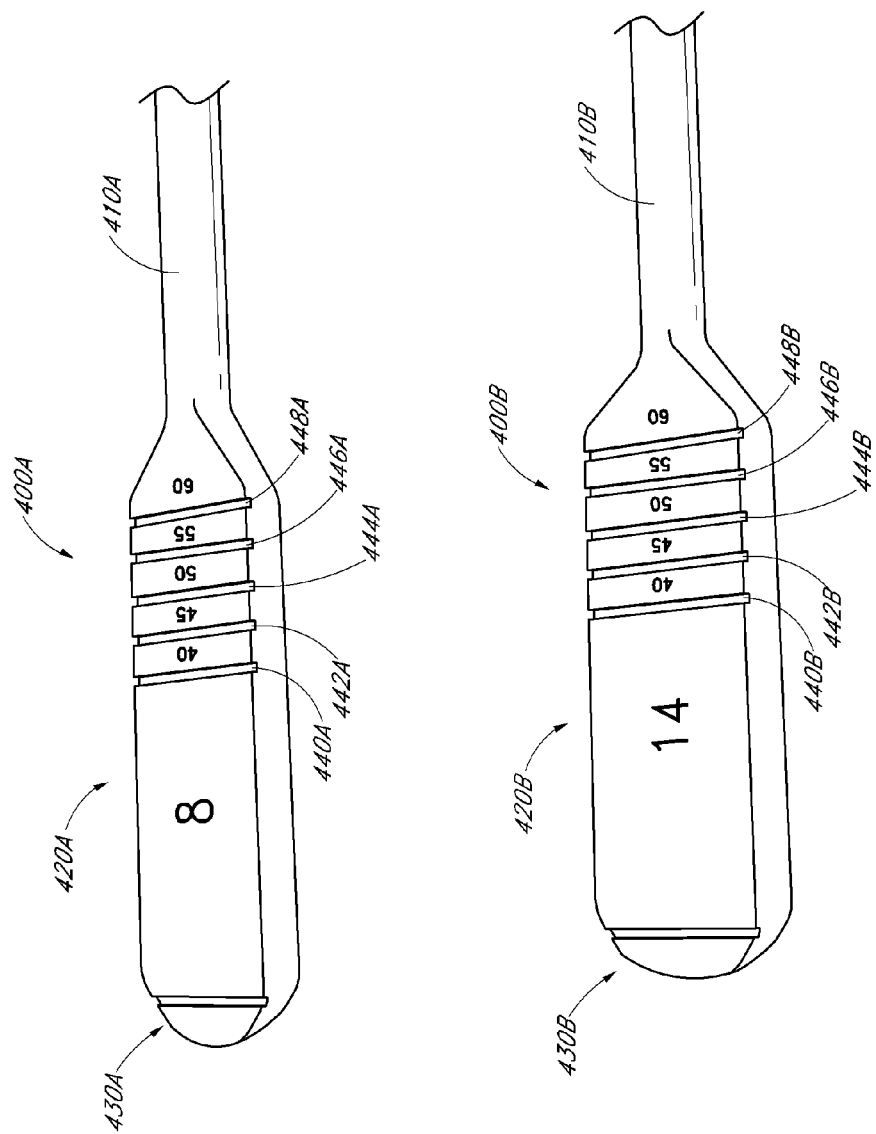
FIG. 8 illustrates two embodiments of sizing and distraction tools.

FIG. 8 illustrates two different arrangements of a distraction and sizing tool 400A, 400B that can be used in advance of the delivery of an implant during a spinal fusion procedure. As shown, the distraction and sizing tool 400A, 400B can include a proximal handle 410A, 410B (which is only partially depicted in FIG. 8) and a distal head 420A, 420B.

In the depicted embodiments, the two tools 400A, 400B are substantially similar to each other in overall design; however, their distal heads 420A, 420B vary in size (e.g., vertical thickness, length, etc.). A plurality of such distraction and sizing tools may be provided to a surgeon in order to allow him or her to determine what type of implant should be inserted into targeted intervertebral space. Such tools 400A, 400B can also be used to precisely distract or separate adjacent vertebrae in preparation for implantation.

In some embodiments, the sizing and distraction tool 400A, 400B comprises stainless steel, other metals or alloys and/or one or more other rigid material that are adequate for insertion into a patient's anatomy and configured to withstand the anticipated forces, moments and/or other conditions (e.g., pH, temperature, etc.) to which they will be subjected. With continued reference to FIG. 8, the sizing and distraction tool 400A, 400B can include a baseline marker 430A, 430B at or near the distal end of the head 420A, 420B. In some arrangements, the surgeon can insert the tool's head 420A, 420B within the target intervertebral space and advance the tool (e.g., under the guidance of x-ray, ultrasound, fluoroscopy and/or other imaging technology) until the baseline marker 430A, 430B exactly or approximately aligns with the peripheral distal edge of the adjacent vertebral bodies. Once the distal end of the head has been aligned, the surgeon can use the proximal markings 440A, 442A, 444A, 446A, 448A to determine the appropriate length of the intervertebral space. For example, the length can be determined based on the proximal marking that is closest to the peripheral proximal edge of the adjacent vertebral bodies. Thus, the markings 440A, 442A, 444A, 446A, 448A can be visualized using one or more imaging technologies to determine the proper implant size for the targeted intervertebral space.

Likewise, the surgeon can attempt to position tools 400A, 400B of varying head thickness into a targeted intervertebral space in order to determine a desired implant height. Accordingly, the sizing and distraction tool 400A, 400B can be used to select a well-suited implant for insertion into the patient's spine. In some embodiments, such a tool 400A, 400B can be used to create a desired level of vertical distraction within the targeted intervertebral space, especially if the adjacent vertebral bodies are undesirably close to one another (e.g., due to severe disc degeneration and/or disease).

Figure 9:
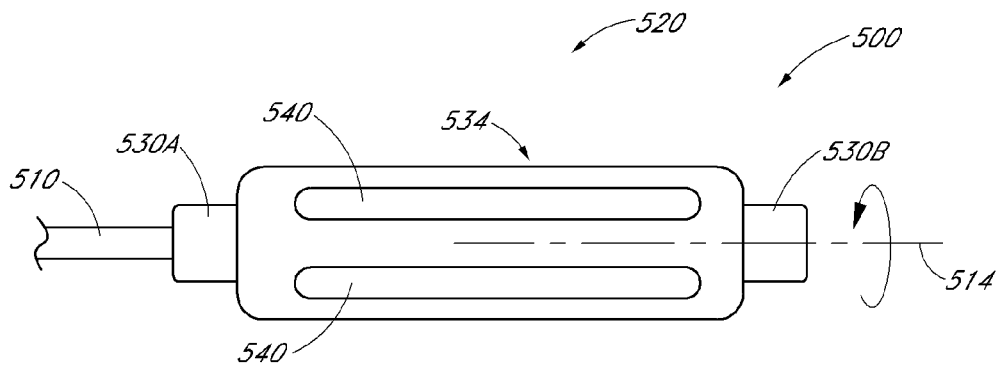
FIG. 9 illustrates one embodiment of a rasping or abrading tool for use as a preparatory tool in advance of implantation of a spinal implant.

FIG. 9 schematically illustrates one embodiment of a shaver 500 configured to selectively rasp, abrade and/or otherwise compromise or remove tissue. In some arrangements, the shaver 500 is inserted into an intervertebral space to remove disc tissue and/or prepare the vertebral endplate surfaces for the subsequent delivery of a spinal implant. As shown, the shaver 500 can comprise an abrading assembly 520 positioned along a distal end of a longitudinal shaft 510. The abrading assembly 520 can include a center or main portion 534 located between a pair of tapered outer portions 530A, 530B. In some embodiments, the center portion 534 comprises one or more abrading members 540 that are adapted to contact and at least partially remove, abrade or otherwise affect tissue. Thus, as the shaft 510 is rotated about a longitudinal axis 514, the abrading member 540 can help remove native disc tissue and/or attack the endplate wall in preparation for the subsequent implantation of the fusion device. In some embodiments, as illustrated in FIG. 9, the shaver 500 comprises tapered or lower profile outer portions 530A, 530B so as to reduce or prevent damage to the peripheral bearing areas B of the vertebral members V (see FIG. 7A). By avoiding or reducing the likelihood of damage to these native load bearing portions B of adjacent vertebrae, the structural integrity of the patient's spine, and thus the fusion procedure, can be maintained.

Figure 10A:
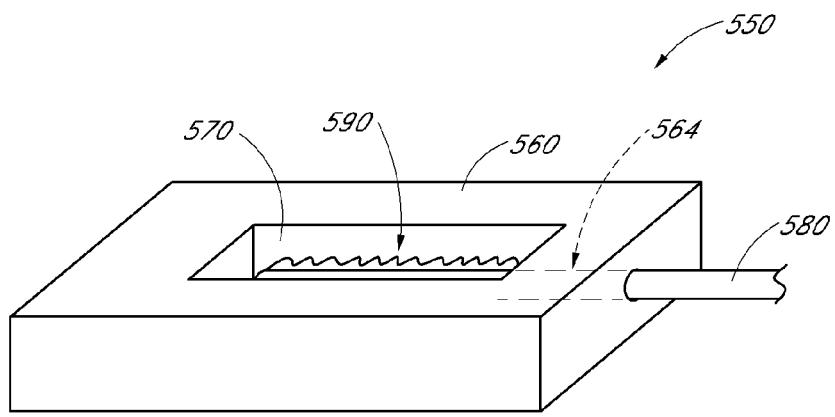
FIGS. 10A and 10B illustrate perspective views of another embodiment of a rasping or abrading tool for preparing an intervertebral space.
Figure 10B:
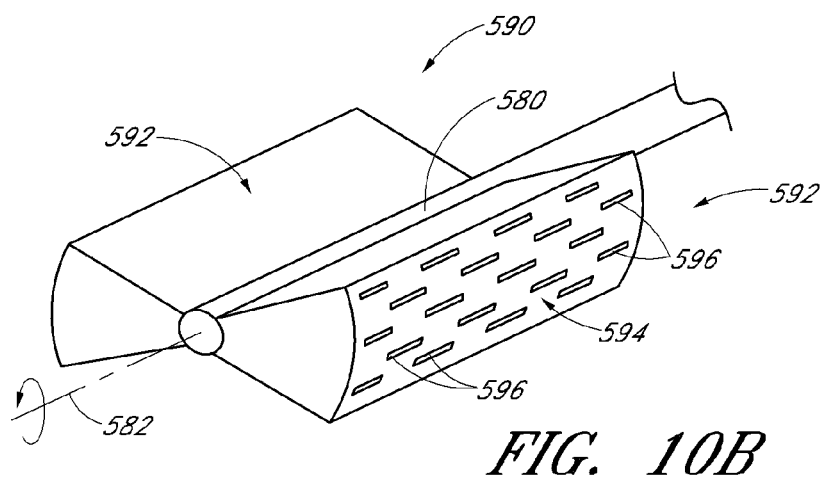

A different embodiment of a shaver instrument 550 is schematically illustrated in FIGS. 10A and 10B. As shown, the shaver 550 comprises a main portion 560 that is shaped, sized and otherwise configured for delivery into a targeted intervertebral space. The upper and lower surfaces of the main portion may or may not include teeth or other engaging features or members. In some arrangements, the main portion 560 includes a central chamber or other opening 570 that generally extends from the top to the bottom surface of the main portion 560. As depicted in FIG. 10A, an access port or opening 564 can provide access from a lateral side of the main portion 560 to the interior of the central chamber 570. An abrading assembly 590 can be positioned along the distal end of an elongated member 580. The elongated member 580 can be sized, shaped and otherwise adapted for passage through the access port 564 of the main body. Likewise, the abrading assembly 590 can be configured for placement within the chamber 570 of the main portion 560. According to some embodiments, the abrading assembly 590 is configured for selective movement within the central chamber 570 as the elongated member 580 is rotated about a longitudinal axis 582.

With continued reference to FIG. 10B, the abrading assembly 590 can comprise a generally horizontal configuration. As shown, the abrading assembly 590 can include one or more lateral wing portions 592 positioned on either side of the elongated member 580. In some embodiments, the outer surface 594 of each wing portion 592 can include one or more abrasive members or features 596 that are adapted to contact and at least partially remove or damage tissue. In some arrangements, the abrading assembly 590 is fully retained within the central chamber 570 when in the illustrated low profile or stowed orientation. Thus, the shaver 550 can be delivered to the patient's spine without interference by the abrading assembly 590. Once properly positioned within the target intervertebral space, the surgeon or other clinician can selectively rotate the elongated member 580 to move the distal wing portions 592 toward the adjacent tissue (e.g., native disc tissue, endplate surfaces, etc.). Thus, continued and repetitive rotation of the abrading assembly 590 can cause a desired amount of abrasion to the adjacent vertebral members in preparation for delivering the implant device to the intervertebral space. In some embodiments, the central chamber 570 of the shaver 550 generally aligns with a central portion of the adjacent vertebrae between the peripheral bearing areas B (FIG. 7A). Thus, damage to the load bearing areas B of the vertebrae can be reduced or avoided, as the abrading assembly 590 will be generally confined to a limited central portion of the adjacent vertebral members. Consequently, as noted above, the structural integrity of the adjacent bearing areas of the vertebral members can be advantageously maintained.

Figure 11:
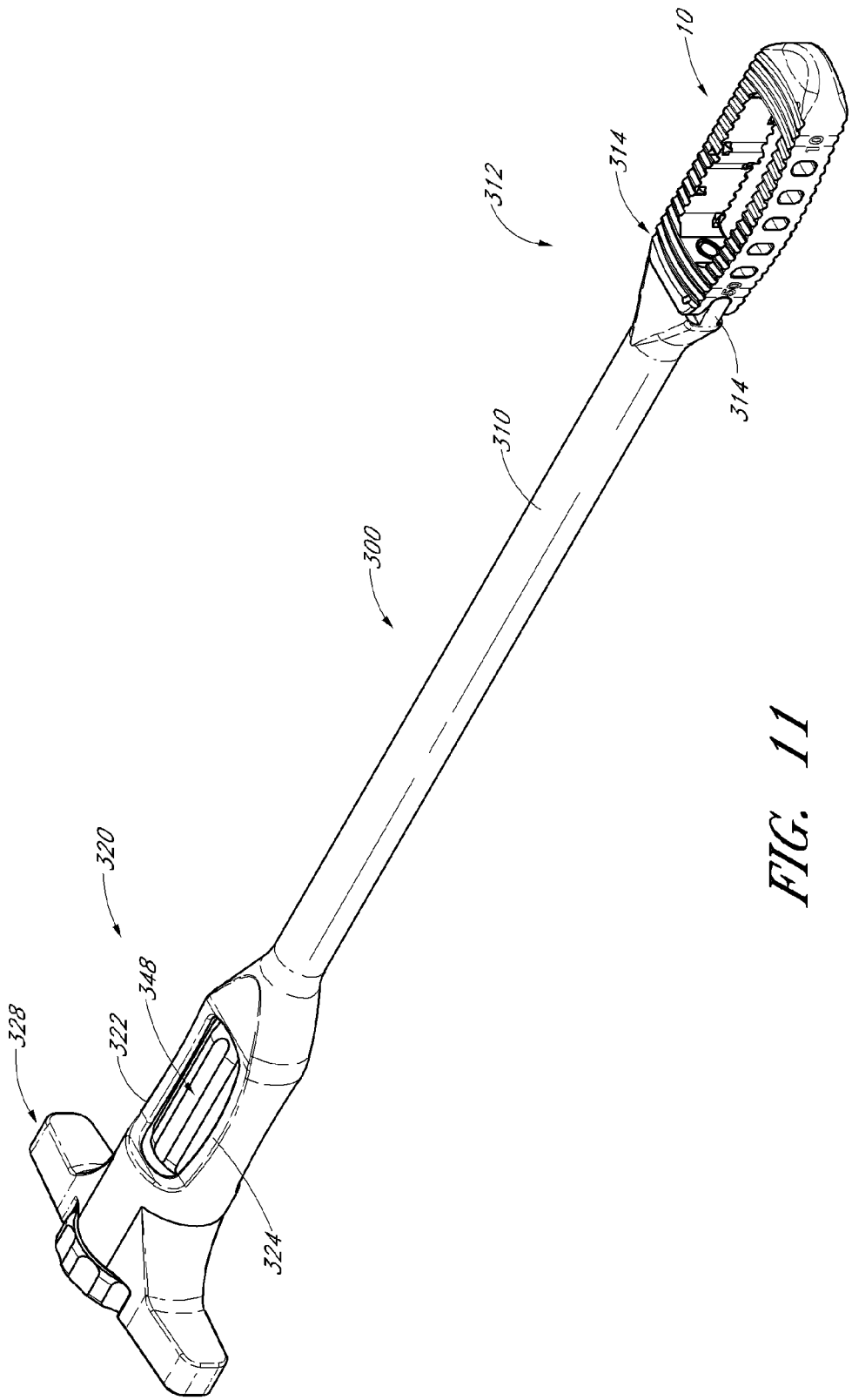
FIG. 11 illustrates a perspective view of an insertion tool assembly attached to a spinal implant, according to one embodiment.
Figure 12A:
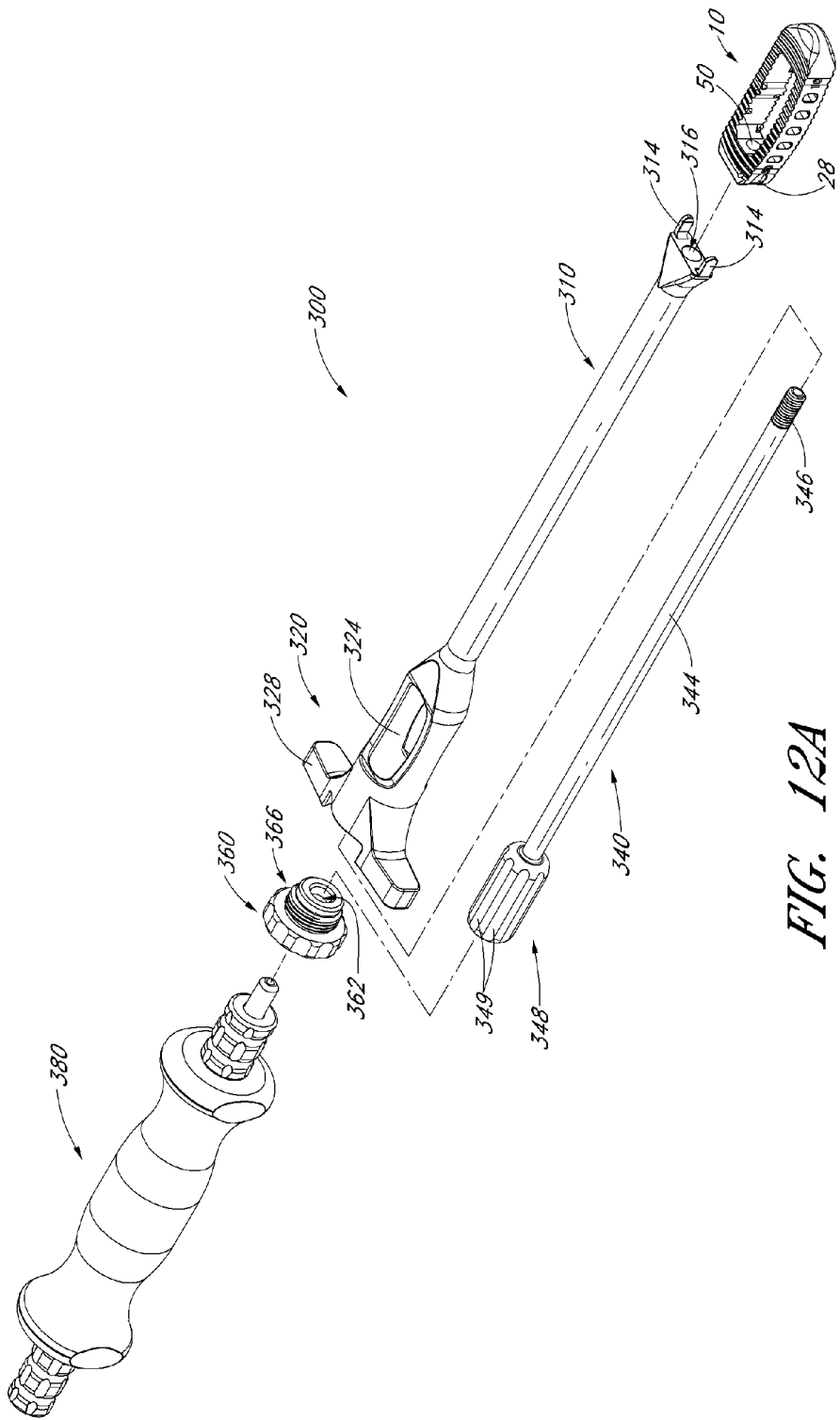
FIG. 12A illustrates an exploded perspective view of the insertion tool assembly and implant of FIG. 11.

FIG. 11 illustrates a perspective view of a spinal implant 10, identical or similar to those disclosed herein, secured to a distal end of an insertion tool assembly 300 according to one embodiment. An exploded view of the insertion tool assembly 300 of FIG. 11 is provided in FIG. 12A. As shown in FIGS. 11 and 12A, the insertion tool 300 can include an outer elongated member 310 having a distal end 312 that is adapted to releasably engage a spinal implant 10. In some embodiments, the distal end 312 of the outer elongated member 310 comprises a pair of wings or tabs 314 that are sized, shaped and otherwise configured to engage corresponding recesses or slots 28 (FIG. 1A) of an implant 10.

With continued reference to FIGS. 11 and 12A, the outer elongated member 310 can include an inner passage 316 that extends from the proximal end 320 to the distal end 312 of the insertion tool assembly 300. Thus, in some embodiments, the outer elongated member 310 is cannulated. The proximal portion 320 of the assembly 300 can include a handle 322 and a flared end 328. According to some embodiments, the outer elongated member 310 includes one or more windows 324 at or near the handle. As discussed in greater detail below, such a window can permit access to a thumbwheel or other movable control member that daylights or is exposed through the window 324.

Figure 12B:
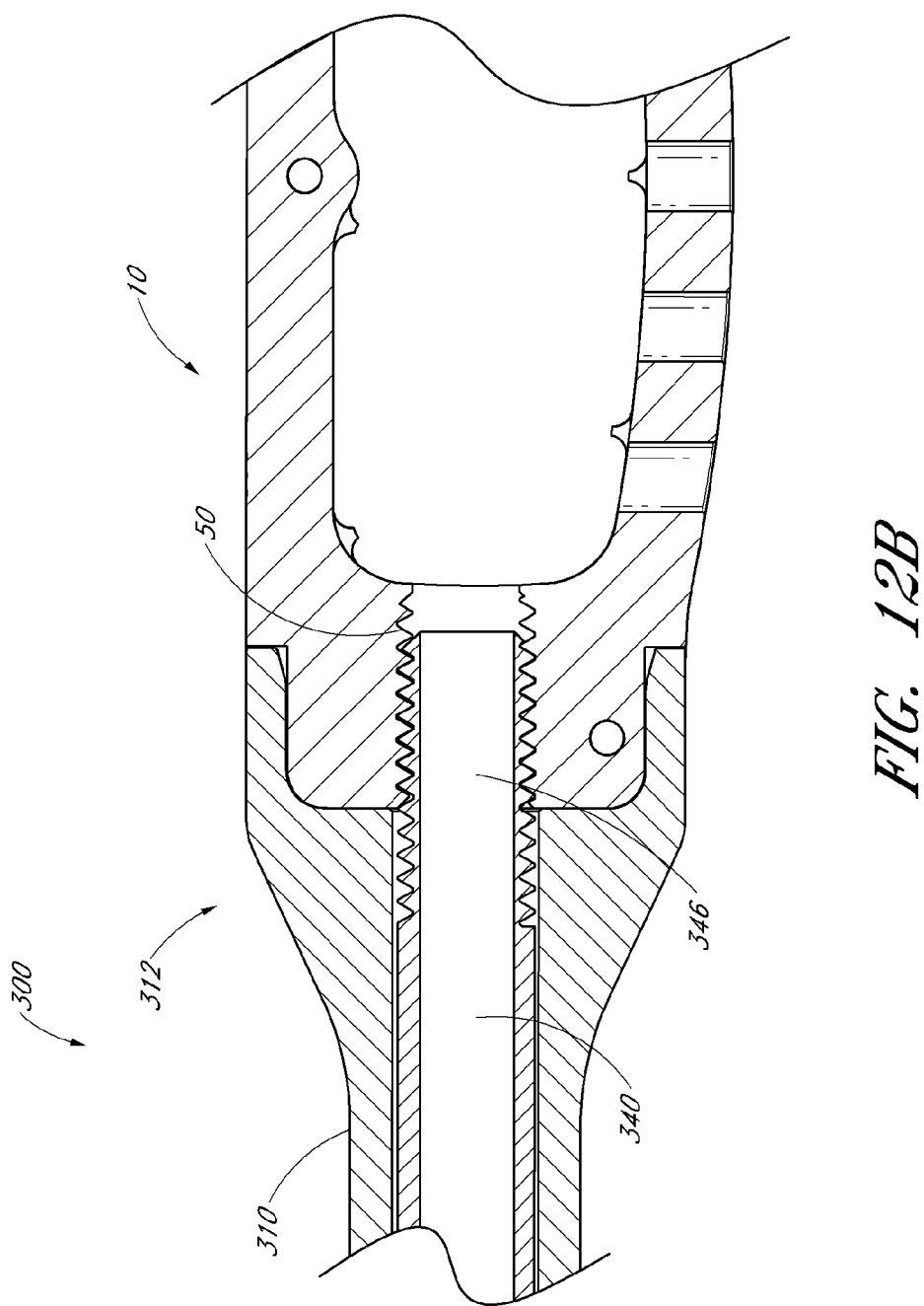
FIG. 12B illustrates a partial cross-sectional view of an insertion tool assembly secured to an implant, according to one embodiment.

As depicted in FIGS. 11 and 12A, the outer elongated member 310 can be configured to slidably receive a threaded rod 340 within its inner passage or opening 316. In some embodiments, the threaded rod 340 comprises a main elongated portion 344 having a threaded distal end 346. The threaded distal end 346 can be shaped, sized and otherwise adapted to engage a corresponding port 50 of a spinal implant (FIG. 1A). A partial cross-sectional view of such threaded engagement between the distal end 346 of the rod 340 and the port 50 of the implant 10 is illustrated in FIG. 12B. When the main elongated portion 344 is properly inserted within the cannulated opening of the outer member 310, the threaded distal end 346 can extend through the distal end of the opening 316, generally between the wings or tabs 314 of the outer member 310.

As depicted herein, the proximal end of the threaded rod 340 can comprise a generally cylindrical thumbwheel 348 that includes a larger diameter than the adjacent main elongated portion 344. According to some embodiments, at least a portion of the thumbwheel 348 is accessible through the window(s) 324 of the outer elongated member 310 when the insertion tool assembly 300 is properly assembled for use. Thus, a surgeon or other clinician can selectively rotate the thumbwheel 348 while grasping the insertion tool assembly 300 to either engage or release the implant from the assembly's distal end. The thumbwheel 348 can include a plurality of longitudinal grooves 349 and/or other features that can facilitate rotation of the threaded rod relative to the outer elongated member 310.

With continued reference to FIGS. 11 and 12A, a hammer or strike pad 360 can be secured to the proximal end of the outer elongated member 310 once the threaded rod 340 has been properly positioned therein. According to some embodiments, the hammer pad 360 includes distal threads 366 or other engagement features that are configured to engage corresponding threads or features of the outer elongated member 310. Thus, the hammer pad 360 can be releasably attached to the outer elongated member 310.

Once the targeted intervertebral space has been prepared (e.g., in accordance with a desired or required protocol), a spinal implant 10 can be secured to the distal end 312 of the insertion tool assembly 300. For example, as discussed above, the threaded distal end 346 of the rod 344 can threadably secure to the access port or opening 50 along a lateral end of the implant 10. Further, the tabs or wings 314 of the outer elongated member can engage corresponding recesses 28 of the implant 10. The insertion tool assembly 300 and the implant 10 can include one or more other types of corresponding mating or engaging features or members, either in lieu of or in addition to those disclosed herein.

Once the implant has been properly secured to the distal end of the insertion tool assembly 300, the surgeon or other clinician can drive the implant 10 into the targeted intervertebral space. In some embodiments, the insertion tool assembly 300 can be advanced into the anatomy (e.g., against any resistive forces) by impacting the proximal end of assembly 300 with a slap hammer assembly 380, a mallet or any other tool or instrument. The implantation procedure can be performed under real-time visualization in order to ensure that the implant is properly advanced and positioned.

The various components of the insertion tool assembly 300 disclosed herein, including the outer elongated member 310, the threaded rod 340 and the hammer pad 360, can comprise one or more rigid materials, such as, for example, hardened stainless steel, other types or grades of steel, titanium, other metals or alloys, composites, other natural or synthetic materials and/or the like. Such components can be reusable (e.g., sterilizable) or disposable, as desired or required.

Filling of the Implant

Once the implant has been properly positioned within the targeted intervertebral space, the internal chamber(s) of the implant can be at least partially filled with one or more grafting materials, other fill materials and/or the like. For example, the various materials that can be delivered to the internal chamber(s) of an implant include, but are not limited to: bone forming cells, demineralized bone matrix (DBM), bone morphogenetic protein (BMP), collagen matrix, bone cement, other flowable grafting agents or materials, flaky or other non-flowable grafting agents or materials, other biological or non-biological materials or substances and/or any other grafting or filler material.

As noted herein, in some embodiments, the implant is at least partially prefilled with one or more grafting agents, other fillers and/or any other material or item prior to implantation. For example, in some arrangements, a sponge, foam, other porous structure or member or other absorbent member is positioned within the implant's chamber prior to advancing the implant within the anatomy. Such an absorbent member can initially include one or more graft materials and/or can be configured to absorb or otherwise retain graft materials that are delivered into the chamber after the implant has been positioned with the targeted intervertebral space. In other arrangements, one or more graft materials and/or other fill materials can be provided in solid or partially-solid form within the implant's internal chamber(s) prior to implantation. Regardless of what items or materials are positioned within the implant prior to its delivery within a patient's spine, one or more internal prongs 74 (FIG. 2), other protruding members and/or other retaining features can be used to securely maintain such items or materials within the implant. As discussed herein, such prongs or other protruding members are configured to engage and retain materials contained within an internal chamber or cavity of the implant after such materials have at least partially solidified or cured.

According to some embodiments, once the spinal implant has been properly implanted, the insertion tool assembly 300 (FIGS. 11 and 12A) is decoupled from the implant and the assembly 300 is removed. In some embodiments, a fill tool assembly is subsequently inserted into anatomy in order to engage the implant and selectively deliver graft and/or other types of materials into the implant's internal chamber. Such a fill tool assembly can include a catheter, tube, syringe and/or other conduit that is sized, shaped and otherwise adapted to be positioned through one or more ports of the implant. As discussed in greater detail herein, such a port 50 can be identical to the port that is also used to secure the implant to the distal end of a delivery tool during delivery of the implant within the patient's anatomy. One embodiment of a kit 600 that comprises, among other things, a fill tool assembly 610 is illustrated in FIG. 13.

Figure 13:
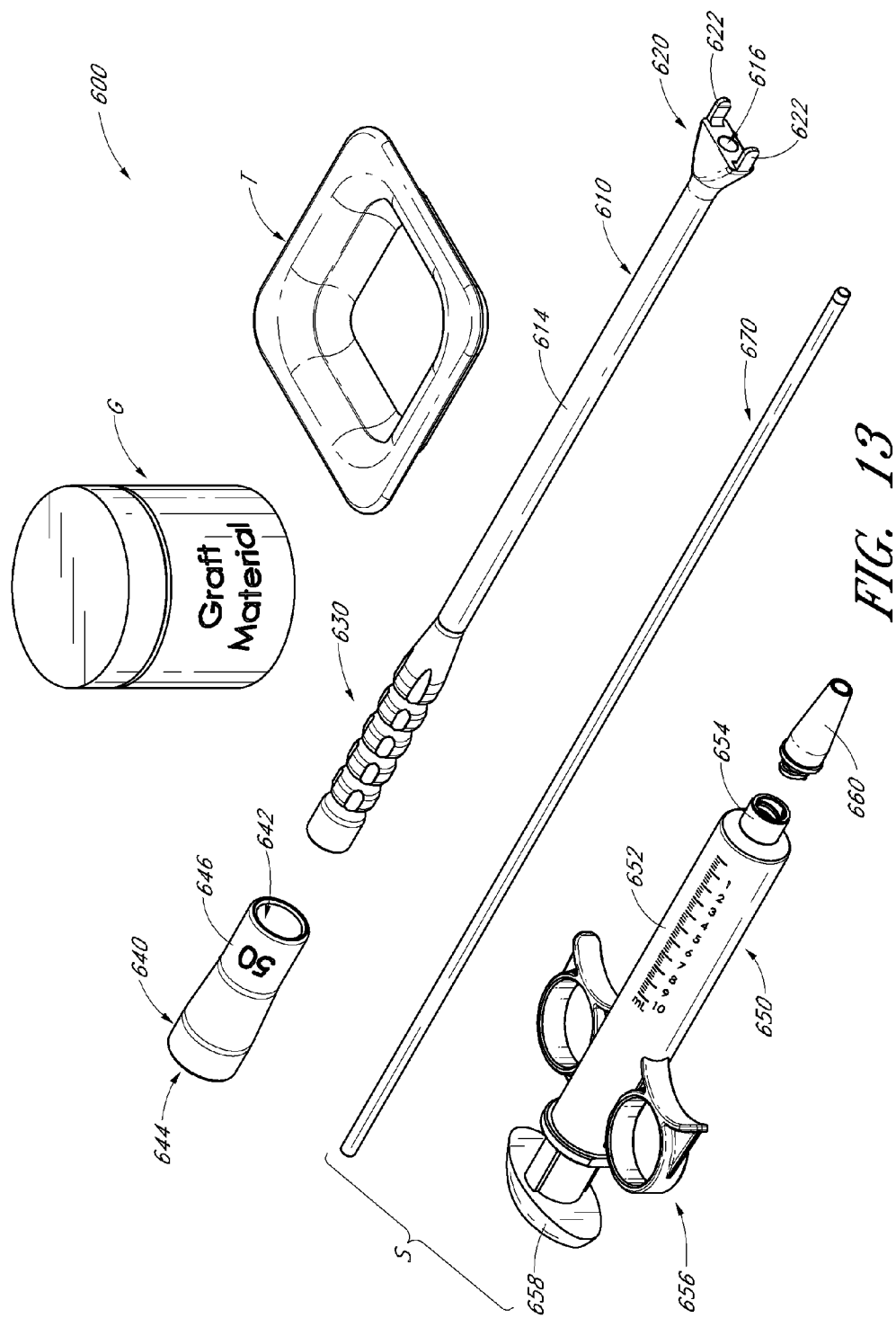
FIG. 13 illustrates a perspective view of various components of a graft fill kit, according to one embodiment.

As illustrated in FIG. 13, a fill kit 600 can include one or more of the following items: a fill tool assembly 610, a coupler 640, a syringe assembly S, a mixing tray T, a container of graft or other fill material G and/or the like. As noted above, the graft and/or other types of fill materials can be selected by the surgeon or other clinician according to a desired or required protocol or procedure. The mixing tray T can be used to combine, mix, dilute or otherwise process the various graft and/or other fill materials that will be selectively transferred within or near the implant. The various components included in the kit 600 can be disposable or reusable, as desired or required. Thus, such components can include one or more rigid, semi-rigid and/or flexible materials, including metals or alloys (e.g., stainless steel), polymeric or thermoplastic materials, rubber or other elastomeric materials, composites, other natural or synthetic materials and/or the like.

Figure 14:
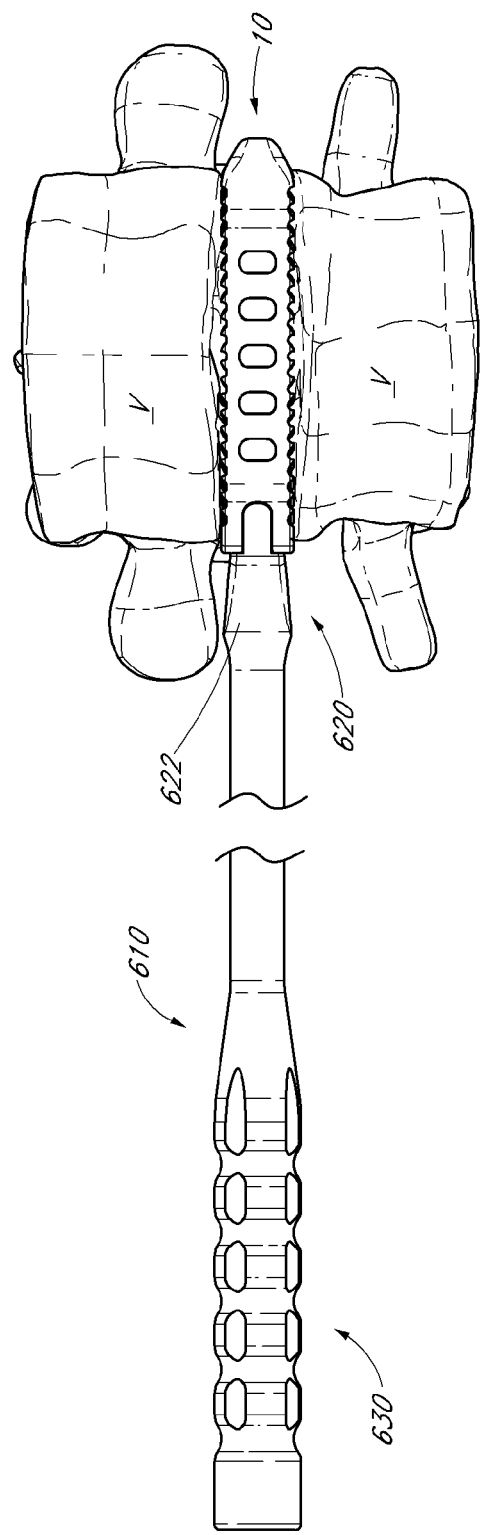
FIG. 14 illustrates an anterior side view of a fill tool assembly engaged with a spinal implant positioned within a targeted intervertebral space, according to one embodiment.

According to some embodiments, as depicted in FIG. 13, the fill tool assembly 610 includes an elongated cannulated shaft 614 that terminates in a distal end 620. The distal end 620 can include a discharge opening 616 that is in fluid communication with the internal passage of the shaft 614. Further, the distal end 620 of the fill tool assembly 610 can comprise one or more tabs or wings 622 that are sized, shaped and otherwise configured to engage corresponding recesses 28 or other features of the implant 10 (FIG. 1B). Although such tabs 622, wings or other alignment features are not necessary, they can provide assurance that the fill tool assembly has been properly positioned relative to the implant in anticipation of the subsequent filling steps. The proximal end 630 of the fill tool assembly 610 can include a handle. In the depicted embodiment, the proximal end 630 comprises a number of ring shaped portions. One embodiment of a fill tool assembly 610 aligned and engaged with an implant 10 that has been properly secured within a targeted intervertebral space is illustrated in FIG. 14.

With continued reference to FIG. 13, graft or other fill materials can be loaded into a syringe 650 of a syringe assembly S. As shown, the syringe 650 can include a barrel portion 652 into which the graft and/or other fill materials are placed. Further, the syringe 640 can include a plunger 658 that can be selectively advanced within the barrel 652 in order to help urge the graft and/or other fill materials out of the distal exit opening 654 of the syringe 650. In addition, the syringe can include a pair of grasping members 656 to facilitate handling and manipulation during use. Further, one or more mechanical tools can be used to assist the surgeon or other clinician in slidably displacing the plunger or similar movable member within the barrel. The use of such syringe/plunger configurations can be particularly helpful when transferring graft and/or other fill materials that are relatively thick, dense, concentrated, viscous or otherwise difficult to move.

Figure 15:
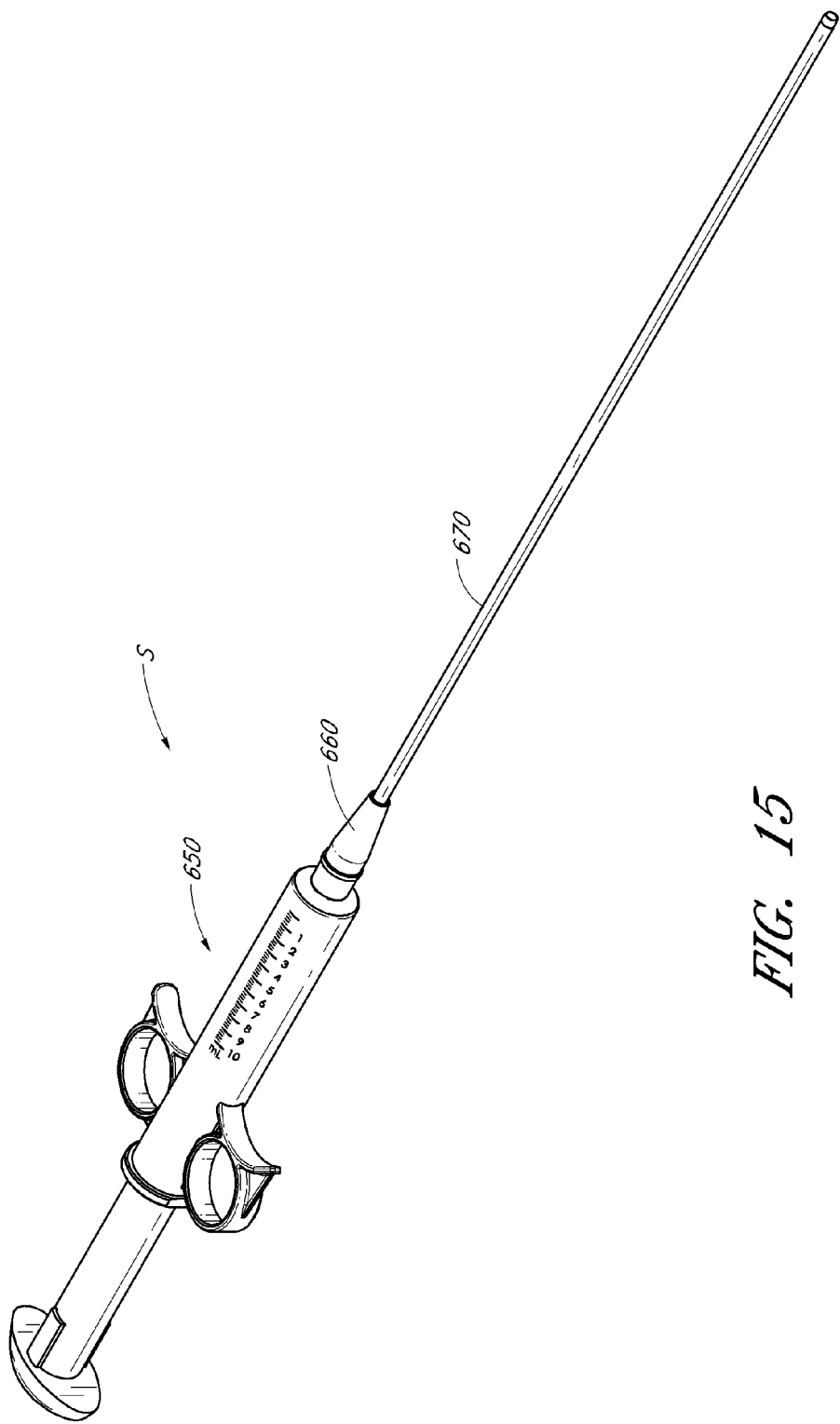
FIG. 15 illustrates a syringe assembly configured for post-filling a spinal implant with graft and/or other fill materials, according to one embodiment.

As shown in the exploded view of FIG. 13, a discharge coupling 660 can be used to attach the distal end of the syringe 650 to a length of flexible catheter, tubing or other conduit 670. In some embodiments, the tubing 670 is cable-lined and/or otherwise reinforced to reduce the likelihood of kinking during use. Such cable-lined tubing can also be used to confirm its location within the anatomy during use, as the cable lining can be visualized using one or more visualization technologies. The coupling 600 can be permanently or removably secured to the syringe 650 and/or the tubing 670 using one or more types of connection methods or devices, such as, for example, luer connections, threaded connections, friction fit or press fit connections, other types of fasteners, adhesives and/or the like. A perspective view of one embodiment of a fully-assembled syringe assembly S is illustrated in FIG. 15.

According to some embodiments, the flexible tubing or other conduit 670 and/or other components of the syringe assembly S retain the same characteristics, irrespective of the type of spinal implant that will be filled. For example, the length of the tubing 670 and coupling can be maintained consistent or substantially consistent in all kits 600. Thus, in some embodiments, a coupler 640 can be used to ensure that a volume of graft and/or fill material is adequately, accurately and consistently delivered to the implant.

As illustrated in FIG. 13, the coupler 640 can be configured to receive and engage the proximal end of the fill tool assembly 610 through its distal opening 642. Likewise, the coupler 640 can receive and engage a distal end of the syringe assembly S through its proximal opening 644. In some arrangements, the coupler 640 is selected based on the size and/or type of spinal implant that will be filled. Such a configuration can help ensure that the distal end of the syringe assembly's tubing, catheter or other conduit 670 is properly positioned within the implant's internal chamber at the initiation of the graft filling stage. For example, according to some embodiments, the coupler 640 is generally longer for the filling of smaller (e.g., shorter) implants, and generally shorter for the filling of larger (e.g., longer) implants. A kit 600 can be provided with a number of differently sized couplers 640 from which a clinician can choose (e.g., depending on the type of implant that will be at least partially filled). Further, the couplers 640 can include a size identifier 646, such as, for example, the length of the implant to be filled.

Figure 16A:
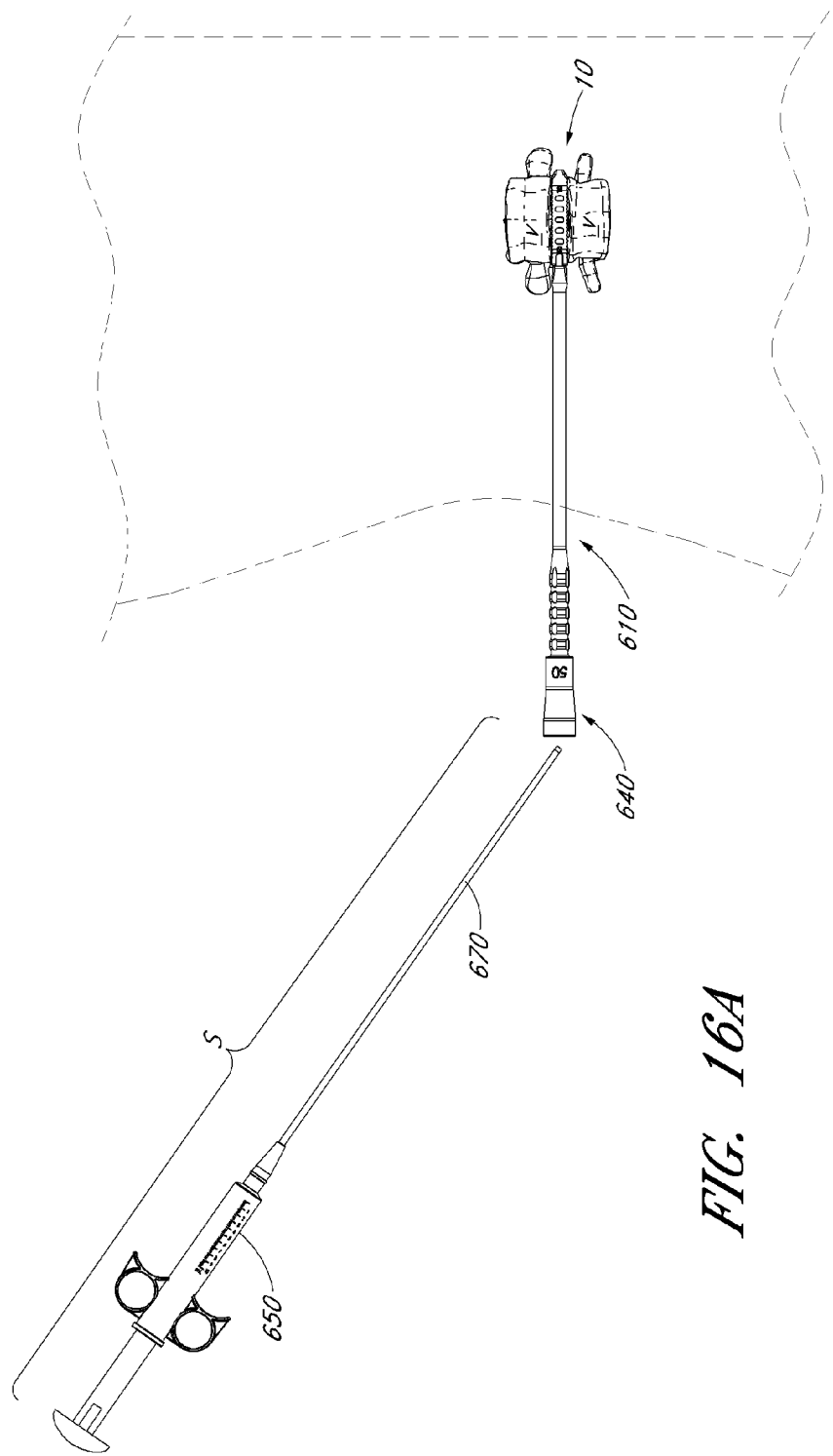
FIGS. 16A-16C illustrate various view of time-sequential steps related to positioning a syringe assembly within a fill tool assembly, according to one embodiment.
Figure 16B:
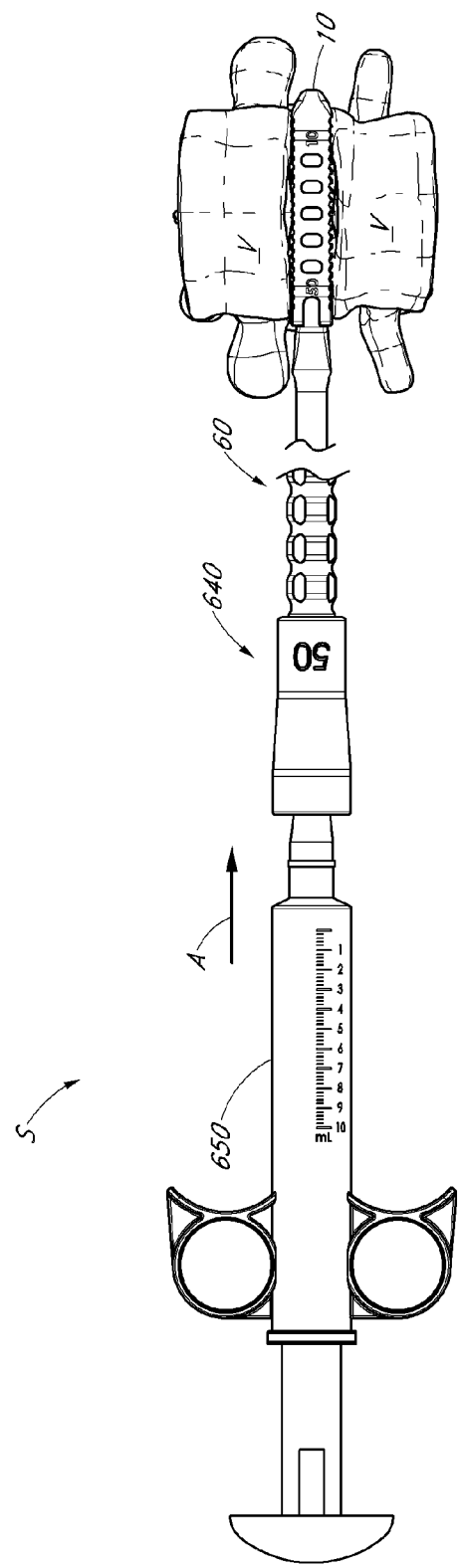
Figure 16C:
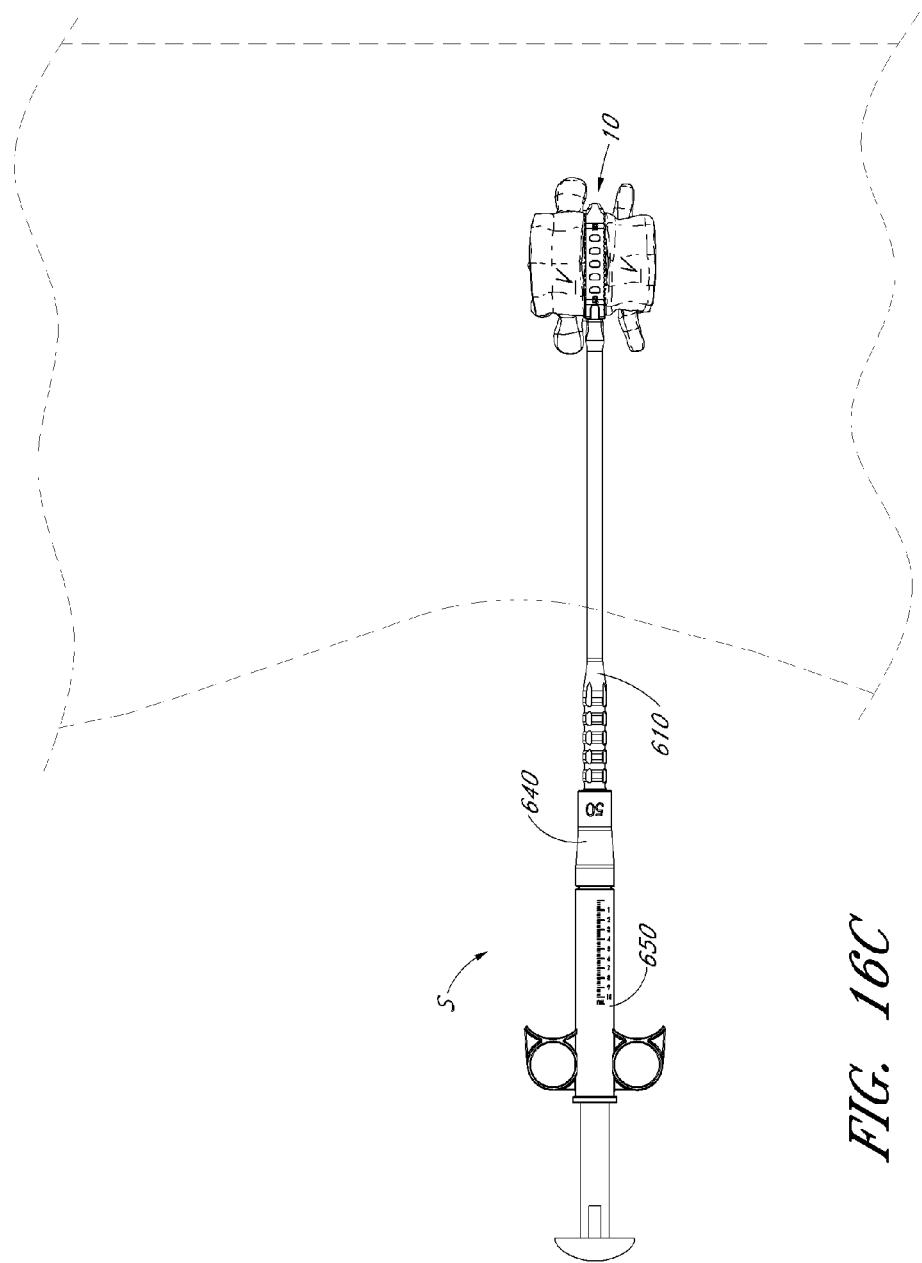

FIGS. 16A-16C illustrate three time-sequential steps performed in preparation for a post filling procedure, in which grafting and/or other fill materials are delivered within an interior portion of a spinal implant following implantation. In FIG. 16A, the fill tool assembly 610 has been properly secured to the implant 10. For example, as noted above, the tabs or wings along the distal end of the fill tool assembly 610 can be aligned with and mated with corresponding recesses of the implant. As shown, a properly selected coupler 640 can be positioned along the proximal end of the fill tube assembly 610. In some arrangements, one or more engagement members or features are positioned within the distal end of the coupler 640 to ensure that the proximal end of the fill tube assembly 610 has been properly positioned therein.

Next, as illustrated in the side view of FIG. 16B, the syringe assembly S is inserted within and advanced (e.g., in a direction generally represented by arrow A) relative to the coupler 640 and the fill tool assembly 610. FIG. 16C shows the syringe assembly S advanced to its full distal position relative to the coupler 640. Accordingly, in some embodiments, if the appropriately sized coupler 640 was used, the distal end of the tubing should be properly positioned within the chamber of the implant 10. Accordingly, the coupler assists the surgeon to accurately position the distal end of the conduit or other tubing within an internal chamber, along a specific longitudinal location of the implant. Thus, the surgeon can reliably and confidently begin injecting the graft and/or other filler materials loaded into the syringe 650 into a chamber or other interior portion of the implant 10.

According to some post fill arrangements, the surgeon can select a desired volume of graft and/or other filler materials that will be transferred to the chamber of the implant 10 according to his or her own requirements and protocols. In some embodiments, the maximum internal volume of each type of implant is provided to the clinician in corresponding printed literature, on the implant itself, using graduation marks on the syringe and/or the like.

According to some embodiments, the surgeon or clinician continues to inject the graft and/or other filler material into the interior chamber of the implant by manipulating the syringe plunger and/or by actuating some other mechanical device (e.g., hand-operated ratchet, other motorized device, etc.) that facilitates much manipulation of the plunger. The surgeon can choose to slowly, either incrementally or continuously, retract the syringe assembly S, and thus the distal end of the tubing, catheter or other conduit, while the graft and/or other fill material is delivered to the implant 10. This can facilitate and promote more even distribution of the graft and/or fill material within the internal chamber. In some embodiments, the syringe barrel, the coupler and/or any other component or features of the syringe assembly S comprise graduation marks or other indicia to assist the clinician in determining how much and/or at what rate to retract the tubing during use.

In some arrangements, the amount of graft and/or other fill materials delivered to the implant generally exceeds the internal capacity of the chamber. Thus, at some point, excess graft and/or other fill material G can be expected to begin discharging out of one or more implant openings 60 (e.g., openings located along anterior wall of the implant). This is illustrated in the embodiment depicted in FIGS. 17A and 17B. As noted above, in some embodiments, the posterior wall of the implant does not comprise any openings. Further, excess graft and/or other fill material can also be directed at the upper and/or lower interfaces of the implant and the adjacent vertebral endplate surfaces. According to some arrangements, as discussed herein, the orientation of the teeth or other engagement members along the upper and/or lower surfaces of the implant can help prevent, reduce the likelihood of and/or slow down the flow of excess graft and/or other fill material across the implant-endplate interfaces.

Figure 17A:
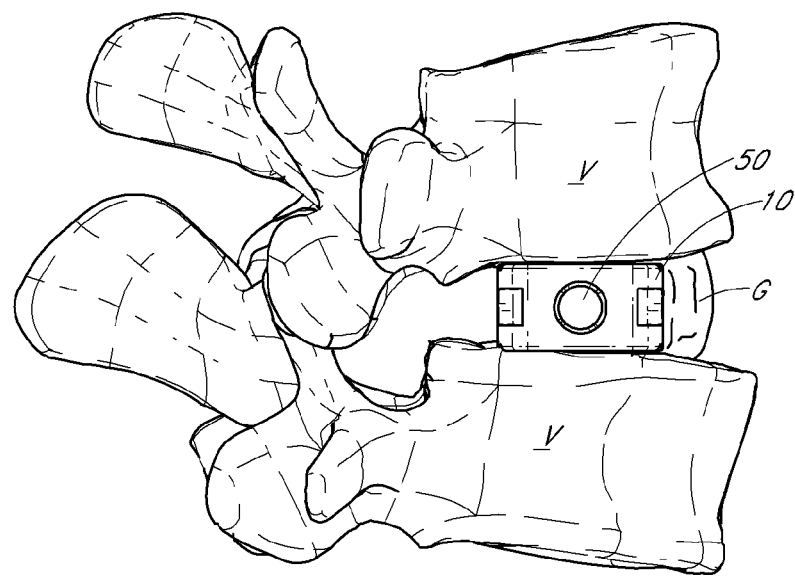
FIGS. 17A and 17B illustrates different side views of excess graft and/or other fill material that has exited the interior chamber of a spinal implant, according to one embodiment.
Figure 17B:
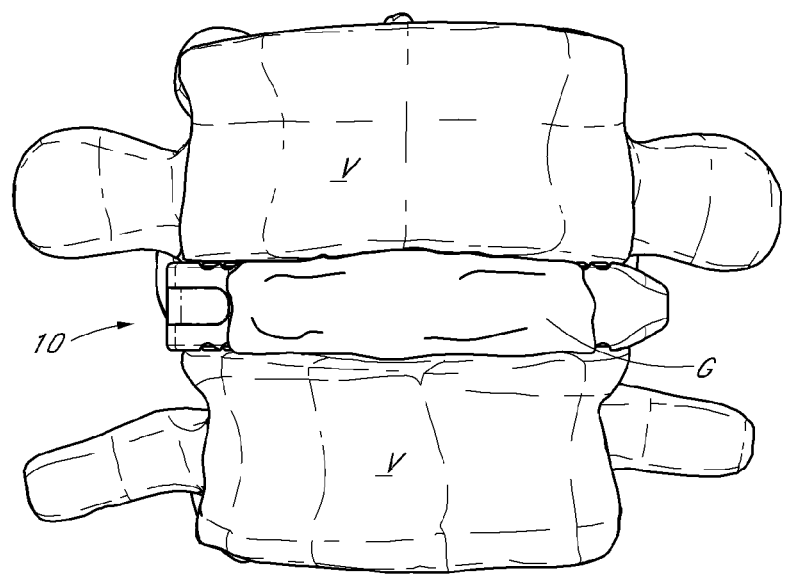

According to some embodiments, excess graft and/or other fill material G can generally fill any gap that exists between the vertebral endplates and the adjacent surfaces of the implant. This can result in improved spinal fusion. Further, spinal fusion can benefit from the excess graft and/or other fill material that exits through the openings 60 along the anterior wall of the implant 10. As illustrated in the embodiment of FIGS. 17A and 17B, such material G can fill any gaps that exist between the implant and the remaining disc material and/or other tissue along the anterior end of the spine. For example, excess graft and/or other fill material G can at least partially cover the anterior face of the implant, can span the vertical gap between adjacent vertebral V endplates along the anterior side of the implant and/or can migrate to other portions along the anterior end and/or the lateral ends of the implant to help improve fusion. As noted above, similar openings along the posterior wall of the implant can be eliminated in order to prevent or reduce the likelihood of excess graft and/or other fill materials from migrating to nerve roots, the spinal cord and/or other sensitive portions of the patient's spine.

Figure 18:
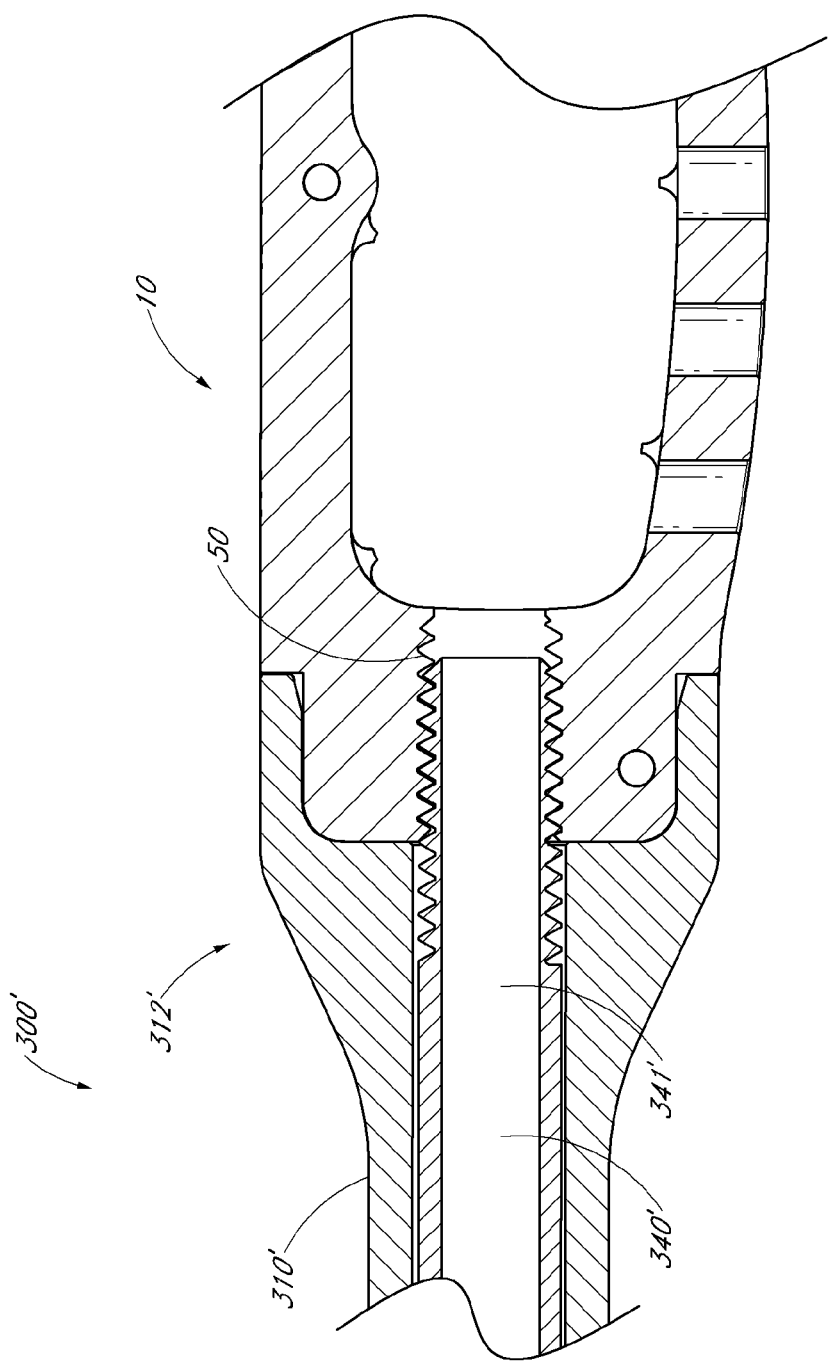
FIG. 18 illustrates a partial cross-sectional view of an insertion tool assembly having a cannulated threaded rod and secured to an implant, according to one embodiment.

According to some embodiments, as illustrated in the partial cross sectional view of FIG. 18, the threaded rod 340' of the insertion tool assembly 300' can be cannulated. Thus, the insertion tool 300' can be used to both deliver the implant to its proper intervertebral position and to subsequently fill the interior chamber(s) of the implant 10 with one or more graft and/or other fill materials. For example, in the depicted arrangement, the internal passage 341' of the cannulated threaded rod 340' can be sized, shaped and otherwise configured to receive a flexible tube, catheter or other conduit of a syringe assembly. Accordingly, the need to disengage the implant 10 from the distal end of the insertion tool assembly 300' and engage a separate fill tool assembly (as discussed herein with reference to several embodiments) can be eliminated. Instead, the insertion tool assembly 300' can remain engaged to the implant 10 while a fill tube or other conduit is inserted within the internal passage 341' of the cannulated rod 340'. Once the desired or required amount of grafting agents and/or other fill materials has been transferred to the implant, the fill conduit and the insertion tool assembly can be removed from the patient anatomy. In some embodiments, the hammer or strike plate 360 (FIG. 12A) can include a corresponding opening through which the tubing can be routed to reach the passage 341' of the cannulated rod 340'. Accordingly, the cannulated rod 340', as with any other components of the insertion tool and/or fill assemblies, can be disposable.

As discussed in relations to several embodiments disclosed herein, a spinal fusion procedure can comprise an initial implant delivery step followed by a subsequent filling step. Thus, in some embodiments, the implant is delivered within the patient's anatomy with its internal chambers or cavities either empty or only partially filled with grafting agents, other filler materials and/or other components. For example, as discussed above, an implant can comprise a porous foam, a sponge and/or one or more other absorbent devices or materials prior to its delivery within a target intervertebral space. In such an embodiment, no other materials (e.g., grafting agents, other filler materials, etc.) are present within the implant prior to or during delivery of the implant. In other arrangements, an interior chamber or other cavity of the implant is only partially filled with graft and/or other filler materials prior to or during delivery to the target interbody space.

In accordance with the various embodiments and examples disclosed herein, one or more biological and/or non-biological grafting and/or other fill materials can be injected or otherwise delivered within or near the implant following implantation. Such a procedure can help ensure that grafting and/or other filler materials are not lost during the delivery of the implant within the patient (e.g., due to hammering or other impact forces imparted on the implant during such delivery protocols). Further, by delivering excess fill materials within or near the implant, as discussed herein, more enhanced fusion of the implant to adjacent spinal surfaces (e.g., endplate surfaces) can be advantageously provided.

Figure 19:
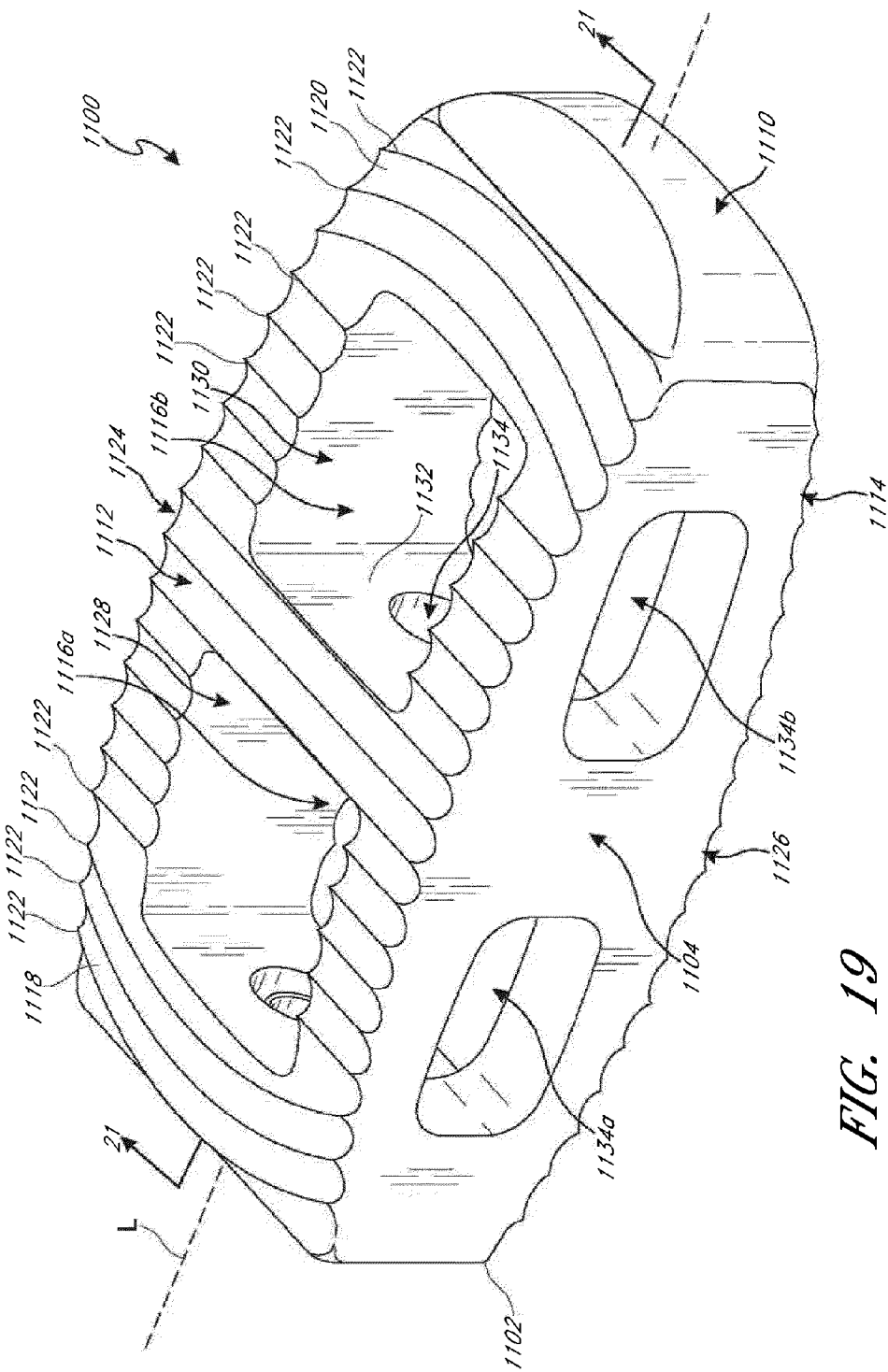
FIGS. 19 and 20 illustrate different top perspective view of a spinal implant according to one embodiment.
Figure 20:
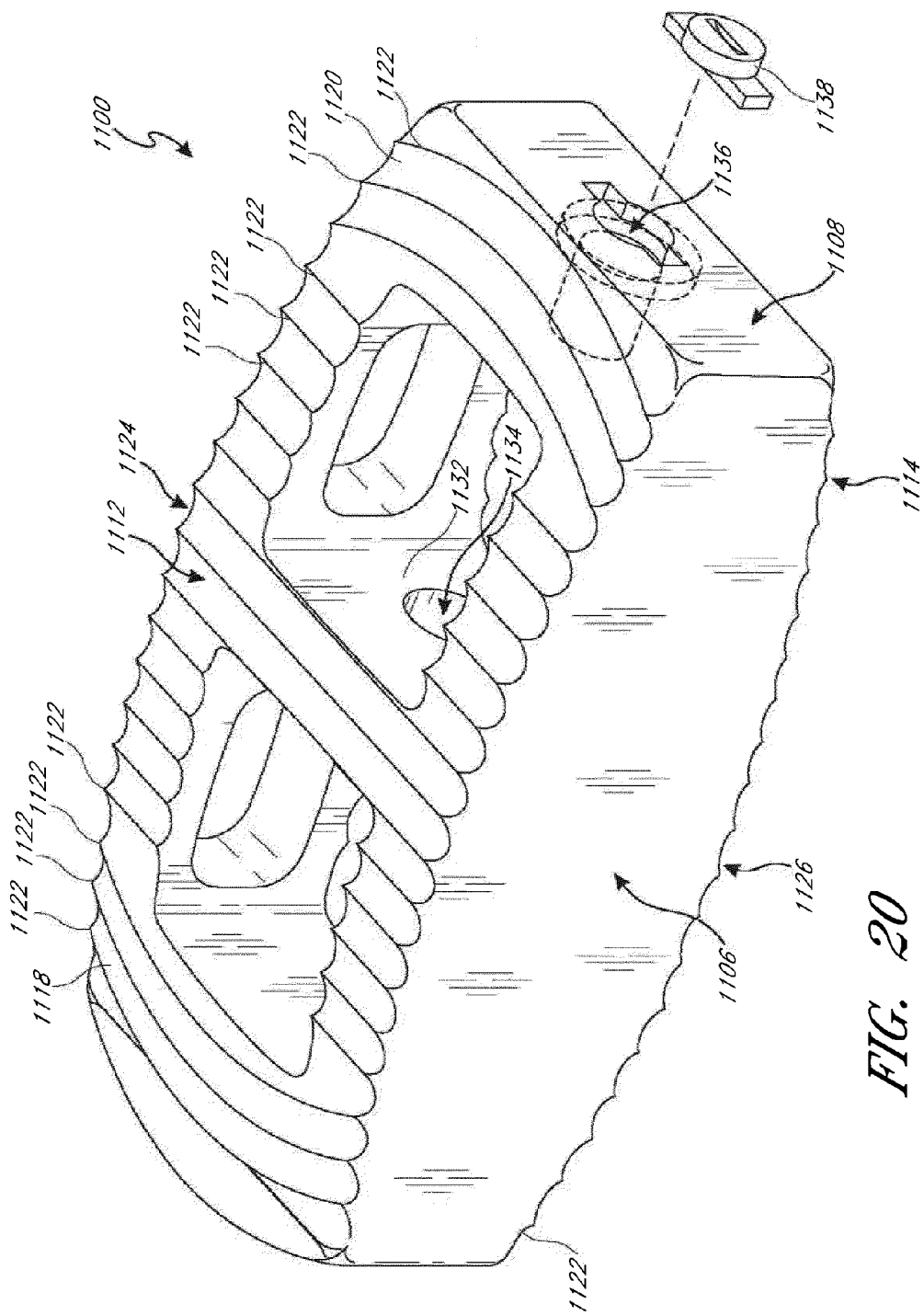
Figure 21:
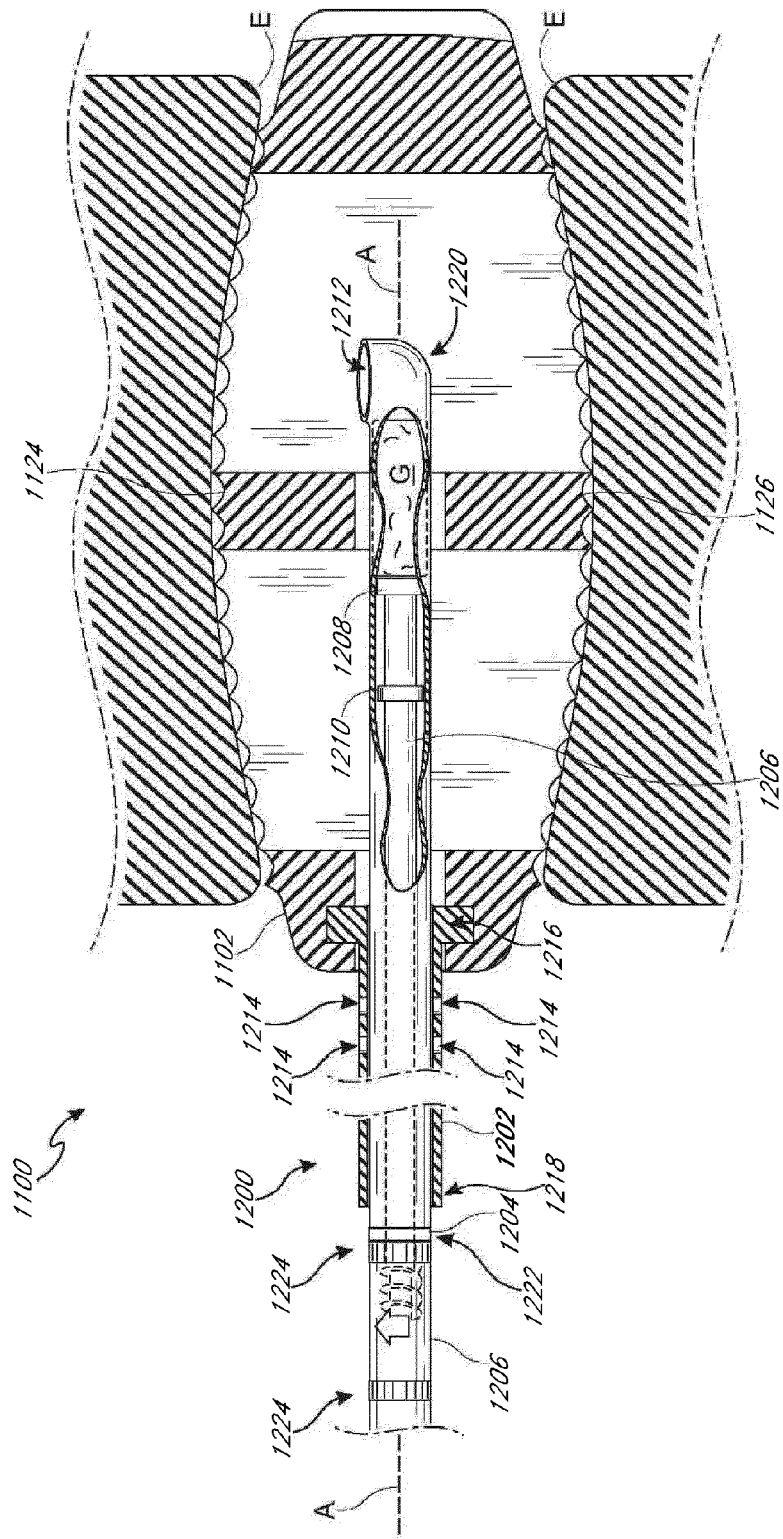
FIG. 21 illustrates a cross-sectional view of the implant of FIGS. 19 and 20.

Yet another embodiment of a spinal implant 1100 is illustrated in FIGS. 19-21. As shown, the implant 1100 can include top and bottom surfaces 1112, 1114 having one or more teeth 1122 and/or other features configured to engage corresponding portions of the patient's vertebral members (e.g., adjacent endplate surfaces). In addition, as discussed herein with respect to other embodiments, the depicted implant 1100 comprises one or more anterior holes or openings 1134a, 1134b through which excess grafting and/or other filler materials can exit the interior chambers or cavities 1116a, 1116b of the implant 1100. Further, in some embodiments, the posterior wall of the implant does not comprise any openings, thereby preventing or reducing the likelihood that excess grafting and/or other fill materials will move in that direction.

With continued reference to FIGS. 19 and 20, as with any embodiments disclosed herein, the implant 1100 can comprise one or more interior walls 1132 or baffles that divide an interior chamber or cavity into two or more areas. In some embodiments, such separate interior chambers, cavities or areas 1116a, 1116b can be in fluid communication with one another via one or more openings 1134 or other orifices within the interior wall or baffle 1132. However, in some embodiments, an implant does not comprise any interior walls or baffles. Thus, an implant can include only a single relatively large interior chamber or cavity, while maintaining a desired load bearing capacity and other structural design criteria.

As with other embodiments disclosed herein, the implant 1100 can be advantageously sized, shaped and otherwise configured to span or extend across the entire or substantially the entire width of the inferior and superior vertebral members between which it is to be placed and secured. Further, the lateral ends 1118, 1120 of the implant 1100 can comprise relatively large walls that generally coincide with load bearing portions of the adjacent vertebral members (see, for example, FIGS. 7A and 21).

As noted herein with regards to other implant arrangements, the depicted implant 1100 can comprise one or more ports 1136 along one or more of its surfaces. For example, as illustrated in FIGS. 19-21, a single port 1136 can be provided along one of the lateral side walls of the implant 1100. As discussed in greater detail herein, such a port 1136 can be configured to receive an implant delivery tool (e.g., to assist a surgeon in moving the implant through the patient's anatomy to a target intervertebral space) and/or to pass one or more fill tubes or conduits for post-filling, at least partially, an interior chamber or cavity of the implant with grafting agents and/or other fill materials. In any of the implant embodiments disclosed herein, or equivalents thereof, such a port that can serve a dual purpose related to implant positioning and graft delivery can be located along any side wall (e.g., lateral, anterior, posterior) of the implant.

In addition, as illustrated in FIG. 20, a cap or other sealing member 1138 can be secured to the port 1136. Such a cap 1138 can help ensure that grafting and/or filler materials delivered or otherwise positioned within the interior of the implant do not escape through the port 1136. In other embodiments, the port can comprise one or more valves or other flow blocking members to help reduce the inadvertent escape of materials from the interior of the implant.

With reference to the side cross-sectional view of FIG. 21, the implant port can be sized, shaped and otherwise configured to receive a fill tube or other conduit 1200. Such a fill tube 1200 can be passed through the port and into one or more interior chambers or other cavities of the implant 1100. As shown, a distal end 1220 of the fill tube 1200 can be angled so that the outlet 1212 is oriented generally perpendicular to the axis A of the port and the fill tube 1200. In other embodiments, the face of the outlet 1212 can be oriented along a different angle (e.g., between 0 and 90 degrees relative the longitudinal axis A), as desired or required. In some embodiments, a plunger assembly 1206 can be positioned within the fill tube or can be operatively coupled to it. Accordingly, such a plunger assembly 1206 can be selectively actuated in order to provide the necessary driving force to move grafting material G through the tube 1200 and into an interior area of the implant.

According to some embodiments, as illustrated in FIG. 21, the top and/or bottom surfaces of a spinal implant can be generally curved or rounded. In such arrangements, the curvature of the top and/or bottom surface can be configured to match or generally align with the shape of the adjacent endplates E or other native tissue of the patient. However, as discussed above with reference to the implant embodiment illustrated in FIGS. 1A and 1B, the top and/or bottom surfaces can be generally planar.

To assist in the description of the disclosed embodiments, words such as upward, upper, bottom, downward, lower, rear, front, vertical, horizontal, upstream, downstream have been used above to describe different embodiments and/or the accompanying figures. It will be appreciated, however, that the different embodiments, whether illustrated or not, can be located and oriented in a variety of desired positions.

Although the subject matter provided in this application has been disclosed in the context of certain specific embodiments and examples, it will be understood by those skilled in the art that the inventions disclosed in this application extend beyond the specifically disclosed embodiments to other alternative embodiments and/or uses of the subject matter disclosed herein and obvious modifications and equivalents thereof. In addition, while a number of variations of the inventions have been shown and described in detail, other modifications, which are within the scope of these inventions, will be readily apparent to those of skill in the art based upon this disclosure. It is also contemplated that various combinations or subcombinations of the specific features and aspects of the embodiments may be made and still fall within the scope of the inventions disclosed herein. Accordingly, it should be understood that various features and aspects of the disclosed embodiments can be combine with or substituted for one another in order to form varying modes of the disclosed inventions. Thus, it is intended that the scope of the subject matter provided in the present application should not be limited by the particular disclosed embodiments described above, but should be determined only by a fair reading of the claims that follow.

What is claimed is:

1. A spinal implant configured for placement within an intervertebral space, between a first vertebral body and a second vertebral body, of a subject, comprising:
    an anterior wall and a posterior wall, the posterior wall being generally opposite of said anterior wall, wherein the posterior wall does not comprise any openings;
    a first lateral wall and a second lateral wall extending between the anterior wall and the posterior wall;
    at least one internal chamber defined, at least in part, by the anterior wall, the posterior wall and the first and second lateral walls, the at least one internal chamber extending at least partially from a top surface to a bottom surface of the implant; and
    at least one opening extending through the anterior wall, said at least one opening being in fluid communication with the at least one internal chamber;
    wherein the implant comprises a lateral lumbar implant that is configured to be inserted into an intervertebral space using a lateral delivery approach;
    wherein the implant comprises a length of at least 40 mm to laterally span across the first and second vertebral bodies when the implant is inserted using a lateral delivery approach, and wherein each of the first and second lateral walls is configured to generally align with peripheral bearing areas of the first and second vertebral bodies and to support adjacent cortical rims of the first and second vertebral bodies, wherein the adjacent cortical rims are located near the lateral, circumferential ends of the first and second vertebral bodies, such that, after implantation, a bearing load created by the adjacent vertebral bodies is concentrated toward the walls of the implant and away from a central portion of each of the vertebral bodies;
    wherein a length of the first and second lateral walls is a minimum of 12% of an overall length of the implant; and
    wherein an axis that extends along a width of the implant between the anterior wall and the posterior wall is generally linear.

2. The implant of claim 1, further comprising an access port along at least one of the first lateral wall and the second lateral wall, the access port configured to releasably secure to an insertion tool.

3. The implant of claim 2, wherein the access port is generally circular.

4. The implant of claim 2, wherein the access port is adapted to receive a fill conduit therethrough, said fill conduit being configured to selectively deliver a grafting material into the at least one internal chamber of the implant.

5. The implant of claim 2, wherein a minimum ratio of a diameter of the access port to a height of the first or second lateral wall through which the at least one access port is located is approximately 0.5.

6. The implant of claim 1 wherein at least one of the first lateral wall and the second lateral wall comprises a tapered portion to facilitate insertion of the implant into the intervertebral space.

7. The implant of claim 1, wherein the implant is configured for placement within a lumbar or thoracic portion of a subject's spine.

8. The implant of claim 1, wherein the implant is configured for lateral insertion into the intervertebral space.

9. The implant of claim 1, wherein the implant comprises polyether etherketone (PEEK).

10. The implant of claim 1, wherein the at least one internal chamber does not comprise any interior walls or baffles.

11. The implant of claim 1, wherein the at least one internal chamber comprises at least two internal sub-chambers divided by at least one interior wall.

12. The implant of claim 1, wherein the implant comprises at least one radio-opaque marker.

13. A spinal implant configured for placement within an intervertebral space, between a first vertebral body and a second vertebral body, of a subject, comprising:
    an anterior wall and a posterior wall, the posterior wall being generally opposite of said anterior wall;
    a first lateral wall and a second lateral wall extending between the anterior wall and the posterior wall;
    the anterior wall, the posterior wall, the first lateral wall and the second lateral wall defining at least one internal chamber, wherein the implant comprises a lateral lumbar implant that is configured to be inserted into an intervertebral space using a lateral delivery approach; and
    at least one access port extending through the first lateral wall or the second lateral wall, the at least one access port configured to releasably secure the implant to a delivery tool for advancing the implant into the intervertebral space of the subject;
    wherein the implant comprises a length of at least 40 mm so that each of the first lateral wall and the second lateral wall is generally aligned with a peripheral bearing area of the first and second vertebral bodies of the subject and so that the implant laterally spans across the first and second vertebral bodies when the implant is inserted using a lateral delivery approach, wherein each of the first and second lateral walls is shaped, sized and configured to support adjacent cortical rims of the first and second vertebral bodies, the cortical rims defining a central portion of each vertebral body, wherein the adjacent cortical rims are located near the lateral, circumferential ends of the first and second vertebral bodies, such that, after implantation, a bearing load created by the adjacent vertebral bodies is concentrated along the walls of the implant and away from the central portions of the vertebral bodies;

wherein a length of the first and second lateral walls is a minimum of 12% of an overall length of the implant; and wherein an axis that extends along a width of the implant between the anterior wall and the posterior wall is generally linear.

14. The implant of claim 13, wherein the implant is configured for lateral or translateral insertion into the intervertebral space.

15. The implant of claim 13, wherein the at least one internal chamber does not comprise any interior walls or baffles.

16. The implant of claim 13, wherein the implant comprises at least one radio-opaque marker.

17. The implant of claim 13, wherein the at least one access port comprises a minimum diameter of approximately 6 mm.

18. The implant of claim 13, wherein a ratio of a diameter of the at least one access port to a height of the lateral walls is between approximately 0.4 and 0.8.

19. The implant of claim 18, wherein a minimum ratio of a diameter of the at least one access port to a height of the lateral walls is approximately 0.5.

20. A spinal implant configured for placement within an intervertebral space, between a first vertebral body and a second vertebral body, of a subject, comprising:

an anterior wall and a posterior wall, the posterior wall being generally opposite of said anterior wall;

a first lateral wall and a second lateral wall extending between the anterior wall and the posterior wall;

the anterior wall, the posterior wall, the first lateral wall and the second lateral wall defining at least one internal chamber, wherein the implant comprises a lateral lumbar implant that is configured to be inserted into an intervertebral space using a lateral delivery approach; and at least one access port extending through the first lateral wall or the second lateral wall, the at least one access port configured to releasably secure the implant to a delivery tool for advancing the implant into the intervertebral space of the subject;

wherein the implant is sized, shaped and configured to laterally span across the first and second vertebral bodies when the implant is inserted using a lateral delivery approach;

wherein each of the first and second lateral walls is configured to generally align with peripheral bearing areas of the first and second vertebral bodies and to support adjacent cortical rims of the first and second vertebral bodies, wherein the adjacent cortical rims are located near the lateral, circumferential ends of the first and second vertebral bodies, such that, after implantation, a bearing load created by the adjacent vertebral bodies is concentrated toward the walls of the implant;

wherein a length of the first and second lateral walls is a minimum of 12% of an overall length of the implant; and wherein an axis that extends along a width of the implant between the anterior wall and the posterior wall is generally linear.

\* \* \* \* \*